(12) United States Patent
Brodney et al.

(10) Patent No.: US 10,253,042 B2
(45) Date of Patent: *Apr. 9, 2019

(54) N-(2-(2-AMINO-6-SUBSTITUTED-4,4A,5,6-TETRAHYDROPYRANO[3,4-D][1,3]OXAZIN-8A(8H)-YL)-THIAZOL-4-YL) AMIDES

(71) Applicant: Pfizer Inc., New York, NY (US)

(72) Inventors: Michael Aaron Brodney, Newton, MA (US); Christopher Ryan Butler, Canton, MA (US); Lei Zhang, Auburndale, MA (US); Brian Thomas O'Neill, Haddam, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/678,511

(22) Filed: Aug. 16, 2017

(65) Prior Publication Data

US 2017/0369506 A1 Dec. 28, 2017

Related U.S. Application Data

(63) Continuation of application No. 15/272,651, filed on Sep. 22, 2016, now Pat. No. 9,771,379.

(60) Provisional application No. 62/376,568, filed on Aug. 18, 2016, provisional application No. 62/232,004, filed on Sep. 24, 2015.

(51) Int. Cl.
*A01N 43/00* (2006.01)
*A61K 31/553* (2006.01)
*C07D 498/04* (2006.01)
*C07D 498/10* (2006.01)

(52) U.S. Cl.
CPC ......... *C07D 498/04* (2013.01); *C07D 498/10* (2013.01)

(58) Field of Classification Search
CPC ..................... C07D 498/04; C07D 498/10
See application file for complete search history.

(56) References Cited

U.S. PATENT DOCUMENTS

| | | | |
|---|---|---|---|
| 5,324,723 A | 6/1994 | Baker et al. |
| 5,750,349 A | 5/1998 | Suzuki et al. |
| 6,638,953 B2 | 10/2003 | Gaster et al. |
| 6,936,629 B2 | 8/2005 | Kong et al. |
| 7,074,809 B2 | 7/2006 | Arora et al. |
| 7,115,600 B2 | 10/2006 | Wager et al. |
| 7,196,104 B2 | 3/2007 | Askew, Jr. et al. |
| 7,285,293 B2 | 10/2007 | Castillo et al. |
| 7,759,373 B2 | 7/2010 | Hongu et al. |
| 7,975,664 B2 | 7/2011 | Himsel et al. |
| 8,158,620 B2 | 4/2012 | Suzuki et al. |
| 8,198,269 B2 | 6/2012 | Motiki et al. |
| 8,278,441 B2 | 10/2012 | Mergott et al. |
| 8,729,071 B2 | 5/2014 | Scott et al. |
| 8,822,456 B2 | 9/2014 | Brodney et al. |
| 8,865,706 B2 | 10/2014 | Brodney et al. |
| 8,865,712 B2 | 10/2014 | Badiger et al. |
| 8,933,221 B2 | 1/2015 | Brodney et al. |
| 8,962,616 B2 | 2/2015 | Brodney et al. |
| 9,029,408 B2 | 5/2015 | Miller et al. |
| 9,045,498 B2 | 6/2015 | Brodney et al. |
| 9,045,499 B2 | 6/2015 | Brodney et al. |
| 9,192,612 B2 | 11/2015 | Brodney et al. |
| 9,198,917 B2 | 12/2015 | Brodney et al. |
| 9,233,981 B1 | 1/2016 | Brodney et al. |
| 9,260,455 B2 | 2/2016 | Brodney et al. |
| 9,315,520 B2 | 4/2016 | Brodney et al. |
| 9,403,846 B2 | 8/2016 | Brodney et al. |
| 9,428,523 B2 | 8/2016 | Brodney et al. |
| 9,605,007 B2 | 3/2017 | Brodney et al. |
| 9,611,264 B1 | 4/2017 | Brodney et al. |
| 2003/0073655 A1 | 4/2003 | Shain |
| 2003/0195205 A1 | 10/2003 | DeNinno et al. |
| 2004/0192898 A1 | 9/2004 | Jia et al. |
| 2004/0220186 A1 | 11/2004 | Bell et al. |
| 2005/0019328 A1 | 1/2005 | Schenk et al. |
| 2005/0043354 A1 | 2/2005 | Wager et al. |
| 2005/0048049 A1 | 3/2005 | Schenk et al. |
| 2005/0256135 A1 | 11/2005 | Lunn et al. |
| 2005/0267009 A1 | 12/2005 | Deagle |

(Continued)

FOREIGN PATENT DOCUMENTS

WO WO-2013030713 A1 * 3/2013 ........... C07D 513/04
WO WO-2013164730 A1 * 11/2013 ........... C07D 513/04

*Primary Examiner* — Jean P Cornet
(74) *Attorney, Agent, or Firm* — Lisa A. Samuels

(57) ABSTRACT

The present invention is directed to compounds, tautomers and pharmaceutically acceptable salts of the compounds which are disclosed, wherein the compounds have the structure of Formula I,

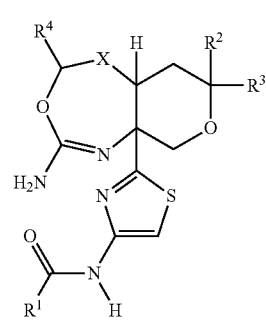

wherein the variables $R^1$, $R^2$, $R^3$, $R^4$ and X are as defined in the specification. Corresponding pharmaceutical compositions, methods of treatment, methods of synthesis, and intermediates are also disclosed.

6 Claims, No Drawings

(56) References Cited

U.S. PATENT DOCUMENTS

| | | |
|---|---|---|
| 2005/0267095 A1 | 12/2005 | Bernardelli et al. |
| 2005/0267100 A1 | 12/2005 | Elliott et al. |
| 2006/0036772 A1 | 3/2006 | Arora et al. |
| 2006/0057701 A1 | 3/2006 | Rosenthal et al. |
| 2006/0106035 A1 | 5/2006 | Hendrix et al. |
| 2006/0111372 A1 | 5/2006 | Hendrix et al. |
| 2006/0178501 A1 | 8/2006 | Summers et al. |
| 2007/0031416 A1 | 2/2007 | Shoji et al. |
| 2007/0160616 A1 | 7/2007 | Rosenthal et al. |
| 2007/0179175 A1 | 8/2007 | Lunn |
| 2008/0096955 A1 | 4/2008 | Wager et al. |
| 2008/0176925 A1 | 7/2008 | Butler et al. |
| 2009/0054482 A1 | 2/2009 | Chan et al. |
| 2010/0056618 A1 | 3/2010 | Mascitti et al. |
| 2010/0093999 A1* | 4/2010 | Motoki ............... C07D 513/04 544/48 |
| 2010/0285145 A1 | 11/2010 | Darout et al. |
| 2011/0009395 A1 | 1/2011 | Edmund et al. |
| 2011/0027279 A1 | 2/2011 | Chain |
| 2011/0038861 A1 | 2/2011 | Rosenthal |
| 2011/0046122 A1 | 2/2011 | Andreini et al. |
| 2011/0207723 A1 | 8/2011 | Motoki et al. |
| 2012/0202804 A1 | 8/2012 | Ellard et al. |
| 2012/0225880 A1 | 9/2012 | Jiaang et al. |
| 2012/0245155 A1* | 9/2012 | Yoshida ............... C07D 265/18 514/224.2 |
| 2013/0053373 A1 | 2/2013 | Brodney et al. |
| 2013/0296308 A1 | 11/2013 | Brodney et al. |
| 2014/0107109 A1 | 4/2014 | Lewis et al. |
| 2014/0128382 A1 | 5/2014 | Wu et al. |
| 2014/0163015 A1 | 6/2014 | Brodney et al. |
| 2014/0228356 A1 | 8/2014 | Brodney et al. |
| 2014/0323474 A1 | 10/2014 | Brodney et al. |
| 2014/0364426 A1 | 12/2014 | Brodney et al. |
| 2015/0087637 A1 | 3/2015 | Brodney et al. |
| 2015/0133438 A1 | 5/2015 | Brodney et al. |
| 2015/0224110 A1 | 8/2015 | Brodney et al. |
| 2015/0231144 A1 | 8/2015 | Brodney et al. |
| 2015/0239908 A1 | 8/2015 | Brodney et al. |
| 2015/0291621 A1 | 10/2015 | Brodney et al. |
| 2015/0376207 A1 | 12/2015 | Brodney et al. |
| 2016/0002264 A1 | 1/2016 | Brodney et al. |
| 2016/0152637 A1 | 6/2016 | Brodney et al. |
| 2017/0088558 A1 | 3/2017 | Brodney et al. |
| 2017/0151252 A1 | 6/2017 | Brodney et al. |

\* cited by examiner

N-(2-(2-AMINO-6-SUBSTITUTED-4,4A,5,6-TETRAHYDROPYRANO[3,4-D][1,3]OXAZIN-8A(8H)-YL)-THIAZOL-4-YL) AMIDES

This application is a continuation application of U.S. patent application Ser. No. 15/272,651, filed Sep. 22, 2016, which claims the benefit of U.S. Provisional Patent Application No. 62/376,568, filed on Aug. 18, 2016 and U.S. Provisional Patent Application No. 62/232,004, filed on Sep. 24, 2015, the disclosures of which are hereby incorporated by reference in their entirety.

FIELD OF THE INVENTION

The present invention relates to small molecule compounds and pharmaceutically acceptable salts thereof that are inhibitors of β-site amyloid precursor protein (APP) Cleaving Enzyme 1 (BACE1) and inhibitors of BACE2. This invention relates to inhibiting the production of A-beta peptides that can contribute to the formation of neurological deposits of amyloid protein. The present invention also relates to the treatment of Alzheimer's disease (AD) and other neurodegenerative and/or neurological disorders, as well as the treatment of diabetes in mammals, including humans. More particularly, this invention relates to oxamidine compounds and pharmaceutically acceptable salts thereof useful for the treatment of neurodegenerative and/or neurological disorders, such as AD and Down's syndrome, related to A-beta peptide production.

BACKGROUND OF THE INVENTION

Dementia results from a wide variety of distinctive pathological processes. The most common pathological processes causing dementia are Alzheimer's disease ("AD"), cerebral amyloid angiopathy ("CM") and prion-mediated diseases (see, e.g., Haan et al., Clin. Neurol. Neurosurg., 1990, 92(4):305-310; Glenner et al., J. Neurol. Sci., 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050.

The accumulation of amyloid-β (Aβ peptides) is believed to be one of the underlying causes of Alzheimer's disease (AD), which is the most common cause of cognitive decline in the elderly (Hardy & Allsop, Trends Pharmacol Sci., 1991; 12(10):383-8; Selkoe, Behav. Brain Res., 2008; 192 (1):106-13). Aβ, the major protein constituent of amyloid plaques, is derived from sequential cleavage of the type I integral membrane protein, amyloid precursor protein (APP) by two proteases, β- and γ-secretase. Proteolytic cleavage of APP by the β-site APP cleaving enzymes (BACE1 and BACE2) generates a soluble N-terminal ectodomain of APP (sAPPβ) and the C-terminal fragment C99. Subsequent cleavage of the membrane-bound C99 fragment by the γ-secretase liberates the various Aβ peptide species, of which Aβ40 and Aβ42 are the most predominant forms (Vassar et al., J. Neurosci., 2009; 29(41):12787-94; Marks & Berg, Neurochem. Res., 2010; 35:181-210). Therefore, limiting the generation of Aβ directly through inhibition of BACE1 is one of the most attractive approaches for the treatment of AD, as BACE1 inhibitors could effectively inhibit the formation of all predominant Aβ peptides.

In addition, it has been determined that BACE1 knock-out mice had markedly enhanced clearance of axonal and myelin debris from degenerated fibers, accelerated axonal regeneration, and earlier reinnervation of neuromuscular junctions compared with littermate controls. These data suggest BACE1 inhibition as a therapeutic approach to accelerate regeneration and recovery after peripheral nerve damage. (See Farah et al., J. Neurosci., 2011, 31(15): 5744-5754).

Insulin resistance and impaired glucose homoeostasis are important indicators of Type 2 diabetes and are early risk factors of AD. In particular, there is a higher risk of sporadic AD in patients with Type 2 diabetes and AD patients are more prone to Type 2 diabetes (Butler, Diabetes, 53:474-481, 2004.). Recently, it has also been proposed that AD should be reconsidered as Type 3 diabetes (de la Monte, J. Diabetes Sci. Technol., 2008; 2(6):1101-1113). Of special interest is the fact that AD and Type 2 diabetes share common pathogenic mechanisms and possibly treatments (Park S. A., J. Clin. Neurol., 2011; 7:10-18; Raffa, Br. J. Clin. Pharmacol 2011, 71(3):365-376). Elevated plasma levels of Aβ, the product of BACE activities, were recently associated with hyperglycemia and obesity in humans (see Meakin et al., Biochem J., 2012, 441(1):285-96; Martins, Journal of Alzheimer's Disease, 8 (2005) 269-282). Moreover, increased Aβ production prompts the onset of glucose intolerance and insulin resistance in mice (Cózar-Castellano, Am. J. Physiol. Endocrinol. Metab., 302:E1373-E1380, 2012; Delibegovic, Diabetologia (2011) 54:2143-2151). Finally, it is also suggested that circulating Aβ could participate in the development of atherosclerosis in both humans and mice (De Meyer, Atherosclerosis 216 (2011) 54-58; Catapano, Atherosclerosis 210 (2010) 78-87; Roher, Biochimica et Biophysica Acta 1812 (2011) 1508-1514).

Therefore, it is believed that BACE1 levels may play a critical role in glucose and lipid homoeostasis in conditions of chronic nutrient excess. Specifically, BACE1 inhibitors may be potentially useful for increasing insulin sensitivity in skeletal muscle and liver as illustrated by the fact that reduction in BACE1 decreases body weight, protects against diet-induced obesity and enhances insulin sensitivity in mice (see Meakin et al., Biochem. J. 2012, 441(1):285-96). Of equal interest is the identification of LRP1 as a BACE1 substrate and the potential link to atherosclerosis (Strickland, Physiol. Rev., 88: 887-918, 2008; Hyman, J. Biol. Chem., Vol. 280, No. 18, 17777-17785, 2005).

Likewise, inhibition of BACE2 is proposed as a treatment of Type 2 diabetes with the potential to preserve and restore β-cell mass and stimulate insulin secretion in pre-diabetic and diabetic patients (WO2011/020806). BACE2 is a β-cell enriched protease that regulates pancreatic β cell function and mass and is a close homologue of BACE1. Pharmacological inhibition of BACE2 increases β-cell mass and function, leading to the stabilization of Tmem27. (See Esterhazy et al., Cell Metabolism 2011, 14(3): 365-377). It is suggested that BACE2 inhibitors are useful in the treatment and/or prevention of diseases associated with the inhibition of BACE2 (e.g., Type 2 diabetes, with the potential to preserve and restore β-cell mass and stimulate insulin secretion in pre-diabetic and diabetic patients) (WO2011/020806).

Aminodihydrothiazine or thioamidine compounds are described in US2009/0082560, WO 2009/091016 and WO 2010/038686 as useful inhibitors of the β-secretase enzyme. Fused heterocyclic compounds useful as inhibitors of the β-secretase enzyme are also described in WO 2011071109 and corresponding US 2012245155. Co-pending PCT application, PCT/IB2012/054198, filed by Pfizer Inc on Aug. 17, 2012, also describes aminodihydrothiazine compounds that are useful inhibitors of the β-secretase enzyme. The present invention is directed to novel oxamidine compounds and their use in the treatment of neurodegenerative diseases, including AD, as well as the treatment of metabolic diseases and conditions such as diabetes and obesity.

SUMMARY OF THE INVENTION

A first embodiment of a first aspect of the present invention is a compound of Formula I

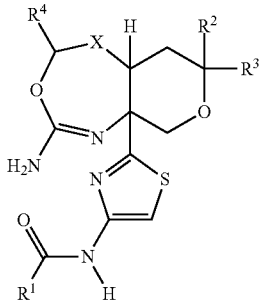

I wherein $R^1$ is a 5- to 6-membered heteroaryl, having one to four heteroatoms independently selected from N, O or S, wherein at least one of the heteroatoms is N and wherein said N is optionally substituted with $R^6$; and wherein said 5- to 6-membered heteroaryl is optionally substituted on carbon with one to three $R^5$; $R^2$ and $R^3$ are each independently selected from the group consisting of hydrogen, $C_{1-3}$alkyl, $C_{3-6}$cycloalkyl and 3- to 7-membered heterocycloalkyl; wherein the $C_{1-3}$alkyl is optionally and independently with one to three fluoro or $C_{1-3}$alkoxy, and the $C_{3-6}$cycloalkyl and 3- to 7-membered heterocycloalkyl are each optionally and independently substituted with one to three fluoro, $C_{1-3}$alkyl or $C_{1-3}$alkoxy; or $R^2$ and $R^3$ taken together with the carbon to which they are attached form a $C_{3-6}$ cycloalkyl ring or a 3- to 7-membered heterocycloalkyl, each of which is optionally and independently substituted with one to three fluoro, $C_{1-3}$alkyl or $C_{1-3}$alkoxy; $R^4$ is hydrogen or $C_{1-3}$alkyl optionally substituted with one to three fluoro; X is $CH_2$ or a bond; $R^5$ at each occurrence is independently selected from the group consisting of halo, hydroxy, cyano, $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl; wherein said $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; and $R^6$ is hydrogen or $C_{1-6}$alkyl; or a tautomer thereof or a pharmaceutically acceptable salt of said compound or tautomer.

Another embodiment of the present invention is a pharmaceutical composition comprising compounds of Formula I, or a tautomer thereof or a pharmaceutically acceptable salt of said compound or tautomer, and a pharmaceutically acceptable vehicle, diluent or carrier. The pharmaceutical compositions described herein can be used for inhibiting production of amyloid-β protein and for inhibiting beta-site amyloid precursor protein cleaving enzyme 1 (BACE1); for treating a neurodegenerative disease and, in particular, Alzheimer's disease; for inhibiting BACE1 and/or BACE2 activity for the therapeutic and/or prophylactic treatment of diseases and disorders characterized by elevated β-amyloid levels, including diabetes or Type 2 diabetes; for increasing insulin sensitivity in skeletal muscle and liver in a mammal, including humans; and for treating and/or preventing obesity.

The present invention is also directed to methods of treatment employing the compounds of Formula I such as:

(1) Methods of inhibiting BACE enzyme activity, by administering a therapeutically effective amount of an oxamidine or oxazepine compound of any of the embodiments of Formula I or a pharmaceutically acceptable salt thereof, and a pharmaceutically acceptable carrier, to a mammal or a patient in need thereof.

(2) Methods for treating conditions or diseases of the central nervous system and neurological disorders in which the β-secretase enzyme is involved (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment ("MCI"); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema), nerve injury treatment (including accelerating regeneration and recovery after peripheral nerve damage) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or pharmaceutically acceptable salt thereof. The compounds of Formula I may also be useful for improving memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress;

(3) Methods for treating a neurological disorder (such as migraine; epilepsy; Alzheimer's disease; Parkinson's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof;

(4) Methods for the treatment (e.g., delaying the progression or onset) of diabetes or diabetes-related disorders including Type 1 and Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy;

(5) Methods for the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on metabolic syndrome, see, e.g., Zimmet, P. Z. et al., "The Metabolic Syndrome: Perhaps an Etiologic Mystery but Far From a Myth—Where Does the International Diabetes Federation Stand?," Medscape Diabetes & Endocrinology, 7(2), (2005); and Alberti, K. G. et al., "The Metabolic Syndrome—A New Worldwide Definition," Lancet, 366, 1059-62 (2005); and (6) Methods for the treatment of nonalcoholic fatty liver disease (NAFLD) and hepatic insulin resistance;

The present invention is also directed to combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided;

All patents, patent applications and references referred to herein are hereby incorporated by reference in their entirety.

Other features and advantages of this invention will be apparent from this specification and the appendent claims which describe the invention. It is to be understood that both the foregoing and the following detailed description are exemplary only and are not restrictive of the invention as claimed.

DETAILED DESCRIPTION OF THE INVENTION

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

In this specification and in the claims that follow, reference will be made to a number of terms that shall be defined to have the following meanings:

As used herein, "eating disorders" refer to illnesses in which the patient suffers disturbances in his/her eating behaviors and related thoughts and emotions. Representative examples of obesity-related eating disorders include overeating, bulimia, binge-eating disorder, compulsive dieting, nocturnal sleep-related eating disorder, pica, Prader-Willi syndrome, and night-eating syndrome.

"Patient" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The term "alkyl" refers to a linear or branched-chain saturated hydrocarbyl substituent (i.e., a substituent obtained from a hydrocarbon by removal of a hydrogen); in one embodiment containing from one to six carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like.

The term "alkenyl" refers to a linear or branched-chain hydrocarbyl substituent (i.e., a substituent obtained from a hydrocarbon by removal of a hydrogen) which contains at least one carbon-carbon double bond; in one embodiment containing from three to six carbon atoms. Non-limiting examples of such substituents include allyl, propenyl, butenyl, isobutenyl, butadienyl, pentenyl, pentadienyl, hexenyl, hexadienyl and the like. The term "alkenyloxy" refers to an alkenyl group attached to an oxygen radical.

The term "alkynyl" refers to a linear or branched-chain hydrocarbyl substituent (i.e., a substituent obtained from a hydrocarbon by removal of a hydrogen) which contains at least one carbon-carbon triple bond; in one embodiment containing from three to six carbon atoms. Non-limiting examples of such substituents include propynyl, butynyl, isobutynyl, pentynyl, hexynyl and the like. The term "alkynyloxy" refers to an alkynyl group attached to an oxygen radical.

The term "alkylene" refers to an alkanediyl group (i.e. a substituent obtained from a hydrocarbon by removal of two hydrogens); in one embodiment containing from three to five carbons. Non-limiting examples of such groups include propylene, butylene and pentylene.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$cycloalkyl or $C_{3-6}$-cycloalkyl refers to saturated cycloalkyl group containing from 3 to 6 carbon ring atoms.

The term "cycloalkyl" refers to a carbocyclic substituent obtained by removing a hydrogen from a saturated carbocyclic molecule, for example one having three to six carbon atoms or having three to nine carbon atoms. The term "cycloalkyl" includes mono-, bi- and tricyclic saturated carbocycles, as well as bridged and fused ring carbocycles and also spiro-fused carbocyclic ring systems. The term "$C_{3-9}$cycloalkyl" means a radical of a three to nine membered ring system which includes the groups cyclopropyl, cyclobutyl, cyclopentyl, cyclohexyl, cycloheptyl, cyclooctyl, cyclononyl, bicyclopentyl, bicyclohexyl, bicycloheptyl, bicyclooctyl, bicyclononyl, spiropentyl, spirohexyl, spiroheptyl, spirooctyl and spirononyl. The term "$C_{3-6}$cycloalkyl" means a radical of a three to six membered ring system which includes the groups cyclopropyl, cyclobutyl, cyclopentyl, cyclohexyl, bicyclopentyl, bicyclohexyl, spiropentyl and spirohexyl. The term "$C_{3-6}$cycloalkoxy" refers to a three to six membered cycloalkyl group attached to an oxygen radical. Examples include cyclopropoxy, cyclobutoxy, cyclopentoxy and cyclohexoxy.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 6-membered heterocycloalkyl" refers to a heterocycloalkyl containing from 4 to 6 atoms, including one to three heteroatoms, in the cyclic moiety of the heterocycloalkyl. Likewise the phrase "5- to 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore the phases "5-membered heteroaryl" and "6-membered heteroaryl" refer to a five membered heteroaromatic ring system and a six membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring. In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2 (1H)-onyl, pyridazin-2(1H)-onyl, pyrimidin-2(1H)-onyl, pyrazin-2(1H)-onyl, imidazo[1,2-a]pyridinyl, and pyrazolo [1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), morpholinyl.

The term "heteroaryl" can also include, when specified as such, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydro-quinolinyl, 6,7-dihydro-5H-cyclopenta[b]pyridinyl, 6,7-dihydro-5H-cyclopenta[c]pyridinyl, 1,4,5,6-tetrahydro-cyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (—), a solid wedge (⬧), or a dotted wedge (⋯). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomenon of tautomerism; such tautomers are also regarded as compounds of the invention. For example, the compounds of Formula I may exist in several tautomeric forms, including the 2-amino-dihydrooxazine or 2-aminodihydrooxazepine form (when X is a bond or $CH_2$, respectively), I, and the 2-imino-tetrahydrooxazine or 2-imino-tetrahydrooxazepine form, I' (when X is a bond or $CH_2$, respectively). All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof. Examples of tautomers are described by the compounds of Formula I and I' and, collectively and generically, are referred to as compounds of Formula I.

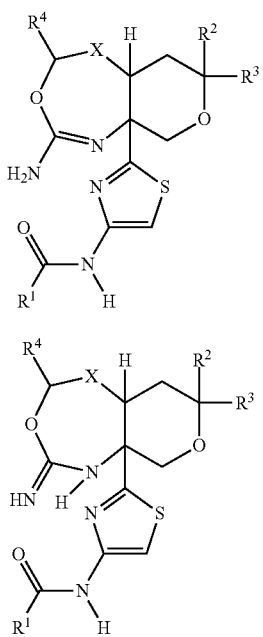

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include the lighter alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

A second embodiment of a first aspect of the present invention is the compound of the first embodiment of the first aspect of formula Ia

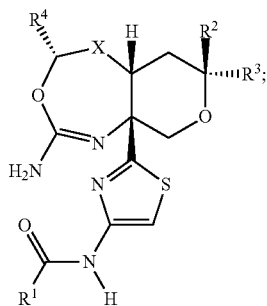

Ia or a tautomer thereof or a pharmaceutically acceptable salt of said compound or tautomer.

A third embodiment of a first aspect of the present invention is a compound of the first embodiment of the first aspect of formula Ib

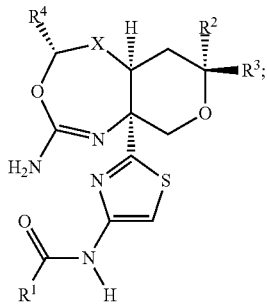

Ib or a tautomer thereof or a pharmaceutically acceptable salt of said compound or tautomer.

A fourth embodiment of a first aspect of the present invention is the compound of any one of the first through third embodiments of the first aspect wherein $R^2$ is hydrogen or methyl; $R^3$ is methyl, fluoromethyl, difluoromethyl or trifluoromethyl; and $R^4$ is hydrogen, fluoromethyl or trifluoromethyl; or a tautomer thereof or a pharmaceutically acceptable salt of said compound or tautomer.

A fifth embodiment of a first aspect of the present invention is the compound of the second embodiment of the first aspect wherein $R^2$ and $R^4$ are each hydrogen; $R^3$ is methyl; and X is $CH_2$; or a tautomer thereof or a pharmaceutically acceptable salt of said compound or tautomer.

A sixth embodiment of a first aspect of the present invention is the compound of the second embodiment of the first aspect wherein $R^2$ and $R^3$ are each methyl; $R^4$ is hydrogen; and X is a bond; or a tautomer thereof or a pharmaceutically acceptable salt of said compound or tautomer.

A seventh embodiment of a first aspect of the present invention is the compound of the second embodiment of the first aspect wherein $R^2$ is hydrogen; $R^3$ is methyl or trifluoromethyl; $R^4$ is hydrogen, fluoromethyl or trifluoromethyl; and X is a bond; or a tautomer thereof or a pharmaceutically acceptable salt of said compound or tautomer.

An eighth embodiment of a first aspect of the present invention is the compound of the second embodiment of the first aspect wherein $R^2$ and $R^3$ taken together with the carbon to which they are attached form a $C_{3-6}$cycloalkyl ring; $R^4$ is hydrogen; and X is a bond; or a tautomer thereof or a pharmaceutically acceptable salt of said compound or tautomer.

A ninth embodiment of a first aspect of the present invention is the compound of the eighth embodiment of the first aspect wherein $R^2$ and $R^3$ taken together with the carbon to which they are attached form a cyclobutyl ring; or a tautomer thereof or a pharmaceutically acceptable salt of said compound or tautomer.

A tenth embodiment of a first aspect of the present invention is the compound of the third embodiment of the first aspect wherein $R^2$ is hydrogen; $R^3$ is trifluoromethyl; $R^4$ is hydrogen; and X is a bond; or a tautomer thereof or a pharmaceutically acceptable salt of said compound or tautomer.

An eleventh embodiment of a first aspect of the present invention is the compound of any one of the fourth through tenth embodiments of the first aspect wherein $R^1$ is pyridinyl or pyrazinyl substituted with one or two $R^5$; and each $R^5$ is independently selected from chloro, cyano, methyl and difluoromethoxy; or a tautomer thereof or a pharmaceutically acceptable salt of said compound or tautomer.

A twelfth embodiment of a first aspect of the present invention is the compound of the eleventh embodiment of the first aspect wherein $R^1$ is 3-chloro-5-(difluoromethoxy)pyridin-2-yl, 5-chloropyridin-2-yl, 5-cyanopyridin-2-yl, 5-(difluoromethoxy)pyridin-2-yl, 5-(difluoromethoxy)-3-methylpyridin-2-yl or 5-(difluoromethoxy)pyrazin-2-yl; or a tautomer thereof or a pharmaceutically acceptable salt of said compound or tautomer.

A thirteenth embodiment of a first aspect of the present invention is the compound of the fifth embodiment of the first aspect selected from the group consisting of N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy) picolinamide; and N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy)-3-methylpicolinamide; or a tautomer thereof or a pharmaceutically acceptable salt of said compound or tautomer.

A fourteenth embodiment of a first aspect of the present invention is the compound of the sixth embodiment of the first aspect selected from the group consisting of N-(2-((4aR,8aR)-2-amino-6,6-dimethyl-4,4a,5,6-tetrahydropyrano[3,4-d][1,3]oxazin-8a(8H)-yl)thiazol-4-yl)-5-(difluoromethoxy)picolinamide; and N-(2-((4aR,8aR)-2-amino-6,
6-dimethyl-4,4a,5,6-tetrahydropyrano[3,4-d][1,3]oxazin-8a
(8H)-yl)thiazol-4-yl)-5-(difluoromethoxy)-3-
methylpicolinamide; or a tautomer thereof or a
pharmaceutically acceptable salt of said compound or tautomer.

A fifteenth embodiment of a first aspect of the present invention is the compound of the seventh embodiment of the first aspect selected from the group consisting of
N-(2-((4aR,6S,8aR)-2-amino-6-methyl-4,4a,5,6-tetrahydropyrano[3,4-d][1,3]oxazin-8a(8H)-yl)thiazol-4-yl)-5-(difluoromethoxy)picolinamide;
N-(2-((4aR,6S,8aR)-2-amino-6-methyl-4,4a,5,6-tetrahydropyrano[3,4-d][1,3]oxazin-8a(8H)-yl)thiazol-4-yl)-3-chloro-5-(difluoromethoxy)picolinamide;
N-(2-((4aR,6S,8aR)-2-amino-6-methyl-4,4a,5,6-tetrahydropyrano[3,4-d][1,3]oxazin-8a(8H)-yl)thiazol-4-yl)-5-(difluoromethoxy)-3-methylpicolinamide;
N-(2-((4S,4aR,6S,8aR)-2-amino-4-(fluoromethyl)-6-methyl-4,4a,5,6-tetrahydropyrano [3,4-d][1,3]oxazin-8a (8H)-yl)thiazol-4-yl)-5-(difluoromethoxy)picolinamide;
N-(2-((4S,4aR,6S,8aR)-2-amino-6-methyl-4-(trifluoromethyl)-4,4a,5,6-tetrahydropyrano [3,4-d][1,3]oxazin-8a (8H)-yl)thiazol-4-yl)-5-(difluoromethoxy)picolinamide;
N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-5-chloropicolinamide;
N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide;
N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-5-(difluoromethoxy)picolinamide; and
N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-3-chloro-5-(difluoromethoxy)picolinamide;
or a tautomer thereof or a pharmaceutically acceptable salt of said compound or tautomer.

A sixteenth embodiment of a first aspect of the present invention is the compound of the tenth embodiment of the first aspect selected from the group consisting of
N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-5-chloropicolinamide;
N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide;
N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-5-(difluoromethoxy)picolinamide; and
N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-3-chloro-5-(difluoromethoxy)picolinamide;
or a tautomer thereof or a pharmaceutically acceptable salt of said compound or tautomer.

The seventeenth embodiment of a first aspect of the present invention are the compounds of examples 14 through 19, respectively; or a tautomer thereof or a pharmaceutically acceptable salt of said compound or tautomer.

The eighteenth through twentieth embodiments of a first aspect of the present invention are the compounds of examples 3, 6 and 8, respectively; or a tautomer thereof or a pharmaceutically acceptable salt of said compound or tautomer.

A first embodiment of a second aspect of the present invention is a pharmaceutical composition comprising a therapeutically effective amount of a compound of any one of the first through twentieth embodiments of the first aspect of the present invention, or a tautomer thereof or a pharmaceutically acceptable salt of said compound or tautomer, and a pharmaceutically acceptable carrier.

Further embodiments of the present invention include methods of treatment employing the compounds of the present invention.

A first embodiment of a third aspect of the present invention is a method of inhibiting production of amyloid-β protein in a patient, the method comprising administering a therapeutically effective amount of a compound according to any one of the first through twentieth embodiments of the first aspect of the present invention, or a tautomer thereof or a pharmaceutically acceptable salt of said compound or tautomer, to a patient in need of inhibition of production of amyloid-β protein.

A second embodiment of a third aspect of the present invention is a method of inhibiting beta-site amyloid precursor protein cleaving enzyme 1 (BACE1) in a patient, the method comprising administering a therapeutically effective amount of a compound according to any one of the first through twentieth embodiments of the first aspect of the present invention, or a tautomer thereof or a pharmaceutically acceptable salt of said compound or tautomer, to a patient in need of inhibition of beta-site amyloid precursor protein cleaving enzyme 1 (BACE1).

A third embodiment of a third aspect of the present invention is a method for treating a neurodegenerative disease in a patient, the method comprising administering a therapeutically effective amount of a compound according to any one of the first through twentieth embodiments of the first aspect of the present invention, or a tautomer thereof or a pharmaceutically acceptable salt of said compound or tautomer, to a patient in need of treatment thereof.

A fourth embodiment of a third aspect of the present invention is the method of the third embodiment of the third aspect of the present invention wherein the neurodegenerative disease is Alzheimer's disease.

A fifth embodiment of a third aspect of the present invention is a method of treating or preventing diabetes in a patient, the method comprising administering a therapeutically effective amount of a compound according to any one of the first through twentieth embodiments of the present invention, or a tautomer thereof or a pharmaceutically acceptable salt of said compound or tautomer, to a patient in need of treatment or prevention thereof.

A sixth embodiment of a third aspect of the present invention is the method of the fifth embodiment of the third aspect of the present invention wherein the diabetes is Type 2 diabetes.

Further embodiments of the present invention include the use of a compound according to any one of first through twentieth embodiments of the first aspect of the present invention in the preparation of a medicament useful for treating the conditions, diseases and disorders as described herein.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3$^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a BACE inhibitor compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, without limitation:

(i) anti-obesity agents (including appetite suppressants), include gut-selective MTP inhibitors (e.g., dirlotapide, mitratapide and implitapide, CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonists (e.g., compounds described in U.S. Pat. No. 6,818,658), lipase inhibitors (e.g., Cetilistat), PYY$_{3-36}$ (as used herein "PYY$_{3-36}$" includes analogs, such as peglated PYY$_{3-36}$, e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine.

(ii) anti-diabetic agents, such as an acetyl-CoA carboxylase (ACC) inhibitor as described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a monoacylglycerol O-acyltransferase inhibitor, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPAR γ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S. et al., *Drug Discovery Today*, 12(9/10), 373-381 (2007)), a SIRT-1 inhibitor (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secretagogue, a fatty acid oxidation inhibitor, an A2 antagonist, a c-jun amino-terminal kinase (JNK) inhibitor, a glucokinase activator (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g., GSK1362885), a VPAC2 receptor agonist, an SGLT2 inhibitor, such as those described in E. C. Chao et al., Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al., Annual Reports in Medicinal Chemistry 2008, 43, 119-137, a GPR119 modulator, particularly an agonist, such as those described in WO2010140092, WO2010128425, WO2010128414, WO2010106457, Jones, R. M. et al., in Medicinal Chemistry 2009, 44, 149-170 (e.g., MBX-2982, GSK1292263, APD597 and PSN821), an FGF21 derivative or an analog such as those described in Kharitonenkov, A. et al., Current Opinion in Investigational Drugs 2009, 10(4), 359-364, TGR5 (also termed GPBAR1) receptor modulators, particularly agonists, such as those described in Zhong, M., Current Topics in Medicinal Chemistry, 2010, 10(4), 386-396 and INT777, a GPR40 agonist, such as those described in Medina, J. C., Annual Reports in Medicinal Chemistry, 2008, 43, 75-85, including but not limited to TAK-875, a GPR120 modulator, particularly an agonist, a high-affinity nicotinic acid receptor (HM74A) activator, and an SGLT1 inhibitor, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors (e.g., SSTR1, SSTR2, SSTR3 and SSTR5), inhibitors or modulators of PDHK2 or PDHK4, inhibitors of MAP4K4, modulators of IL1 family including IL1beta, and modulators of RXRalpha. In addition, suitable anti-diabetic agents include mechanisms listed by Carpino, P. A., Goodwin, B. Expert Opin. Ther. Pat, 2010, 20(12), 1627-51;

(iii) anti-hyperglycemic agents, for example, those described at page 31, line 31 through page 32, line 18 of WO 2011005611;

(iv) lipid lowering agents (for example, those described at page 30, line 20 through page 31, line 30 of WO 2011005611), and anti-hypertensive agents (for example, those described at page 31, line 31 through page 32, line 18 of WO 2011005611);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-ß (or fragments thereof), such as Aß$_{1-15}$ conjugated to pan HLA DR-binding epitope (PADRE®), ACC-001 (Elan/Wyeth), and Affitope;

(vii) antibodies to amyloid-ß (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO006/036291, WO006/069081, WO006/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate (KIACTA®), celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the *gingko biloba* extract EGb-761 (ROKAN®, TEBONIN®), tramiprosate (CEREBRIL®, ALZHEMED®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, and GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors;

central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xiii) phosphodiesterase (PDE) inhibitors, including (a) PDE1 inhibitors (b) PDE2 inhibitors (c) PDE3 inhibitors (d) PDE4 inhibitors (e) PDE5 inhibitors (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl)quinoline (PF-2545920);

(xiv) serotonin (5-hydroxytryptamine) 1A (5-HT$_{1A}$) receptor antagonists, such as spiperone, levo-pindolol, lecozotan;

(xv) serotonin (5-hydroxytryptamine) 2C (5-HT$_{2C}$) receptor agonists, such as vabicaserin, and zicronapine; serotonin (5-hydroxytryptamine) 4 (5-HT$_4$) receptor agonists/antagonists, such as PRX-03140 (Epix) and PF-04995274;

(xvi) serotonin (5-hydroxytryptamine) 3C (5-HT$_{3C}$) receptor antagonists, such as Ondansetron (Zofran);

(xvii) serotonin (5-hydroxytryptamine) 6 (5-HT$_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xviii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xix) Glycine transporter-1 inhibitors such as paliflutine, ORG-25935, and ORG-26041; and mGluR modulators such as AFQ-059 and amantidine;

(xx) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xxi) P450 inhibitors, such as ritonavir;

(xxii) tau therapy targets, such as davunetide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

GENERAL SYNTHETIC SCHEMES

Compounds of the invention, including salts of the compounds or N-oxides, can be prepared using known organic synthesis techniques and can be synthesized according to any of numerous possible synthetic routes.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin layer chromatography (TLC).

Compounds of Formula I and intermediates thereof may be prepared according to the following reaction schemes and accompanying discussion. Unless otherwise indicated, R$^1$, R$^2$, R$^3$, R$^4$, X and structural Formula I in the reaction schemes and discussion that follow are as defined above. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

In the following description of the general reaction schemes and in the experimental procedures which follow the following abbreviations may have been used.

ABBREVIATIONS

DMB=dimethoxybenzylamine, Bz=benzoyl, Boc=t-butoxycarbonyl, 9-BBN=9-borabicyclo[3.3.1]nonane, $BF_3OEt_2$=boron trifluoride etherate; $CDCl_3$=deutero-chloroform; $CD_3OD$=deutero-methanol; DBU=1,8-diazabicyclo [5.4.0] undec-7-ene; DCM=dichloromethane; EDC or EDCl=1-ethyl-3-(3-dimethylaminopropyl)carbodiimide hydrochloride; EtOAc=ethyl acetate; EtOH=ethanol; g=gram; h=hour; HATU=2-(7-aza-1H-benzotriazole-1-yl)-1,1,3,3-tetramethyluronium hexafluorophosphate; $H_2O$=water; HPLC=high-performance liquid chromatography; $K_2CO_3$=potassium carbonate; KF=potassium fluoride; L=liter; LCMS=liquid chromatography mass spectroscopy; M=molar; MeOH=methanol; mg=milligram; MHz=megahertz; min=minute; μL=microliter; mL=milliliter, mmol=millimole; $Mo(CO)_6$=molybdenum hexacarbonyl; mol=mole; N=normal; $N_2$=nitrogen; NaH=sodium hydride; n-BuLi=n-butyllithium; $NH_4Cl$=ammonium chloride; $NaHCO_3$=sodium bicarbonate; NaOCl=sodium hypochlorite; NaOH=sodium hydroxide; NaOtBu=sodium tert-butoxide; $Na_2SO_4$=sodium sulfate; NMR=nuclear magnetic resonance; $Pd_2(dba)_3$=tris (dibenzylideneacetone)dipalladium(0); PSI=pounds per square inch; rt=room temperature; TBAF=tetrabutyl ammonium fluoride; t-ButylXPhos=2-di-tert-butylphosphino-2',4', 6'-triisopropylbiphenyl; TEA=triethylamine; TEA 3HF=triethylamine trihydrofluoride; TFA=trifluoroacetic acid; THF=tetrahydrofuran; TLC=thin layer chromatography; T3P=propane phosphonic acid anhydride. The term Celite as used herein refers to a brand of diatomaceous earth that can be used for filtrations. Celite® is available from Imerys Filtration Minerals Inc., San Jose, Calif., USA.

In Schemes 1-5 certain of the intermediates and compounds are depicted with specified stereochemistry. It is to be understood that that the reactions shown in the Schemes can also be carried out with the corresponding racemic materials or with corresponding chiral materials where the stereochemistry is the opposite of that depicted below.

Scheme 1

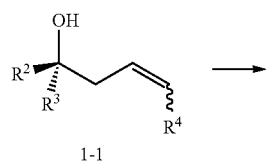

1-1

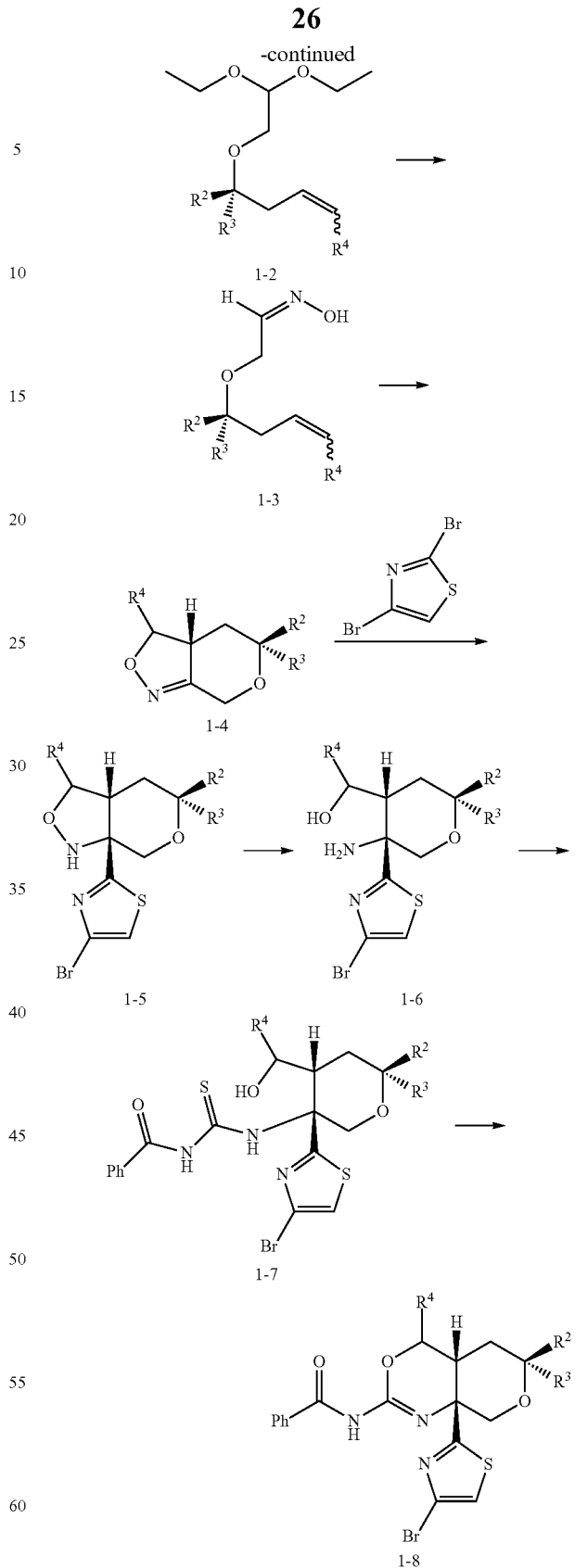

Scheme 1 refers to preparation of an intermediate of Formula 1-8. Referring to Scheme 1, alcohols of Formula 1-1 wherein $R^2$, $R^3$ and $R^4$ are described above are either commercially available or can be obtained by the methods well known in the art. A compound of Formula 1-2 can be prepared via alkylation of an alcohol of Formula 1-1 with 2-bromo-1,1-diethoxyethane in the presence of a suitable base, such as sodium hydride and in a suitable solvent, such as tetrahydrofuran (THF). A compound of Formula 1-3 can be prepared by treating a compound of Formula 1-2 with a suitable acid, such as aqueous hydrochloric acid, to form an aldehyde in situ, followed by condensation with hydroxylamine hydrochloride in the presence of a suitable base, such as sodium acetate. A compound of Formula 1-3 can then be converted to an isoxazoline of Formula 1-4 via [3+2] cycloaddition in the presence of a suitable oxidant, such as sodium hypochlorite, and a suitable base, such as triethylamine in a suitable solvent, such as dichloromethane. A compound of Formula 1-5 can be obtained by the nucleophilic addition of a thiazole lithium species that can be generated in situ by treating 2,4-dibromo-1,3-thiazole with a suitable alkyl lithium reagent, such as n-butyllithium, in the presence of a suitable Lewis acid, such as boron trifluoride diethyl etherate, and in a suitable solvent, such as a mixed solvent of toluene/tetrahydrofuran (10/1) at low temperature. A compound of Formula 1-6 can then be obtained by reductive cleavage of the N—O bond promoted by molybdenum hexacarbonyl [Mo(CO)$_6$] in the presence of a suitable reducing agent, such as sodium borohydride (NaBH$_4$). A compound of Formula 1-6 can be treated with benzoyl isothiocyanate in a suitable solvent, such as dichloromethane, to yield an intermediate of Formula 1-7, which upon activation via alkylation with a suitable reagent, such as methyl iodide (MeI), in the presence of a suitable base, such as potassium carbonate (K$_2$CO$_3$), can be cyclized to yield the desired intermediate of Formula 1-8. Alternatively, a compound of Formula 1-7 can be converted to a compound of Formula 1-8 by 1-ethyl-3-(3-dimethylaminopropyl)carbodiimide hydrochloride (EDCl), in the presence of a suitable solvent, such as dichloromethane.

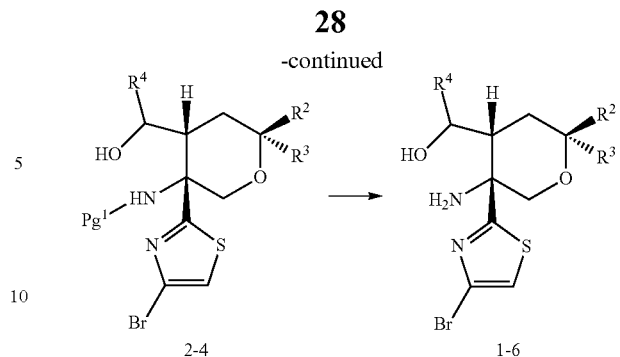

2-4    1-6

Scheme 2 refers to an alternative preparation of an intermediate of Formula 1-6. Referring to Scheme 2, a compound of Formula 2-1 can be prepared by the procedure for the preparation of intermediate 1-6 described in Scheme 1, wherein R$^4$ is H. The amino group of a compound of Formula 2-1 can be protected by an appropriate protecting group (Pg$^1$), such as carboxybenzyl (CBZ), to give a compound of Formula 2-2. The alcohol moiety of a compound of Formula 2-2 can then be oxidized to an aldehyde using methods well known in the art, such as Dess-Martin oxidation, to give a compound of Formula 2-3. A compound of Formula 2-4 can then be generated by nucleophilic addition of an R$^4$ carbanion to an aldehyde of Formula 2-3. A representative procedure to generate R$^4$ carbanion is to treat R$^4$ trimethylsilyl reagent with tetrabutylammonium fluoride (TBAF) in a suitable solvent, such as tetrahydrofuran. The protecting group Pg$^1$ of a compound of Formula 2-4 can then be removed to give the desired intermediate of Formula 1-6 using methods well known in the art. For example, when Pg$^1$ is CBZ, it can be removed by treatment with a suitable acid, such as triflic acid.

Scheme 2

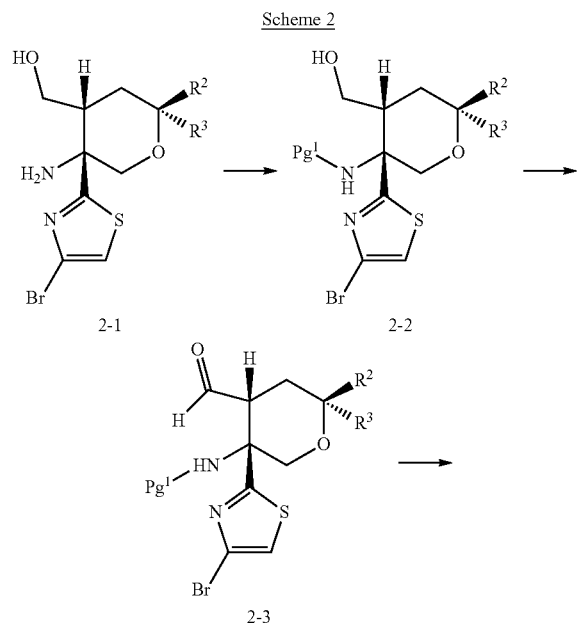

Scheme 3

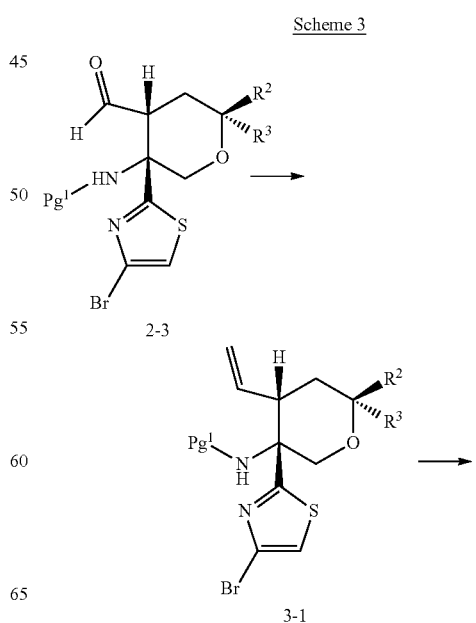

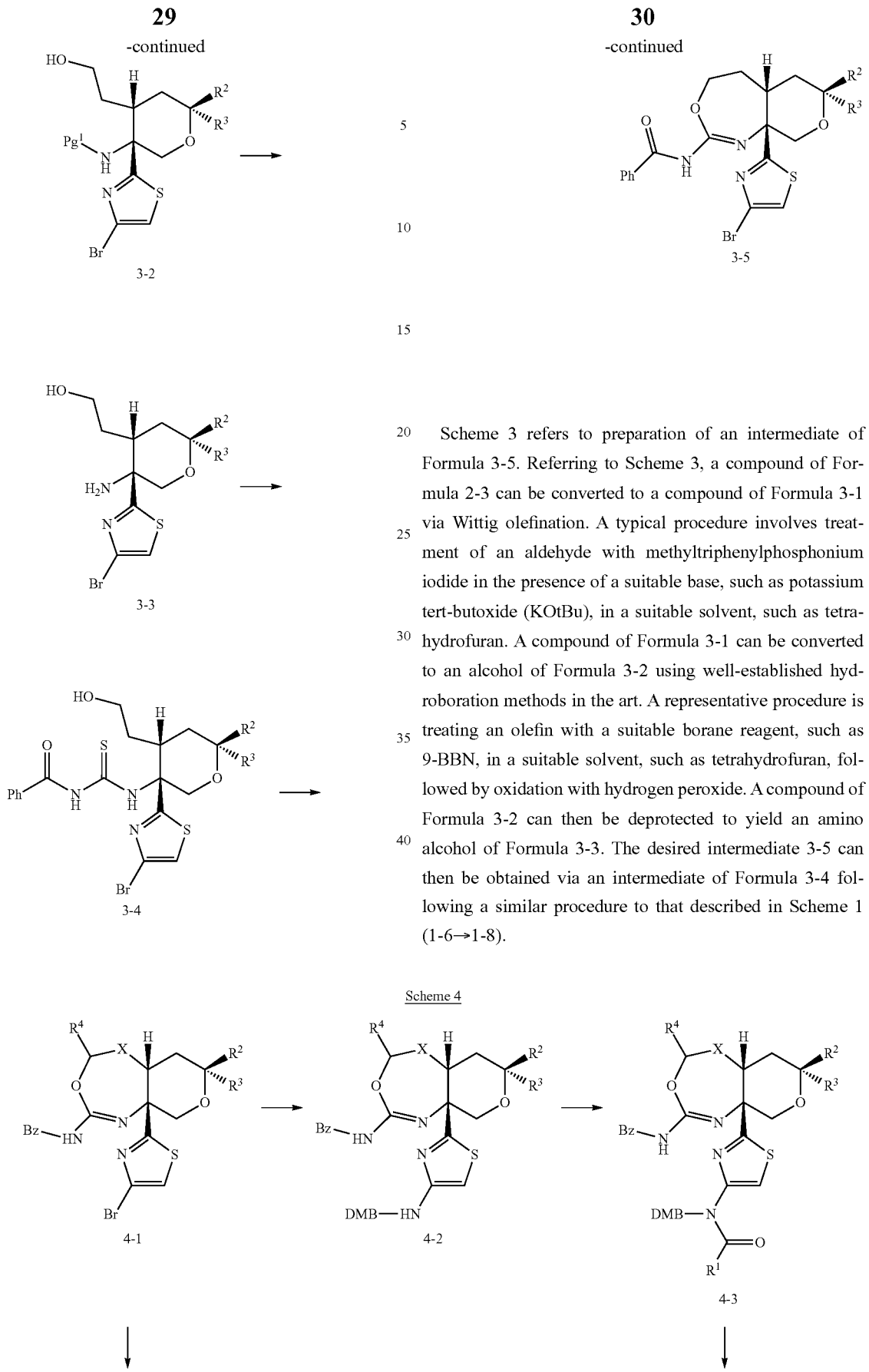

Scheme 3 refers to preparation of an intermediate of Formula 3-5. Referring to Scheme 3, a compound of Formula 2-3 can be converted to a compound of Formula 3-1 via Wittig olefination. A typical procedure involves treatment of an aldehyde with methyltriphenylphosphonium iodide in the presence of a suitable base, such as potassium tert-butoxide (KOtBu), in a suitable solvent, such as tetrahydrofuran. A compound of Formula 3-1 can be converted to an alcohol of Formula 3-2 using well-established hydroboration methods in the art. A representative procedure is treating an olefin with a suitable borane reagent, such as 9-BBN, in a suitable solvent, such as tetrahydrofuran, followed by oxidation with hydrogen peroxide. A compound of Formula 3-2 can then be deprotected to yield an amino alcohol of Formula 3-3. The desired intermediate 3-5 can then be obtained via an intermediate of Formula 3-4 following a similar procedure to that described in Scheme 1 (1-6→1-8).

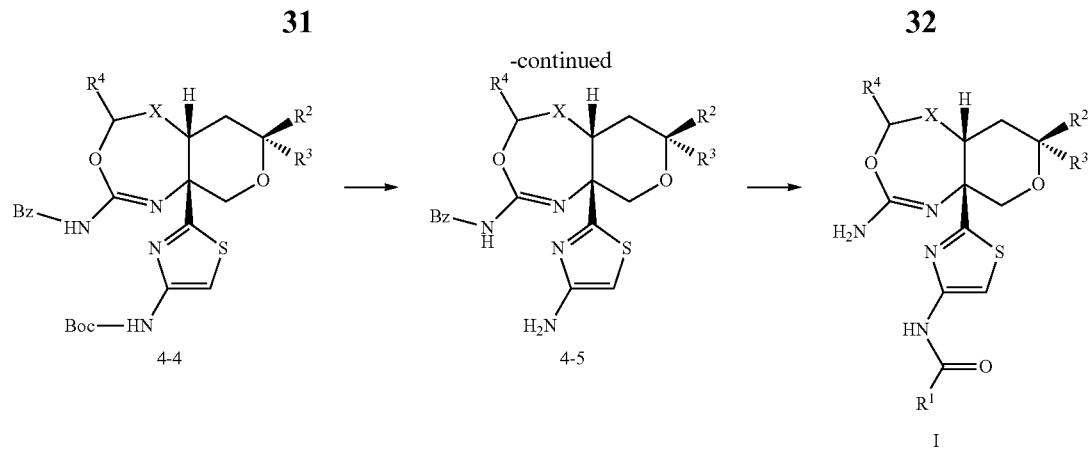

Scheme 4 refers to preparation of a compound within Formula I with the stereochemistry as depicted. Referring to Scheme 4, compounds of Formula 4-1 wherein $R^2$, $R^3$, $R^4$ and X are described above can be obtained by the methods described in Schemes 1-3. A compound of Formula 4-1 can be converted to a compound of Formula 4-2 via amidation with 2,4-dimethoxybenzylamine, in the presence of a suitable metal catalyst, such as tris(dibenzylideneacetone)dipalladium(0) ($Pd_2dba_3$), a suitable ligand, such as 2-di-tert-butylphosphino-2',4',6'-triisopropylbiphenyl (tBuXphos), and a suitable base, such as sodium tert-butoxide, in a suitable solvent, such as 1,4-dioxane. A compound of Formula 4-3 can be then obtained by amide formation with $R^1CO_2H$ using a suitable coupling reagent, such as propylphosphonic anhydride (T$_3$P®), and a suitable base, such as triethylamine. A compound of Formula I can then be obtained by removal of the 2,4-dimethoxybenzyl group (DMB) by treatment with a suitable acid, such as trifluoroacetic acid, in a suitable solvent, such as dichloromethane, and subsequent removal of the benzoyl protecting group (Bz) by a suitable reagent, such as DBU or methoxylamine hydrochloride/pyridine, in a suitable solvent, such as methanol or ethanol. Alternatively, a compound of Formula 4-1 can be converted to a compound of Formula 4-4 via amidation with tert-butyl carbamate, in the presence of a suitable metal catalyst, such as tris(dibenzylideneacetone)dipalladium(0) ($Pd_2dba_3$), a suitable ligand, such as di-tert-butyl [2',4',6'-tri(propan-2-yl)biphenyl-2-yl]phosphane, and a suitable base, such as potassium phosphate, in a suitable solvent, such as toluene. The Boc protecting group can be removed by a suitable acid, such as trifluoroacetic acid, to yield a compound of Formula 4-5. A compound within Formula I (with the stereochemistry as depicted) can then be obtained via amide formation with $R^1CO_2H$ using a suitable coupling reagent, such as N-[(dimethylamino)-1H-1,2,3-triazolo-[4,5-b]pyridin-1-ylmethylene]-N-methylmethanaminium hexafluorophosphate N-oxide (HATU®), and a suitable base, such as triethylamine, in a suitable solvent, such as dichloromethane, followed by removal of the benzoyl protecting group using a suitable reagent, such as DBU or methoxylamine hydrochloride/pyridine, in a suitable solvent, such as methanol or ethanol.

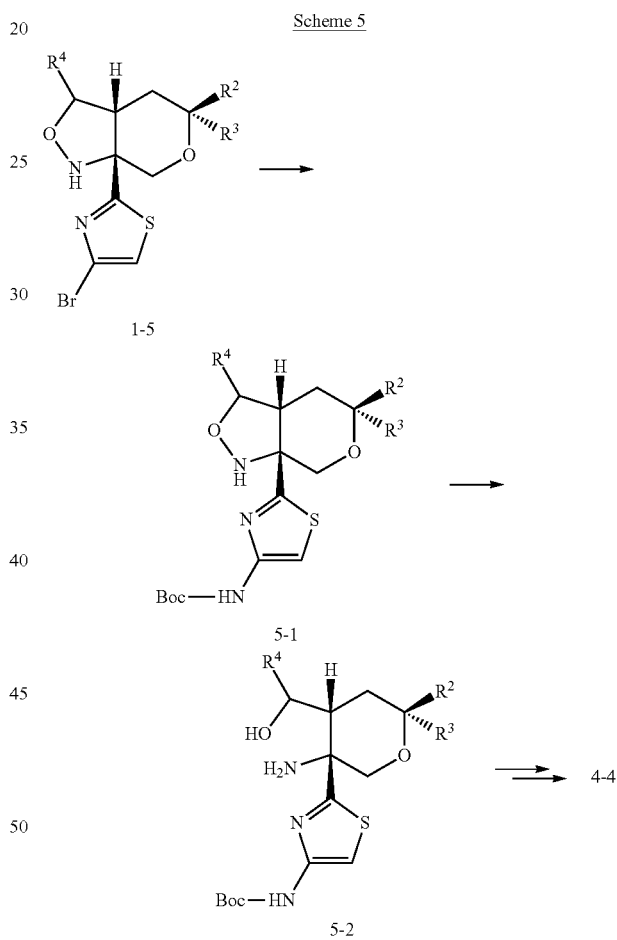

Scheme 5 refers to an alternative preparation of intermediates of Formula 4-4. Referring to Scheme 5, a compound of Formula 1-5 can be converted to a compound of Formula 5-1 via amidation with tert-butyl carbamate, in the presence of a suitable metal catalyst, such as tris(dibenzylideneacetone)dipalladium(0) ($Pd_2dba_3$), a suitable ligand, such as di-tert-butyl[2',4',6'-tri(propan-2-yl)biphenyl-2-yl]phosphane, and a suitable base, such as potassium phosphate, in a suitable solvent, such as toluene. The N—O bond of a compound of Formula 5-1 can then be cleaved by hydrogenation in the presence of a suitable catalyst, such as Raney nickel in a suitable solvent such as isopropanol and tetrahydrofuran, to yield a compound of Formula 5-2, which can then be converted to intermediate 4-4 using the method described in described in Scheme 1 (1-6→1-8).

Additional starting materials and intermediates useful for making the compounds of the present invention can be obtained from chemical vendors such as Sigma-Aldrich or can be made according to methods described in the chemical art.

Those skilled in the art can recognize that in all of the Schemes described herein, if there are functional (reactive) groups present on a part of the compound structure such as a substituent group, for example $R^1$, $R^2$, $R^3$, $R^4$, X, etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion ($CN^-$). For another example, an —S— can be oxidized to —S(═O)— and/or —S(═O)$_2$—. For yet another example, an unsaturated bond such as C═C or C≡C can be reduced to a saturated bond by hydrogenation. In some embodiments, a primary amine or a secondary amine moiety (present on a substituent group such as $R^1$ etc.) can be converted to an amide, sulfonamide, urea, or thiourea moiety by reacting it with an appropriate reagent such as an acid chloride, a sulfonyl chloride, an isocyanate, or a thioisocyanate compound. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^1$, $R^2$, $R^3$, $R^4$, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an $NH_2$ group can be protected by a benzyloxycarbonyl (Cbz) or Boc group; conversion back to the $NH_2$ group can be carried out at a later stage of the synthetic process via deprotection.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well known to those of ordinary skill in the art.

EXPERIMENTAL PROCEDURES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents.

For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate Rfs or retention times. All starting materials in these Preparations and Examples are either commercially available or can be prepared by methods known in the art or as described herein.

Preparation P1: (3aR,5S)-5-Methyl-3,3a,4,5-tetrahydro-7H-pyrano[3,4-c][1,2]oxazole (P1)

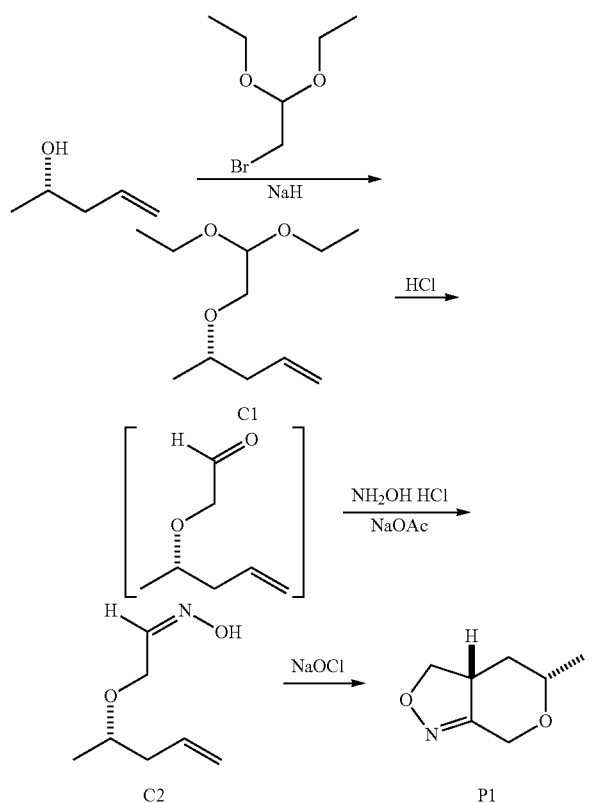

Step 1: Synthesis of (4S)-4-(2,2-diethoxyethoxy)pent-1-ene (C1)

To a suspension of sodium hydride (60% in mineral oil, 13.9 g, 0.348 mol) in tetrahydrofuran (350 mL) was added a solution of (S)-pent-4-en-2-ol (10.0 g, 0.116 mol) in tetrahydrofuran (50 mL) at 0° C. The reaction was warmed to room temperature and stirred for 30 minutes, whereupon 2-bromo-1,1-diethoxyethane (68.6 g, 0.348 mol) was added and the reaction mixture was heated to reflux for 18 hours. The reaction mixture was then cooled to 0° C., quenched with water (50 mL), and partitioned between ethyl acetate (300 mL) and water (200 mL). The organic layer was washed with saturated aqueous sodium chloride solution (2×100 mL), dried, and concentrated in vacuo. Silica gel chromatography (Eluent: 30:1 petroleum ether/ethyl acetate) provided the product as a yellow oil. Yield: 17.4 g, 86.0 mmol, 74%. $^1$H NMR (400 MHz, CDCl$_3$), δ 5.76-5.85 (m, 1H), 5.02-5.09 (m, 2H), 4.58-4.60 (m, 1H), 3.66-3.74 (m, 2H), 3.43-3.61 (m, 5H), 2.29-2.36 (m, 1H), 2.13-2.20 (m, 1H), 1.21 (t, J=7.2 Hz, 6H), 1.14 (d, J=6.4 Hz, 3H).

Step 2: Synthesis of N-hydroxy-2-[(2S)-pent-4-en-2-yloxy]ethanimine (C2)

To a solution of C1 (17.4 g, 86.0 mmol) in tetrahydrofuran (100 mL) was added aqueous hydrochloric acid (2 M, 51.0 mL, 0.102 mol), and the reaction mixture was heated to 75° C. for 1 hour. After removal of solvent in vacuo, ethanol (100 mL) and water (20 mL) were added, followed by sodium acetate (35.17 g, 0.429 mol) and hydroxylamine hydrochloride (17.9 g, 0.257 mol). The reaction mixture was stirred at 60° C. for 18 hours, whereupon it was concentrated in vacuo; the residue was then partitioned between water and dichloromethane. The aqueous layer was extracted with dichloromethane (3×200 mL) and the combined organic layers were dried over sodium sulfate, filtered, and concentrated under reduced pressure. Silica gel chromatography (Eluent: 10:1 petroleum ether/ethyl acetate) provided the product as a yellow oil, which was used without further purification in the subsequent step. Yield: 8.6 g, 60 mmol, 70%.

Step 3: Synthesis of (3aR,5S)-5-methyl-3,3a,4,5-tetrahydro-7H-pyrano[3,4-c][1,2]oxazole (P1)

To a solution of C2 (8.6 g, 60 mmol) and triethylamine (0.455 g, 4.50 mmol) in dichloromethane (150 mL) at room temperature was slowly added an aqueous solution of sodium hypochlorite (6%, 90 mL), at a rate that maintained the internal reaction temperature between 20° C. and 25° C. After completion of the addition, the organic layer was dried, filtered, and concentrated in vacuo. Silica gel chromatography (Eluent: 10:1 petroleum ether/ethyl acetate) provided the product as a yellow oil. Yield: 5.70 g, 40.4 mmol, 67%. LCMS m/z 142.1 [M+H]$^+$, $^1$H NMR (400 MHz, CDCl$_3$), δ 4.68 (d, J=13.2 Hz, 1H), 4.59 (dd, J=10, 8 Hz, 1H), 4.18 (d, J=13.2 Hz, 1H), 3.76 (dd, J=12, 8 Hz, 1H), 3.59-3.66 (m, 1H), 3.39-3.50 (m, 1H), 2.14-2.19 (m, 1H), 1.42-1.51 (m, 1H), 1.25 (d, J=6 Hz, 3H).

Preparation P2: N-{[(3R,4R,6S)-3-(4-bromo-1,3-thiazol-2-yl)-4-(hydroxymethyl)-6-methyltetrahydro-2H-pyran-3-yl]carbamothioyl}benzamide (C6)

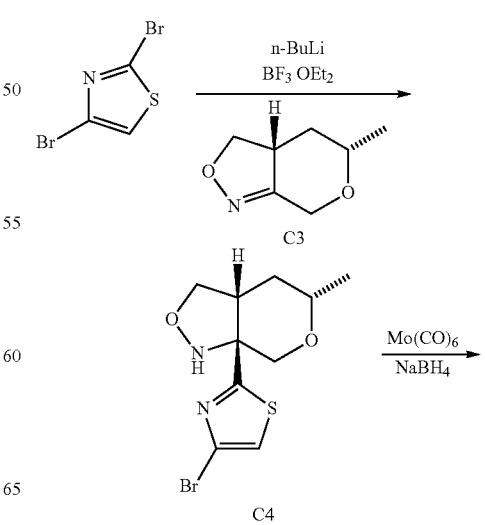

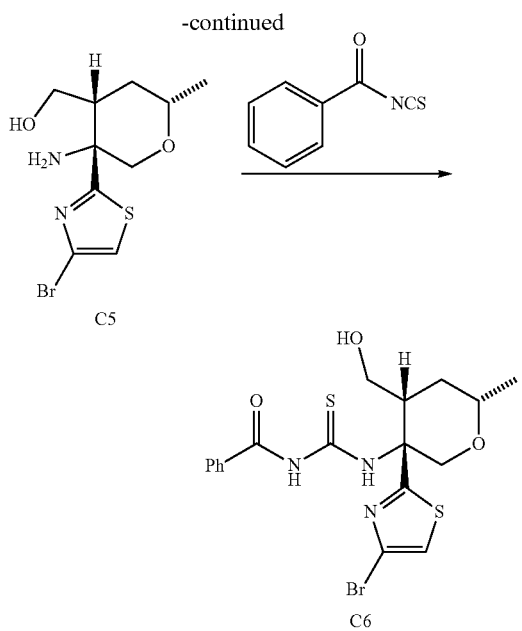

Step 1: Synthesis of (3aR,5S,7aR)-7a-(4-bromo-1,3-thiazol-2-yl)-5-methylhexahydro-1H-pyrano[3,4-c][1,2]oxazole (C4)

2,4-Dibromo-1,3-thiazole (44.7 g, 184 mmol) was dissolved in a mixture of toluene and tetrahydrofuran (10:1, 900 mL) and cooled to −78° C. To this solution was added boron trifluoride diethyl etherate (21.9 mL, 177 mmol), followed by drop-wise addition of n-butyllithium (2.5 M solution in hexanes, 68.0 mL, 170 mmol), and the reaction mixture was stirred for 30 minutes. A solution of C3 (20 g, 140 mmol) in a mixture of toluene and tetrahydrofuran (10:1, 22 mL) was then added drop-wise; the reaction temperature was maintained below −72° C. during the course of both additions. Stirring was continued for 1 hour at −78° C., whereupon the reaction was quenched via addition of saturated aqueous ammonium chloride solution. The aqueous layer was extracted three times with ethyl acetate, and the combined organic layers were washed with water and with saturated aqueous sodium chloride solution, dried over sodium sulfate, filtered, and concentrated in vacuo. Silica gel chromatography (Gradient: 0% to 100% ethyl acetate in heptane) afforded the product as a tacky amber oil. Yield: 36.34 g, 119.1 mmol, 85%. LCMS m/z 305.0, 307.0 [M+H]$^+$. $^1$H NMR (400 MHz, CDCl$_3$) δ 7.22 (s, 1H), 3.97 (AB quartet, upfield doublet is broadened, $J_{AB}$=12.6 Hz, $\Delta v_{AB}$=13.4 Hz, 2H), 3.67-3.76 (m, 3H), 3.38 (br ddd, J=11.8, 6.9, 4.6 Hz, 1H), 1.90 (ddd, J=14.1, 6.9, 2.1 Hz, 1H), 1.42 (ddd, J=14.1, 11.7, 11.7 Hz, 1H), 1.27 (d, J=6.2 Hz, 3H).

Step 2: Synthesis of [(2S,4R,5R)-5-amino-5-(4-bromo-1,3-thiazol-2-yl)-2-methyltetrahydro-2H-pyran-4-yl]methanol (C5)

Molybdenum hexacarbonyl (98%, 6.67 g, 24.8 mmol) was added to a solution of C4 (15.12 g, 49.54 mmol) in a mixture of acetonitrile (390 mL) and water (20 mL), and the reaction mixture was heated at reflux for 1 hour. After cooling to room temperature, the reaction mixture was chilled in an ice bath, treated portion-wise with sodium borohydride (7.50 g, 198 mmol), and allowed to stir at 0° C. for 1 hour. The mixture was then filtered through a pad of diatomaceous earth, and the pad was washed three times with dichloromethane; the organic portion of the combined filtrate and washes was washed with saturated aqueous sodium chloride solution, dried over sodium sulfate, filtered, and concentrated in vacuo. Methanol was added to the residue, then removed via concentration under reduced pressure. This methanol treatment was repeated, and the resulting residue was dissolved in dichloromethane, washed twice with 1 M aqueous sodium hydroxide solution, washed once with saturated aqueous sodium chloride solution and concentrated in vacuo, affording the product as a brown solid. Yield: 14.48 g, 47.13 mmol, 95%. LCMS m/z 307.0, 309.0 [M+H]$^+$. $^1$H NMR (400 MHz, CDCl$_3$) δ 7.22 (s, 1H), 3.79 (d, half of AB quartet, J=11.5 Hz, 1H), 3.64-3.75 (m, 3H), 3.54 (dd, half of ABX pattern, J=11.5, 4.1 Hz, 1H), 2.46-2.54 (m, 1H), 1.82-1.94 (m, 1H), 1.67-1.74 (m, 1H), 1.32 (d, J=6.2 Hz, 3H).

Step 3: Synthesis of N-{[(3R,4R,6S)-3-(4-bromo-1,3-thiazol-2-yl)-4-(hydroxymethyl)-6-methyltetrahydro-2H-pyran-3-yl]carbamothioyl}benzamide (C6)

Benzoyl isothiocyanate (6.92 g, 42.4 mmol) was added in a drop-wise manner to a solution of C5 (14.48 g, 47.13 mmol) in dichloromethane (420 mL), and the reaction mixture was stirred at room temperature for 24 hours. Volatiles were removed in vacuo, and the residue was purified via silica gel chromatography (Gradient: 0% to 50% ethyl acetate in heptane), providing the product as a yellow solid. Yield: 14.7 g, 31.2 mmol, 66%. $^1$H NMR (400 MHz, CDCl$_3$) δ 11.70 (br s, 1H), 8.93 (br s, 1H), 7.86-7.90 (m, 2H), 7.62-7.67 (m, 1H), 7.51-7.56 (m, 2H), 7.25 (s, 1H), 5.47 (d, J=11.9 Hz, 1H), 3.91 (d, J=12.0 Hz, 1H), 3.83 (d, J=4.4 Hz, 2H), 3.74-3.81 (m, 1H), 2.44-2.52 (m, 1H), 1.80-1.87 (m, 2H), 1.33 (d, J=6.2 Hz, 3H).

Example 1

N-(2-((4aR,6S,8aR)-2-amino-6-methyl-4,4a,5,6-tetrahydropyrano[3,4-d][1,3]oxazin-8a(8H)-yl)thiazol-4-yl)-5-(difluoromethoxy)picolinamide (1)

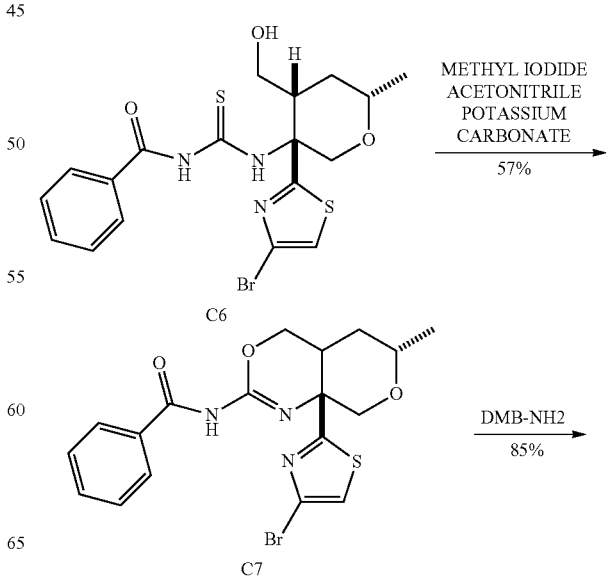

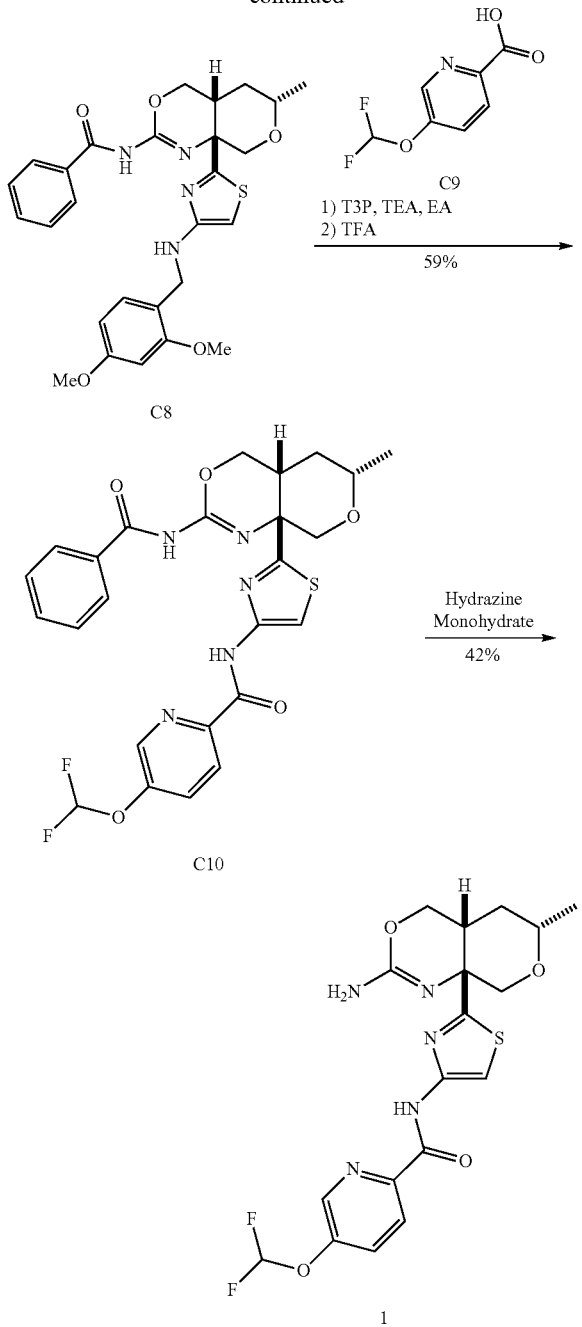

Step 1: Synthesis of N-((6S,8aR)-8a-(4-bromothiazol-2-yl)-6-methyl-4,4a,5,6,8,8a-hexahydropyrano[3,4-d][1,3]oxazin-2-yl)benzamide (C7)

A solution of N-(((3R,4R,6S)-3-(4-bromothiazol-2-yl)-4-(hydroxymethyl)-6-methyltetrahydro-2H-pyran-3-yl)carbamothioyl)benzamide (C6) (1.0 g, 2.1 mmol), potassium carbonate (734 mg, 5.31 mmol), and methyl iodide (754 mg, 5.31 mmol, 0.331 mL) in acetonitrile (28 mL) was stirred at room temperature for 16 hours, and then diluted with saturated aqueous ammonium chloride and extracted with ethyl acetate (three times). The combined ethyl acetate extracts were dried over sodium sulfate, filtered and concentrated in vacuo. Silica gel chromatography (gradient: 0-80% ethyl acetate in heptane) provided the product as a white solid. Yield: 533 mg, 1.22 mmol, 57%. LCMS m/z 438.3 [M+H]$^+$, Br isotope pattern observed. $^1$H NMR (400 MHz, CDCl$_3$) δ ppm 8.25 (d, J=7.4 Hz, 2H), 7.49-7.55 (m, 1H), 7.40-7.47 (m, 2H), 7.28 (s, 1H), 4.13-4.27 (m, 2H), 3.95-4.06 (m, 2H), 3.75 (m, J=11.3, 6.1, 2.3 Hz, 1H), 2.94-3.01 (m, 1H), 1.75-1.81 (m, 1H), 1.59-1.70 (m, 1H), 1.28 (d, J=6.3 Hz, 3H).

Step 2 Synthesis of N-((4aR,6S,8aR)-8a-(4-((2,4-dimethoxybenzyl)amino)thiazol-2-yl)-6-methyl-4,4a,5,6,8,8a-hexahydropyrano[3,4-d][1,3]oxazin-2-yl)benzamide (C8)

A flask charged with tris(dibenzylideneacetone)dipalladium(0) (58.3 mg, 61.1 μmol), tert-butyl xphos (77.8 mg, 0.183 mmol), and sodium tert-butoxide (293 mg, 3.05 mmol) in dioxane (3.55 mL) was purged three times with nitrogen subsequently evacuating with vacuum after each purge. The resulting solution was heated to 85° C.-90° C. (internal reaction temperature) for 5 min. A dioxane (2 mL) solution of N-((6S,8aR)-8a-(4-bromothiazol-2-yl)-6-methyl-4,4a,5,6,8,8a-hexahydropyrano[3,4-d][1,3]oxazin-2-yl)benzamide (C7) (533.0 mg, 1.22 mmol) and 2,4-dimethoxybenzylamine (347 mg, 2.08 mmol, 0.312 mL) was added and the resulting solution was heated 90° C. (internal reaction temperature) for 10 min. The reaction mixture was partitioned between saturated aqueous sodium bicarbonate solution and dichloromethane, separated. The aqueous layer was back-extracted with dichloromethane (twice). The combined dichloromethane extracts were washed with saturated aqueous sodium chloride solution, dried over sodium sulfate, filtered, and concentrated in vacuo. Silica gel chromatography (isocratic eluent: 50% ethyl acetate in heptane) provided the product as an amber solid. Yield: 544 mg, 1.04 mmol, 85%. LCMS m/z 523.5 [M+H]$^+$. $^1$H NMR (400 MHz, CDCl$_3$) δ ppm 8.22-8.32 (m, 2H), 7.49-7.56 (m, 1H), 7.40-7.49 (m, 2H), 7.18 (d, J=8.2 Hz, 1H), 6.41-6.48 (m, 2H), 5.76 (s, 1H), 4.35-4.43 (m, 1H), 4.20 (s, 2H), 4.00 (s, 2H), 3.84 (s, 3H), 3.80 (s, 3H), 3.67-3.76 (m, 1H), 2.86 (br. s., 1H), 1.76 (m, J=13.8, 2.8 Hz, 1H), 1.58-1.66 (m, 1H), 1.26-1.29 (m, 3H).

Step 3: Synthesis of N-(2-((4aR,6S,8aR)-2-benzamido-6-methyl-4,4a,5,6-tetrahydropyrano[3,4-d][1,3]oxazin-8a(8H)-yl)thiazol-4-yl)-5-(difluoromethoxy) picolinamide (C10)

2,4,6-Tripropyl-1,3,5,2,4,6-trioxatriphosphorinane-2,4,6-trioxide (50% solution by weight in ethyl acetate, 0.731 g, 1.15 mmol, 683 μL) was added to a mixture of C9 (86.8 mg, 0.459 mmol) and triethylamine (0.116 g, 1.15 mmol, 160 μL) in ethyl acetate (1.4 mL) and the reaction mixture was heated 65° C. for 20 minutes. N-((4aR,6S,8aR)-8a-(4-((2,4-dimethoxybenzyl)amino)thiazol-2-yl)-6-methyl-4,4a,5,6,8,8a-hexahydropyrano[3,4-d][1,3]oxazin-2-yl)benzamide C8 (150.0 mg, 0.287 mmol) was introduced, and stirring was continued at 65° C. for 1 hour. The reaction mixture was then cooled to room temperature and diluted with ethyl acetate; the resulting solution was washed sequentially with water (twice), saturated aqueous sodium bicarbonate solution, saturated aqueous sodium chloride solution, dried over sodium sulfate, filtered, and concentrated in vacuo. The resulting solid was dissolved in dichloromethane (15 mL) and treated with trifluoroacetic acid (1640 mg, 14.4 mmol, 1.11 mL); the reaction mixture was allowed to stir at room temperature for 6 hours, whereupon it was basified to pH 8 with a mixture of saturated aqueous sodium bicarbonate solution, separated. The aqueous layer was back-extracted with dichloromethane (twice), and the combined organic layers were washed with saturated aqueous sodium chloride solution, dried over sodium sulfate, filtered, and concentrated in vacuo. The residue was purified by silica gel chromatography (gradient: 0-100% ethyl acetate in heptane) to afford a solid. Yield: 92 mg, 0.169 mmol, 59%. LCMS m/z 544.4 [M+H]+. 1H NMR (400 MHz, CDCl3) δ ppm 12.02 (br. s, 1H), 10.43 (s, 1H), 8.48 (d, J=2.5 Hz, 1H), 8.29 (m, J=17.5, 7.9 Hz, 3H), 7.81 (s, 1H), 7.68 (dd, J=8.5, 2.2 Hz, 1H), 7.48-7.54 (m, 1H), 7.41-7.47 (m, 2H), 6.46-6.84 (m, 1H), 4.31 (d, J=9.8 Hz, 1H), 4.17 (d, J=11.5 Hz, 1H), 4.03 (s, 2H), 3.75 (m, J=11.1, 6.1, 2.2 Hz, 1H), 2.89 (m, J=8.0 Hz, 1H), 1.76-1.83 (m, 1H), 1.63-1.74 (m, 1H), 1.30 (d, J=6.1 Hz, 3H).

Step 4: Synthesis of N-(2-((4aR,6S,8aR)-2-amino-6-methyl-4,4a,5,6-tetrahydropyrano[3,4-d][1,3]oxazin-8a(8H)-yl)thiazol-4-yl)-5-(difluoromethoxy) picolinamide (1)

Hydrazine monohydrate (92.8 mg, 1.19 mmol, 89.9 μL) was added to N-(2-((4aR,6S,8aR)-2-benzamido-6-methyl-4,4a,5,6-tetrahydropyrano[3,4-d][1,3]oxazin-8a(8H)-yl)thiazol-4-yl)-5-(difluoromethoxy)picolinamide (C10) (92.1 mg, 0.169 mmol) in dichloromethane (1.7 mL) and the reaction stirred at room temperature for 16 hours. The reaction mixture was partitioned between 1N hydrochloric acid and dichloromethane, separated. The aqueous layer was back-extracted with dichloromethane (twice). The combined dichloromethane extracts were washed with 1N sodium hydroxide, saturated aqueous sodium chloride solution, dried over sodium sulfate, filtered, and concentrated in vacuo. Silica gel chromatography (gradient: 0-10% methanol in dichloromethane) provided the product as a white solid. Yield: 31 mg, 72 μmol, 42%. LCMS m/z 440.2 [M+H]+. 1H NMR (400 MHz, CD3OD) δ ppm 8.55 (d, J=2.7 Hz, 1H), 8.26 (d, J=8.6 Hz, 1H), 7.79-7.83 (m, 1H), 7.71 (s, 1H), 6.89-7.27 (m, 1H), 3.87-4.00 (m, 3H), 3.76-3.80 (m, 1H), 3.66-3.74 (m, 1H), 2.67-2.73 (m, 1H), 1.69-1.75 (m, 1H), 1.43-1.54 (m, 1H), 1.24 (d, J=6.3 Hz, 3H).

Example 2

N-(2-((4aR,6S,8aR)-2-amino-6-methyl-4,4a,5,6-tetrahydropyrano[3,4-d][1,3]oxazin-8a(8H)-yl)thiazol-4-yl)-3-chloro-5-(difluoromethoxy)picolinamide (2)

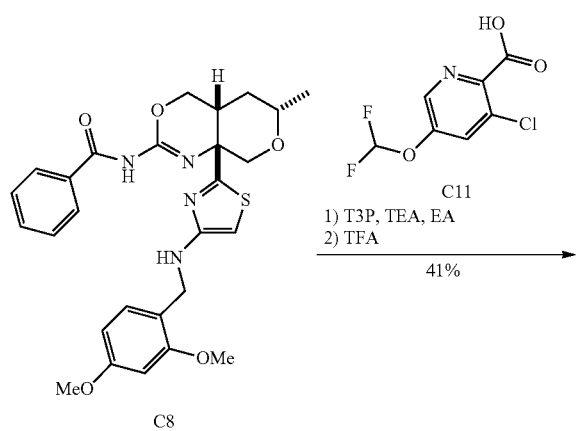

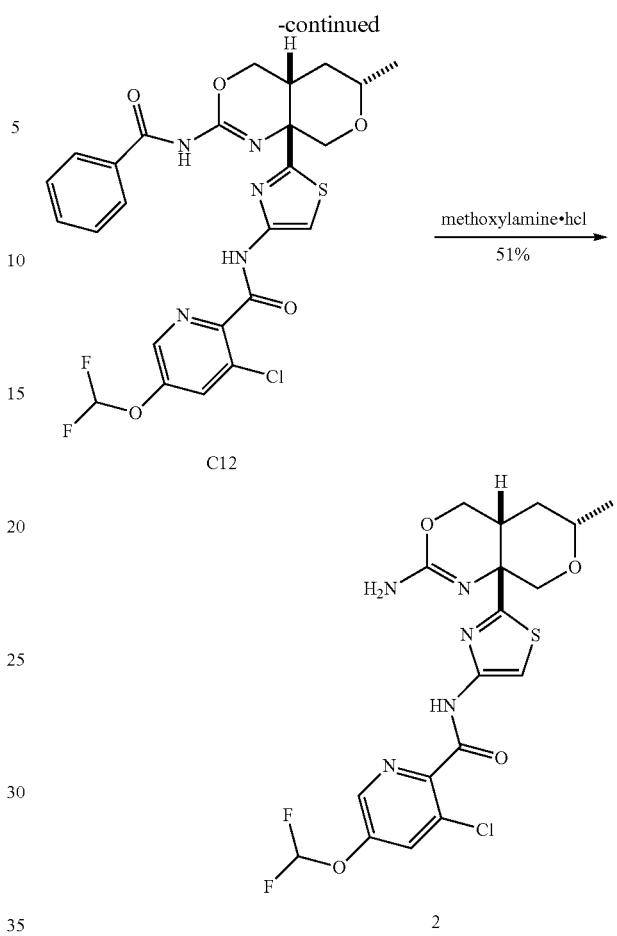

Step 1: Synthesis of N-(2-((4aR,6S,8aR)-2-benzamido-6-methyl-4,4a,5,6-tetrahydro pyrano[3,4-d][1,3]oxazin-8a(8H)-yl)thiazol-4-yl)-3-chloro-5-(difluoromethoxy) picolinamide (C12)

2,4,6-Tripropyl-1,3,5,2,4,6-trioxatriphosphorinane-2,4,6-trioxide (50% solution by weight in ethyl acetate, (0.719 g, 1.13 mmol, 672 μL) was added to a mixture of 3-chloro-5-(difluoromethoxy)picolinic acid C11 (101.1 mg, 0.452 mmol) and triethylamine (0.114 g, 1.13 mmol, 157 μL) in ethyl acetate (1.4 mL) and the reaction mixture was heated 65° C. for 20 minutes. N-((4aR,6S,8aR)-8a-(4-((2,4-Dimethoxybenzyl)amino)thiazol-2-yl)-6-methyl-4,4a,5,6,8,8a-hexahydropyrano[3,4-d][1,3]oxazin-2-yl)benzamide C8 (150 mg, 0.287 mmol) was introduced, and stirring was continued at 65° C. for 1 hour. The reaction mixture was then cooled to room temperature and diluted with ethyl acetate; the resulting solution was washed sequentially with water (twice), saturated aqueous sodium bicarbonate solution, saturated aqueous sodium chloride solution, dried over sodium sulfate, filtered, and concentrated in vacuo. The resulting solid was dissolved in dichloromethane (15 mL) and treated with trifluoroacetic acid (1.61 g, 14.1 mmol, 1.09 mL); the reaction mixture was allowed to stir at room temperature for 16 hours, whereupon it was basified to pH 8 with a mixture of saturated aqueous sodium bicarbonate solution, separated. The aqueous layer was back-extracted with dichloromethane (twice), and the combined organic layers were washed with saturated aqueous sodium chloride solution, dried over sodium sulfate, filtered, and concentrated in vacuo. The residue was purified by silica gel chromatography (gradient: 0-100% ethyl acetate in heptane) to afford a solid. Yield: 69 mg, 0.119 mmol, 41%. LCMS m/z 478.3 [M+H]⁺. ¹H NMR (400 MHz, CDCl₃) δ ppm 10.40 (s, 1H), 8.42 (d, J=2.4 Hz, 1H), 8.26 (m, J=7.0 Hz, 2H), 7.84 (s, 1H), 7.70 (d, J=2.4 Hz, 1H), 7.50 (m, J=7.2 Hz, 1H), 7.41-7.46 (m, 2H), 6.48-6.85 (m, 1H), 4.28-4.34 (m, 1H), 4.13-4.19 (m, 1H), 4.02 (s, 2H), 3.69-3.78 (m, 1H), 2.83-2.89 (m, 1H), 1.77 (m, J=2.3 Hz, 1H), 1.63-1.74 (m, 1H), 1.29 (d, J=6.1 Hz, 3H).

Step 2: Synthesis of N-(2-((4aR,6S,8aR)-2-amino-6-methyl-4,4a,5,6-tetrahydropyrano[3,4-d][1,3]oxazin-8a(8H)-yl)thiazol-4-yl)-3-chloro-5-(difluoromethoxy) picolinamide (2)

A solution of N-(2-((4aR,6S,8aR)-2-benzamido-6-methyl-4,4a,5,6-tetrahydro pyrano[3,4-d][1,3]oxazin-8a (8H)-yl)thiazol-4-yl)-3-chloro-5-(difluoromethoxy) picolinamide (C12) (68.7 mg, 0.119 mmol), methoxylamine hydrochloride (101 mg, 1.19 mmol), and pyridine (0.95 g, 11.8 mmol, 0.98 mL) in ethanol (2 mL) was heated to 50° C. for 3 hours. The solution was concentrated to half the volume in vacuo, then partitioned between dichloromethane and 1N sodium hydroxide and the layers were separated. The aqueous layer was back-extracted with dichloromethane (twice). The combined dichloromethane extracts were washed with water, saturated aqueous sodium chloride solution, dried over sodium sulfate, filtered, and concentrated in vacuo. Silica gel chromatography (gradient: 0-10% methanol in dichloromethane) provided a solid. Yield: 29 mg, 0.06 mmol, 51%. LCMS m/z 474.4 [M+H]⁺. ¹H NMR (400 MHz, CD₃OD) δ ppm 8.48-8.49 (m, 1H), 7.88-7.89 (m, 1H), 7.70 (s, 1H), 6.92-7.29 (m, 1H), 3.86-4.01 (m, 3H), 3.76-3.80 (m, 1H), 3.63-3.72 (m, 1H), 2.66-2.72 (m, 1H), 1.68-1.74 (m, 1H), 1.42-1.52 (m, 1H), 1.23 (d, J=6.3 Hz, 3H).

Example 3

N-(2-((4aR,6S,8aR)-2-amino-6-methyl-4,4a,5,6-tetrahydropyrano[3,4-d][1,3]oxazin-8a(8H)-yl)thiazol-4-yl)-5-(difluoromethoxy)-3-methylpicolinamide (3)

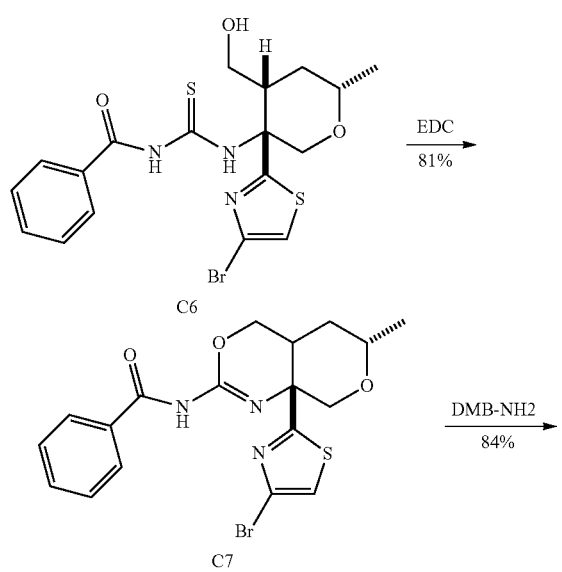

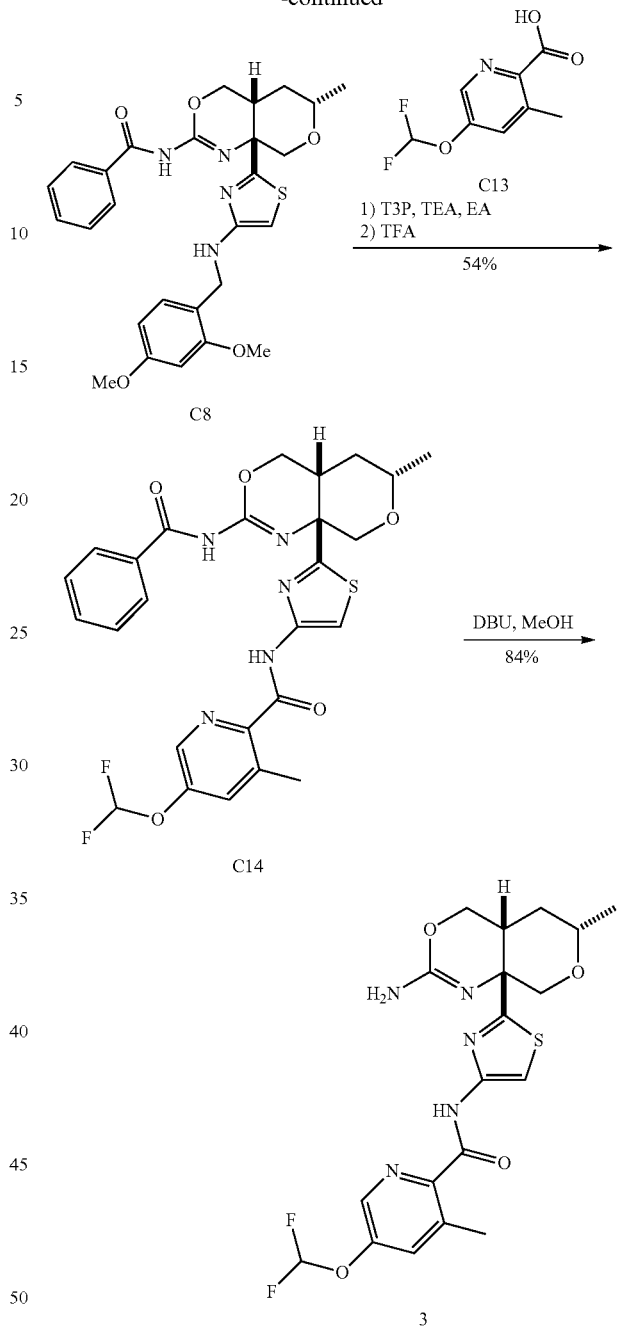

Step 1: Synthesis of N-((6S,8aR)-8a-(4-bromothiazol-2-yl)-6-methyl-4,4a,5,6,8,8a-hexahydropyrano[3,4-d][1,3]oxazin-2-yl)benzamide (C7)

To a solution of N-(((3R,4R,6S)-3-(4-bromothiazol-2-yl)-4-(hydroxymethyl)-6-methyltetrahydro-2H-pyran-3-yl)carbamothioyl)benzamide C6 (36.62 g, 77.85 mmol) in acetonitrile (311 mL) was added N-(3-dimethylaminopropyl)-N'-ethylcarbodiimide hydrochloride (18.1 g, 94.2 mmol), and the reaction mixture was stirred at 25° C. for 16 hours. After removal of half the solvent in vacuo, this was combined with a previous reaction done on 10.0 g, 21.3 mmol scale. The combined mixture was diluted with ethyl acetate, washed sequentially with water (two times), 0.1N aqueous hydrochloric acid, saturated aqueous sodium bicarbonate solution, dried over sodium sulfate, filtered, and concentrated in vacuo. Trituration in ethyl acetate and heptane provided the product as a white solid. Yield: 34.99 g, 80.2 mmol, 81%. LCMS m/z 438.3 [M+H]$^+$, Br isotope pattern observed. $^1$H NMR (400 MHz, CDCl$_3$) δ ppm 12.04 (br. s, 1H), 8.24 (d, J=7.2 Hz, 2H), 7.48-7.54 (m, 1H), 7.40-7.46 (m, 2H), 7.27 (s, 1H), 4.11-4.26 (m, 2H), 3.93-4.07 (m, 2H), 3.75 (m, J=11.2, 6.1, 2.4 Hz, 1H), 2.92-3.01 (m, 1H), 1.78 (m, J=13.9, 5.2, 2.3 Hz, 1H), 1.65 (m, J=13.3, 13.3, 11.3 Hz, 1H), 1.28 (d, J=6.1 Hz, 3H).

Step 2: Synthesis of N-((4aR,6S,8aR)-8a-(4-((2,4-dimethoxybenzyl)amino) thiazol-2-yl)-6-methyl-4,4a,5,6,8,8a-hexahydropyrano[3,4-d][1,3]oxazin-2-yl) benzamide (C8)

A flask charged with tris(dibenzylideneacetone)dipalladium(0) (1.09 g, 1.15 mmol), tert-butyl xphos (1.46 g, 3.44 mmol), and sodium tert-butoxide (5.51 g, 57.3 mmol) in dioxane (54 mL) was purged three times with nitrogen subsequently evacuating with vacuum after each purge. The resulting solution was heated to 85° C.-90° C. (internal reaction temperature) for 5 min. A dioxane (50 mL) solution of N-((6S,8aR)-8a-(4-bromothiazol-2-yl)-6-methyl-4,4a,5,6,8,8a-hexahydropyrano[3,4-d][1,3]oxazin-2-yl)benzamide C7 (10.0 g, 22.9 mmol) and 2,4-dimethoxybenzylamine (6.51 g, 39.0 mmol, 5.85 mL) was added and the resulting solution was heated at 90° C. (internal reaction temperature) for 10 min. The reaction mixture was partitioned between saturated aqueous sodium bicarbonate solution and dichloromethane, separated. The aqueous layer was back-extracted with dichloromethane (twice). The combined dichloromethane extracts were washed with saturated aqueous sodium chloride solution, dried over sodium sulfate, filtered, and concentrated in vacuo. Silica gel chromatography (isocratic eluent: 50% ethyl acetate in heptane) provided the product as an amber solid. Yield: 10.0 g, 19.2 mmol, 84%. LCMS m/z 523.5 [M+H]$^+$. $^1$H NMR (400 MHz, CDCl$_3$) δ ppm 8.24-8.29 (m, 2H), 7.50 (d, J=7.2 Hz, 1H), 7.40-7.47 (m, 2H), 7.18 (d, J=8.2 Hz, 1H), 6.47 (d, J=2.4 Hz, 1H), 6.44 (dd, J=8.2, 2.4 Hz, 1H), 5.75 (s, 1H), 4.31-4.38 (m, 1H), 4.20 (s, 2H), 4.12 (d, J=7.2 Hz, 1H), 3.99 (s, 2H), 3.84 (s, 3H), 3.80 (s, 3H), 3.64-3.77 (m, 1H), 2.82-2.89 (m, 1H), 1.73 (m, J=5.3, 2.2 Hz, 1H), 1.57-1.68 (m, 1H), 1.25-1.28 (m, 3H).

Step 3: Synthesis of N-(2-((4aR,6S,8aR)-2-benzamido-6-methyl-4,4a,5,6-tetrahydropyrano[3,4-d][1,3]oxazin-8a(8H)-yl)thiazol-4-yl)-5-(difluoromethoxy)-3-methylpicolinamide (C14)

2,4,6-Tripropyl-1,3,5,2,4,6-trioxatriphosphorinane-2,4,6-trioxide (50% solution by weight in ethyl acetate, 92.0 g, 145 mmol, 86.1 mL) was added to a mixture of 5-(difluoromethoxy)-3-methylpicolinic acid (C13) (11.7 g, 57.8 mmol) and triethylamine (14.6 g, 145 mmol, 20.1 mL) in ethyl acetate (180 mL), and the reaction mixture was heated 65° C. for 20 minutes. N-((4aR,6S,8aR)-8a-(4-((2,4-dimethoxybenzyl)amino)thiazol-2-yl)-6-methyl-4,4a,5,6,8,8a-hexahydropyrano[3,4-d][1,3]oxazin-2-yl)benzamide C8 (18.89 g, 33.88 mmol) dissolved in ethyl acetate (50 mL) was introduced, and stirring was continued at 65° C. for 1 hour. The reaction mixture was then cooled to room temperature and diluted with ethyl acetate; the resulting solution was washed sequentially with water (twice), saturated aqueous sodium bicarbonate solution, saturated aqueous sodium chloride solution, dried over sodium sulfate, filtered, and concentrated in vacuo. The resulting solid was dissolved in dichloromethane (1.89 L) and treated with trifluoroacetic acid (139 mL); the reaction mixture was allowed to stir at room temperature for 16 hours, whereupon it was basified to pH 8 with a mixture of saturated aqueous sodium bicarbonate solution and 1N sodium hydroxide, separated. The aqueous layer was back-extracted with dichloromethane (twice), and the combined organic layers were washed with saturated aqueous sodium chloride solution, dried over sodium sulfate, filtered, and concentrated in vacuo. The residue was purified by silica gel chromatography (gradient: 0-100% ethyl acetate in heptane) to afford a solid, which was triturated with heptane and ethyl acetate to provide the product as a yellow solid. Yield: 10.9 g, 19.5 mmol, 54%. LCMS m/z 558.4 [M+H]$^+$. $^1$H NMR (400 MHz, CDCl$_3$) δ ppm 10.62 (s, 1H), 8.33 (d, J=2.5 Hz, 1H), 8.27 (d, J=7.2 Hz, 2H), 7.78 (s, 1H), 7.48-7.55 (m, 1H), 7.40-7.47 (m, 3H), 6.44-6.82 (m, 1H), 4.28-4.36 (m, 1H), 4.13-4.21 (m, 1H), 4.03 (s, 2H), 3.70-3.79 (m, 1H), 2.86-2.93 (m, 1H), 2.83 (s, 3H), 1.75-1.82 (m, 1H), 1.62-1.73 (m, 1H), 1.30 (d, J=6.3 Hz, 3H).

Step 4: Synthesis of N-(2-((4aR,6S,8aR)-2-amino-6-methyl-4,4a,5,6-tetrahydropyrano [3,4-d][1,3]oxazin-8a(8H)-yl)thiazol-4-yl)-5-(difluoromethoxy)-3-methylpicolinamide (3)

A solution of N-(2-((4aR,6S,8aR)-2-benzamido-6-methyl-4,4a,5,6-tetrahydro pyrano[3,4-d][1,3]oxazin-8a(8H)-yl)thiazol-4-yl)-5-(difluoromethoxy)-3-methyl picolinamide (C14) (22.84 g, 40.96 mmol) and 1,8-diazabicyclo (5.4.0)undec-7-ene (95%, 6.56 g, 41.0 mmol, 6.45 mL) in methyl alcohol (660 mL) was heated at 70° C. for 16 hours. After removal of solvent in vacuo, the residue was triturated in diethyl ether to provide the product as a white solid. Yield: 15.6 g, 34.4 mmol, 84%. LCMS m/z 454.4 [M+H]$^+$. $^1$H NMR (400 MHz, CD$_3$OD) δ ppm 8.37 (d, J=2.5 Hz, 1H), 7.67 (s, 1H), 7.58 (d, J=2.5 Hz, 1H), 6.86-7.25 (m, 1H), 3.85-4.00 (m, 4H), 3.74-3.80 (m, 1H), 3.64-3.74 (m, 1H), 2.75 (s, 3H), 2.65-2.72 (m, 1H), 1.68-1.75 (m, 1H), 1.42-1.54 (m, 1H), 1.23 (d, J=6.1 Hz, 3H).

Examples 4 and 5

N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy)-3-methylpicolinamide (5) and N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy)picolinamide (4)

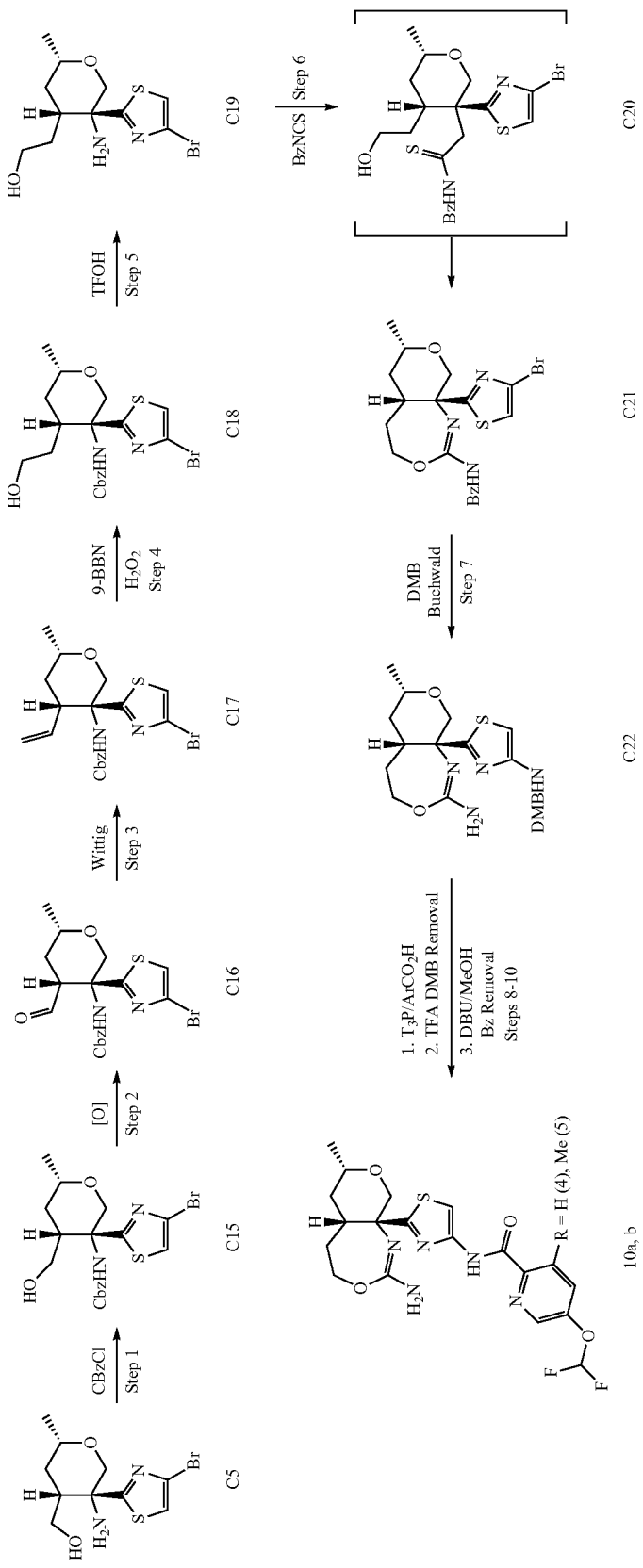

Step 1: Synthesis of benzyl ((3R,4R,6S)-3-(4-bromothiazol-2-yl)-4-(hydroxymethyl)-6-methyltetrahydro-2H-pyran-3-yl)carbamate: (C15)

To a solution of ((2S,4R,5R)-5-amino-5-(4-bromothiazol-2-yl)-2-methyltetrahydro-2H-pyran-4-yl)methanol (C5) (2.7 g, 8.8 mmol) in DCM (48.8 mL) and saturated NaHCO$_3$ (48.8 mL) at 0° C. was added benzyl chloroformate (1.95 mL, 13.2 mmol). The tightly stoppered reaction mixture was slowly warmed to room temp as the ice bath expired and was stirred for 18 h. The reaction was poured into a separatory funnel and the phases were separated. The aqueous layer was extracted with DCM (1×). The combined DCM extracts were washed with brine (1×), dried over Na$_2$SO$_4$, filtered and then concentrated in vacuo to give the crude product which was purified on silica gel (gradient: 0-100% ethyl acetate in heptane) to yield 2.17 g (56%). LCMS m/z 443.3 [M−H]$^+$. $^1$H NMR (400 MHz, CDCl$_3$) δ 7.31-7.46 (m, 5H), 7.18 (s, 1H), 6.82 (s, 1H), 5.15-5.24 (m, 1H), 5.05-5.13 (m, 1H), 4.82 (d, J=11.7 Hz, 1H), 3.56-3.82 (m, 4H), 2.52 (dd, J=2.5, 12.7 Hz, 1H), 2.07-2.18 (m, 1H), 1.76-1.90 (m, 1H), 1.61 (td, J=3.2, 13.6 Hz, 1H), 1.24-1.36 (m, 3H)

Step 2: Synthesis of benzyl ((3R,4R,6S)-3-(4-bromothiazol-2-yl)-4-formyl-6-methyl tetrahydro-2H-pyran-3-yl)carbamate: (C16)

Dess-Martin reagent (950 mg, 2.18 mmol) was added to a solution of benzyl ((3R,4R,6S)-3-(4-bromothiazol-2-yl)-4-(hydroxymethyl)-6-methyltetrahydro-2H-pyran-3-yl)carbamate (C15) (800 mg, 1.81 mmol) in DCM (12.9 mL) cooled to 0° C. under nitrogen. The reaction was stirred at 0° C. for 30 min before being warmed to rt. After 2 h the reaction was quenched with saturated aqueous sodium bicarbonate (20 mL) and saturated aqueous sodium thiosulfate (10 mL). The mixture was stirred for 20 min, then poured into a separatory funnel. The layers were separated and the aqueous layer extracted with DCM (2×). The combined organic layers were washed with saturated aqueous sodium bicarbonate, brine, dried over sodium sulfate, and concentrated to give crude product. The crude was subjected to silica gel column chromatography using a 0-100% EtOAc/heptane gradient to give 720 mg of desired product (90%). LCMS m/z 440.5 [M−H]$^+$. $^1$H NMR (400 MHz, CDCl$_3$) δ 9.84 (br. s., 1H), 7.28-7.43 (m, 5H), 5.79 (br. s., 1H), 4.97-5.15 (m, 2H), 3.89-3.98 (m, 1H), 3.68-3.80 (m, 1H), 3.56-3.68 (m, 2H), 1.90-2.03 (m, 1H), 1.57-1.67 (m, 1H), 1.20-1.35 (m, 4H).

Step 3: Synthesis of benzyl ((3R,4S,6S)-3-(4-bromothiazol-2-yl)-6-methyl-4-vinyltetrahydro-2H-pyran-3-yl)carbamate: (C17)

1M Potassium tert-butoxide in THF (4.72 mL, 4.72 mmol) was added to a suspension of methyltriphenylphosphonium iodide (2.07 g, 5.67 mmol) in THF (38 mL) under nitrogen. The mixture was stirred for 15 min before being cooled to 0° C. Benzyl ((3R,4R,6S)-3-(4-bromothiazol-2-yl)-4-formyl-6-methyltetrahydro-2H-pyran-3-yl) carbamate (C16) (830 mg, 1.89 mmol) in a minimum amount of THF was then added dropwise. The reaction was allowed to warm to rt and stirred for 1 h. The reaction was cooled back down to 0° C. and quenched with saturated aqueous NH$_4$Cl. The mixture was poured into a separatory funnel and the phases separated. The aqueous phase was extracted with EtOAc (2×) and the combined organics were dried over sodium sulfate. The solution was concentrated and the residue was subjected to silica chromatography using a 0-30% EtOAc/heptane gradient to give 530 mg of desired product (64%). LCMS m/z 439.2 [M−H]$^+$. $^1$H NMR (400 MHz, CDCl$_3$) δ 7.31-7.51 (m, 5H), 7.19 (s, 1H), 5.55-5.73 (m, 1H), 5.21 (d, J=10.9 Hz, 2H), 4.97-5.16 (m, 4H), 3.98 (d, J=12.1 Hz, 1H), 3.68-3.83 (m, 1H), 3.11-3.26 (m, 1H), 1.68-1.80 (m, 1H), 1.47-1.63 (m, 1H), 0.91 (t, J=6.8 Hz, 3H).

Step 4: Synthesis of benzyl ((3R,4R,6S)-3-(4-bromothiazol-2-yl)-4-(2-hydroxyethyl)-6-methyltetrahydro-2H-pyran-3-yl)carbamate: (C18)

Benzyl ((3R,4S,6S)-3-(4-bromothiazol-2-yl)-6-methyl-4-vinyltetrahydro-2H-pyran-3-yl)carbamate (C17) (530 mg, 1.21 mmol) was dissolved in THF (24.2 mL) and then 9-BBN (4.85 mL, 2.42 mmol) was added dropwise. The reaction was stirred at rt for 18 h then quenched with water (6 mL) and 1N NaOH (3 mL). The solution was then cooled to 0° C. and H$_2$O$_2$ (4 mL) was added slowly. The reaction was partitioned between diethyl ether and water, the layers separated and then the aqueous layer was extracted with diethyl ether (2×). The combined organic layers were dried over sodium sulfate, filtered, and concentrated to yield 410 mg of crude product (74%). LCMS m/z 455.3 [M−H]$^+$. $^1$H NMR (400 MHz, CDCl$_3$) δ 7.84 (s, 1H), 7.31-7.46 (m, 5H), 7.21 (s, 1H), 5.74 (br. s., 1H), 5.18 (s, 1H), 5.03-5.12 (m, 1H), 4.46-4.64 (m, 1H), 3.71 (d, J=11.7 Hz, 3H), 2.68-2.83 (m, 1H), 2.09-2.23 (m, 1H), 1.74-1.91 (m, 2H), 1.59-1.69 (m, 1H), 1.31-1.47 (m, 1H), 1.22-1.31 (m, 3H).

Step 5: Synthesis of 2-((2S,4R,5R)-5-amino-5-(4-bromothiazol-2-yl)-2-methyltetrahydro-2H-pyran-4-yl)ethan-1-ol (C19)

Benzyl ((3R,4R,6S)-3-(4-bromothiazol-2-yl)-4-(2-hydroxyethyl)-6-methyl tetrahydro-2H-pyran-3-yl)carbamate (C18) (410 mg, 0.9 mmol) was treated with triflic acid (4.3 mL, 22.5 mmol) and stirred at rt for 30 min. The reaction was concentrated and the residue was taken up in DCM and saturated aqueous sodium bicarbonate. The aqueous layer was extracted with DCM (3×). The combined organic layers were dried over sodium sulfate, filtered, and concentrated to yield 285 mg of crude product (98%). LCMS m/z 323.2 [M−H]$^+$. $^1$H NMR (400 MHz, CDCl$_3$) δ 7.03-7.22 (m, 1H), 5.28 (s, 1H), 3.68 (s, 1H), 3.56-3.64 (m, 2H), 3.40-3.54 (m, 2H), 2.67 (tdd, J=4.3, 8.3, 12.5 Hz, 1H), 1.69-1.80 (m, 1H), 1.33 (s, 3H), 1.23 (d, J=6.3 Hz, 3H).

Step 6: Synthesis of N-((5aR,7S,9aR)-9a-(4-bromothiazol-2-yl)-7-methyl-5,5a,6,7,9,9a-hexahydro-4H-pyrano[3,4-d][1,3]oxazepin-2-yl)benzamide (C21)

2-((2S,4R,5R)-5-Amino-5-(4-bromothiazol-2-yl)-2-methyltetrahydro-2H-pyran-4-yl)ethan-1-ol (C19) (280 mg, 0.87 mmol) was dissolved in DCM (8.72 mL) and benzoyl isothicyanate (0.11 mL, 0.86 mmol) were added. The reaction was stirred for 3 hours and then concentrated. The residue was taken up in acetonitrile (5.1 mL) and EDC (109 mg, 0.57 mmol). The reaction was stirred at rt for 18 h, then concentrated. The residue was dissolved in EtOAc and washed with water. The organic phase was washed with brine, dried over sodium sulfate, filtered, and concentrated. LCMS m/z 452.2 [M−H]$^+$.

Step 7: Synthesis of N-((5aR,7S,9aR)-9a-(4-((2,4-dimethoxybenzyl)amino) thiazol-2-yl)-7-methyl-5,5a,6,7,9,9a-hexahydro-4H-pyrano[3,4-d][1,3]oxazepin-2-yl)benzamide (C22)

Pd$_2$(dba)$_3$ (19 mg, 0.02 mmol), tert-butyl X-Phos (27 mg, 64 μmol), and sodium tert-butoxide (99 mg, 1.03 mmol)

were dissolved in anhydrous dioxane (2.3 mL) in an oven dried flask under N$_2$. The flask was purged with N$_2$ (3×) and heated to 95° C. In a separate flask N-((5aR,7S,9aR)-9a-(4-bromothiazol-2-yl)-7-methyl-5,5a,6,7,9,9a-hexahydro-4H-pyrano[3,4-d][1,3]oxazepin-2-yl)benzamide (C21) (185 mg, 0.41 mmol) and 2,4-dimethoxybenzylamine (0.1 mL, 0.69 mmol) were dissolved in a minimum amount of anhydrous dioxane. This solution was added to the flask at 95° C. and stirred for 15 min. The reaction was cooled to rt, then Celite and water were added. The mixture was stirred for 1 min, then filtered through a Celite pad, using DCM as an eluent. The pad was washed with DCM (3×). The combined organic layers were washed with water (3×), 5% aqueous citric acid (2×), aqueous sodium bicarbonate (1×), brine (1×), dried over sodium sulfate, filtered and concentrated. The residue was subjected to silica gel chromatography using a 0-100% EtOAc/heptane gradient to yield 90 mg of white solid (41%). LCMS m/z 537.3 [M−H$^+$].

Step 8a: Synthesis of N-(2-((5aR,7S,9aR)-2-benzamido-7-methyl-5,5a,6,7-tetrahydro-4H-pyrano[3,4-d][1,3]oxazepin-9a(9H)-yl)thiazol-4-yl)-5-(difluoromethoxy)-N-(2,4-dimethoxybenzyl)-3-methylpicolinamide A solution of 5-(difluoromethoxy)-3-methylpicolinic acid (21 mg, 0.1 mmol) in EtOAc (0.13 mL) was treated with TEA (0.035 mL) and T3P (50% wt in EtOAc, 0.15 mL, 0.25 mmol). The reaction was heated to 60° C. for 20 min then N-((5aR,7S,9aR)-9a-(4-((2,4-dimethoxybenzyl)amino)thiazol-2-yl)-7-methyl-5,5a,6,7,9,9a-hexahydro-4H-pyrano[3,4-d][1,3]oxazepin-2-yl)benzamide (C22) (34 mg, 0.06 mmol) was added and the reaction stirred for 1 h. The reaction was then diluted with water and EtOAc. The phases were separated and the aqueous phase extracted with EtOAc (2×). The combined organics were washed with saturated aqueous sodium bicarbonate, brine, dried over sodium sulfate, filtered and concentrated to yield 45 mg of crude product (98%). LCMS m/z 722.4 [M−H$^+$].

Step 9a: Synthesis of N-(2-((5aR,7S,9aR)-2-benzamido-7-methyl-5,5a,6,7-tetrahydro-4H-pyrano[3,4-d][1,3]oxazepin-9a(9H)-yl)thiazol-4-yl)-5-(difluoromethoxy)-3-methylpicolinamide N-(2-((5aR,7S,9aR)-2-Benzamido-7-methyl-5,5a,6,7-tetrahydro-4H-pyrano[3,4-d][1,3]oxazepin-9a(9H)-yl)thiazol-4-yl)-5-(difluoromethoxy)-N-(2,4-dimethoxybenzyl)-3-methylpicolinamide (45 mg, 0.06 mmol) was dissolved in DCM (0.3 mL) and treated with TFA (0.12 mL, 1.56 mmol). The reaction was stirred at rt for 48 h. The reaction was concentrated then taken up in EtOAc and sat. aqueous sodium bicarbonate. The aqueous layer was extracted with EtOAc (2×). The combined organics were washed with brine, dried over sodium sulfate, filtered, and concentrated to yield 35 mg of crude product (98%). LCMS m/z 572.3 [M−H$^+$].

Step 10a: Synthesis of N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy)-3-methylpicolinamide (5)

N-(2-((5aR,7S,9aR)-2-Benzamido-7-methyl-5,5a,6,7-tetrahydro-4H-pyrano[3,4-d][1,3]oxazepin-9a(9H)-yl)thiazol-4-yl)-5-(difluoromethoxy)-3-methylpicolinamide (35 mg, 0.06 mmol) was dissolved in MeOH (1.2 mL) and treated with DBU (11.6 µL, 74 µmol). The reaction was heated to 60° C. for 2 h. The reaction was concentrated and the residue subjected to silica gel chromatography using a 0-10% MeOH/DCM gradient to yield 13.5 mg of product (47%). LCMS m/z 468.3 [M−H$^+$]. $^1$H NMR (400 MHz, CDCl$_3$) δ 10.56 (br. s., 1H), 8.32 (d, J=2.0 Hz, 1H), 7.67 (s, 1H), 7.36-7.44 (m, 1H), 6.38-6.85 (m, 1H), 3.89-4.06 (m, 2H), 3.77 (d, J=10.9 Hz, 1H), 3.66-3.74 (m, 1H), 3.54 (d, J=10.9 Hz, 1H), 2.97-3.08 (m, 1H), 2.83 (s, 3H), 2.19-2.32 (m, 1H), 1.87 (dt, J=11.3, 13.1 Hz, 1H), 1.38-1.52 (m, 2H), 1.29 (d, J=6.2 Hz, 3H).

Step 8b: Synthesis of N-(2-((5aR,7S,9aR)-2-benzamido-7-methyl-5,5a,6,7-tetrahydro-4H-pyrano[3,4-d][1,3]oxazepin-9a(9H)-yl)thiazol-4-yl)-5-(difluoromethoxy)-N-(2,4-dimethoxybenzyl)picolinamide A solution of 5-(difluoromethoxy)picolinic acid (25 mg, 0.13 mmol) in EtOAc (0.16 mL) was treated with TEA (0.046 mL) and T3P (50% wt in EtOAc, 0.195 mL, 0.33 mmol). The reaction was heated to 60° C. for 20 min then N-((5aR,7S,9aR)-9a-(4-((2,4-dimethoxybenzyl)amino)thiazol-2-yl)-7-methyl-5,5a,6,7,9,9a-hexahydro-4H-pyrano[3,4-d][1,3]oxazepin-2-yl)benzamide (C22) (44 mg, 0.08 mmol) was added and the reaction stirred for 1 h. The reaction was then diluted with water and EtOAc. The phases were separated and the aqueous phase extracted with EtOAc (2×). The combined organics were washed with saturated aqueous sodium bicarbonate, brine, dried over sodium sulfate, filtered and concentrated to yield 55 mg of crude product (98%). LCMS m/z 708.3 [M−H$^+$].

Step 9b: Synthesis of N-(2-((5aR,7S,9aR)-2-benzamido-7-methyl-5,5a,6,7-tetrahydro-4H-pyrano[3,4-d][1,3]oxazepin-9a(9H)-yl)thiazol-4-yl)-5-(difluoromethoxy)picolinamide N-(2-((5aR,7S,9aR)-2-Benzamido-7-methyl-5,5a,6,7-tetrahydro-4H-pyrano[3,4-d][1,3]oxazepin-9a(9H)-yl)thiazol-4-yl)-5-(difluoromethoxy)-N-(2,4-dimethoxybenzyl) picolinamide (55 mg, 0.08 mmol) was dissolved in DCM (0.4 mL) and treated with TFA (0.15 mL, 1.94 mmol). The reaction was stirred at rt for 2 h. The reaction was concentrated then taken up in EtOAc and saturated aqueous sodium bicarbonate. The aqueous layer was extracted with EtOAc (2×). The combined organics were washed with brine, dried over sodium sulfate, filtered, and concentrated to yield 42 mg of crude product (97%). LCMS m/z 558.3 [M−H$^+$].

Step 10b: Synthesis of N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy)picolinamide: 4

N-(2-((5aR,7S,9aR)-2-Benzamido-7-methyl-5,5a,6,7-tetrahydro-4H-pyrano[3,4-d][1,3]oxazepin-9a(9H)-yl)thiazol-4-yl)-5-(difluoromethoxy)picolinamide (42 mg, 75 µmol) was dissolved in MeOH (1.5 mL) and treated with DBU (14.2 µL, 0.09 mmol). The reaction was heated to 60° C. for 2 h. The reaction was concentrated and the residue was subjected to silica gel chromatography using a 0-10% MeOH/DCM gradient to yield 12.3 mg of product (36%). LCMS m/z 454.3 [M−H$^+$]. $^1$H NMR (400 MHz, CDCl$_3$) δ 10.39 (br. s., 1H), 8.46 (d, J=2.7 Hz, 1H), 8.31 (d, J=8.6 Hz, 1H), 7.70 (s, 1H), 7.66 (dd, J=2.5, 8.4 Hz, 1H), 6.41-6.88 (m, 1H), 3.87-3.99 (m, 1H), 3.72-3.81 (m, 1H), 3.64-3.72 (m, 1H), 3.53 (d, J=11.0 Hz, 1H), 2.92-3.08 (m, 1H), 2.17-2.34 (m, 1H), 1.79-1.97 (m, 1H), 1.39-1.57 (m, 2H), 1.14-1.33 (m, 4H).

Example 6

N-(2-((4S,4aR,6S,8aR)-2-amino-4-(fluoromethyl)-6-methyl-4,4a,5,6-tetrahydro pyrano[3,4-d][1,3]oxazin-8a(8H)-yl)thiazol-4-yl)-5-(difluoromethoxy)picolinamide (6)

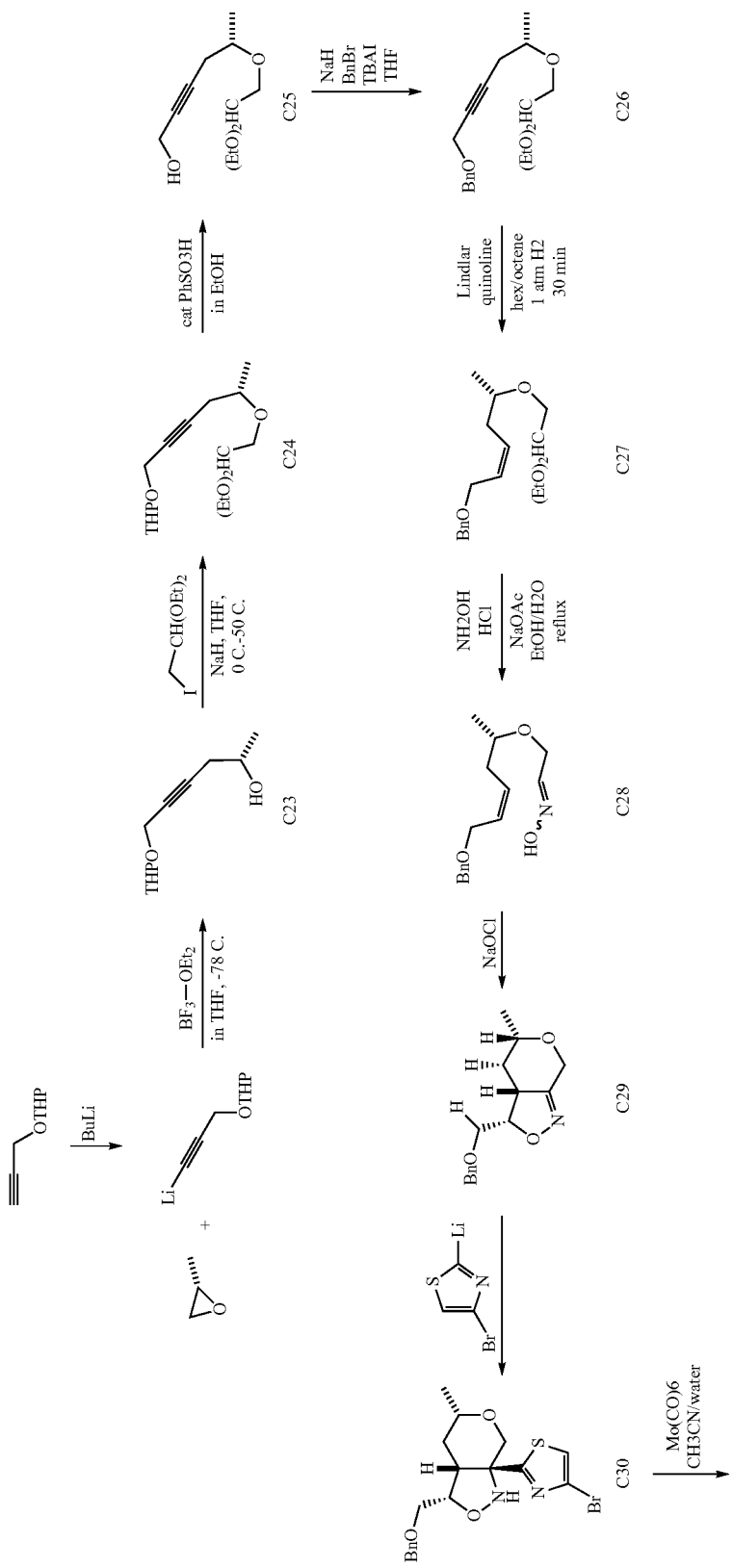

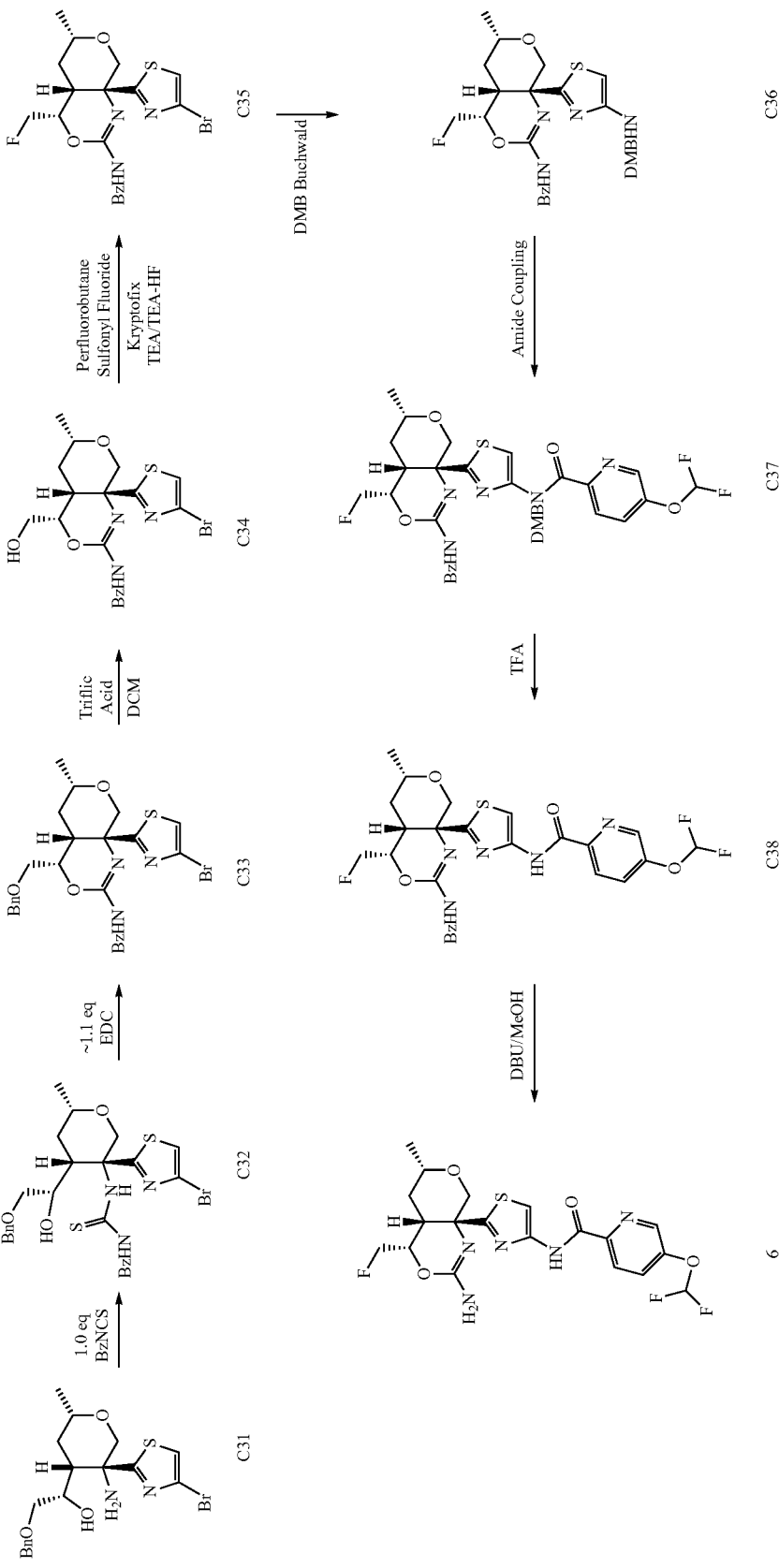

Step 1: Synthesis of (2S)-6-((tetrahydro-2H-pyran-2-yl)oxy)hex-4-yn-2-ol (C23)

To a stirred solution of 2-(2-propynyloxy)tetrahydro-2H-pyran (7.96 g, 56.8 mmol) in THF (60 mL) under nitrogen atmosphere at −70° C. was added n-BuLi (24.8 mL, 62.0 mmol) dropwise. After 30 min BF$_3$OEt$_2$ (7.2 mL, 58.3 mmol) and (S)-propylene oxide (3 g, 51.6 mmol) in a minimum amount of THF were added. The reaction was stirred at −70° C. for 45 min. Saturated aqueous sodium bicarbonate was added at −70° C. followed by saturated aqueous ammonium chloride. The reaction was warmed to rt and diluted with diethyl ether. The phases were separated and the aqueous phase was extracted with diethyl ether (3×). The combined organic layers were washed with water then brine, dried over sodium sulfate, filtered and concentrated. The residue was subjected to silica chromatography using a 0-100% EtOAc/heptane gradient to afford 6.58 g of desired product (64%). GCMS m/z 197.1 [M-]. $^1$H NMR (400 MHz, CDCl$_3$) δ 4.82 (t, J=3.5 Hz, 1H), 4.19-4.37 (m, 2H), 3.81-4.03 (m, 2H), 3.51-3.60 (m, 1H), 2.32-2.49 (m, 2H), 2.02-2.10 (m, 1H), 1.70-1.92 (m, 2H), 1.49-1.69 (m, 3H), 1.24-1.31 (m, 3H).

Step 2: Synthesis of 2-(((S)-5-(2,2-diethoxyethoxy)hex-2-yn-1-yl)oxy)tetrahydro-2H-pyran (C24)

(2S)-6-((Tetrahydro-2H-pyran-2-yl)oxy)hex-4-yn-2-ol (C23) (6.5 g, 32.8 mmol) was dissolved in THF (33 mL) and cooled to 0° C. NaH (2.35 g, 58.8 mmol) was added in several portions. The reaction was warmed to rt for 30 min, then cooled back down to 0° C. Iodoacetaldehyde diethyl acetal (13.0 g, 53.3 mmol) was added dropwise then the reaction was heated to 55° C. for 18 h. The reaction was cooled back down to 0° C. and slowly quenched with saturated aqueous NH$_4$Cl. The layers were separated and the aqueous layer was extracted with ether (2×). The combined organic layers were washed with brine, dried over sodium sulfate, filtered and concentrated. The residue was subjected to silica gel column chromatography using a 0-100% EtOAc/heptane gradient to afford 5.54 g of desired product (54%). $^1$H NMR (400 MHz, CDCl$_3$) δ 4.80 (t, J=3.5 Hz, 1H), 4.58 (t, J=5.3 Hz, 1H), 4.13-4.34 (m, 2H), 3.83 (ddd, J=3.1, 8.8, 11.5 Hz, 1H), 3.46-3.75 (m, 7H), 2.52 (tdd, J=2.0, 4.8, 16.5 Hz, 1H), 2.32 (tdd, J=2.0, 7.4, 16.6 Hz, 1H), 1.67-1.90 (m, 2H), 1.46-1.67 (m, 4H), 1.26-1.32 (m, 1H), 1.25 (d, J=6.3 Hz, 3H), 1.21 (t, J=7.0 Hz, 6H).

Step 3: Synthesis of (S)-5-(2,2-diethoxyethoxy)hex-2-yn-1-ol (C25)

2-(((S)-5-(2,2-Diethoxyethoxy)hex-2-yn-1-yl)oxy)tetrahydro-2H-pyran (C24) (5.0 g, 15.9 mmol) was dissolved in EtOH (30 mL) and benzenesulfonic acid (285 mg, 1.8 mmol) was added. The reaction was stirred at rt for 5 hours. The reaction was then poured into a stirring solution of sodium hydrogen carbonate (800 mg, 9.54 mmol) in water (75 mL). The mixture was stirred for 5 min, then the layers were separated. The aqueous layer was extracted with ether (2×). The combined organic layers were washed with brine, dried over sodium sulfate, filtered and concentrated to yield 3.49 g of crude product (95%). The resulting material was carried on to the next step without further purification.

Step 4: Synthesis of (S)-(((5-(2,2-diethoxyethoxy)hex-2-yn-1-yl)oxy)methyl)benzene (C26)

To a solution of (S)-5-(2,2-diethoxyethoxy)hex-2-yn-1-ol (C25) (3.45 g, 15.0 mmol) in THF (60 mL) under a nitrogen atmosphere was added portion-wise NaH (730 mg, 18.3 mmol) at 0° C. After 10 min, benzyl bromide (2.88 g, 16.5 mmol) and tetrabutylammonium iodide (500 mg, 1.35 mmol) were added to the reaction and it was stirred for 18 hours at rt. The reaction was then quenched with saturated aqueous ammonium chloride. The phases were separated and the aqueous phase was extracted with EtOAc (3×). The combined organic layers were washed with brine, dried over sodium sulfate, filtered and concentrated. The residue was subjected to silica gel chromatography (gradient: 0-100% ethyl acetate in heptane) to yield 3.87 g of product as an oil (81%). $^1$H NMR (400 MHz, CDCl$_3$) δ 7.30-7.41 (m, 5H), 4.60 (s, 2H), 4.18 (t, J=2.2 Hz, 2H), 3.64-3.79 (m, 3H), 3.56-3.63 (m, 2H), 3.54 (d, J=5.5 Hz, 2H), 2.50-2.62 (m, 1H), 2.32-2.45 (m, 1H), 1.31-1.34 (m, 1H), 1.30 (d, J=6.2 Hz, 3H), 1.18-1.26 (m, 6H).

Step 5: Synthesis of (S,Z)-(((5-(2,2-diethoxyethoxy)hex-2-en-1-yl)oxy)methyl)benzene (C27)

A solution of (S)-(((5-(2,2-diethoxyethoxy)hex-2-yn-1-yl)oxy)methyl)benzene C26 (2.85 g, 8.89 mmol) in hexane (7 mL) was added to a mixture of Lindlar catalyst (102 mg, 5 mol %) and quinoline (1.20 g, 9.29 mmol) in hexane (20 mL) and octene (3 mL). The reaction was stirred in a Parr Reactor under H$_2$ (15 PSI) for 5 min at which point the pressure dropped to 0 PSI. This was repeated 3 times, until the pressure stopped dropping, at which point the reaction was stirred for 45 more min. The reaction was filtered through Celite, eluting with heptane, and then concentrated. The residue was then subjected to silica gel chromatography eluting with a 0-35% EtOAc/heptane gradient to afford the product as a colorless oil, 2.76 g (96%). $^1$H NMR (400 MHz, C$_6$D$_6$) δ 7.24-7.34 (m, 2H), 7.12-7.20 (m, 2H), 7.00-7.11 (m, 1H), 5.69-5.82 (m, 1H), 5.52-5.62 (m, 1H), 4.56-4.64 (m, 1H), 4.33 (s, 2H), 3.93-4.03 (m, 2H), 3.33-3.61 (m, 6H), 3.19-3.32 (m, 1H), 2.14-2.28 (m, 1H), 1.96-2.10 (m, 1H), 1.03-1.14 (m, 6H), 0.97 (d, J=5.9 Hz, 3H).

Step 6: Synthesis of (Z)-2-(((S,Z)-6-(benzyloxy)hex-4-en-2-yl)oxy)acetaldehyde oxime (C28)

To a solution of (S,Z)-(((5-(2,2-diethoxyethoxy)hex-2-en-1-yl)oxy)methyl)benzene (C27) (2.76 g, 8.53 mmol) in EtOH (19 mL) and water (4 mL) was added hydroxylamine hydrochloride (870 mg, 12.5 mmol). The reaction was heated to 70° C. for 80 min then cooled to rt. Sodium acetate (142 mg, 17.3 mmol) and water (3.2 mL) were then added and stirred for 10 min before the reaction mixture was concentrated. The residue was taken back up in water and DCM, the phases were separated and the aqueous phase was extracted with DCM (2×). The combined organics were washed with saturated aqueous sodium bicarbonate, brine, dried over sodium sulfate, filtered and concentrated. The residue was subjected to silica gel chromatography using a 0-50% EtOAc/heptane gradient to yield the product as a colorless oil, 2.05 g (91%).

Step 7: Synthesis of (3S,3aR,5S)-3-((benzyloxy)methyl)-5-methyl-3,3a,4,5-tetrahydro-7H-pyrano[3,4-c]isoxazole (C29)

To a solution of (Z)-2-(((S,Z)-6-(benzyloxy)hex-4-en-2-yl)oxy)acetaldehyde oxime (C28) (2.34 g, 8.86 mmol) in DCM (92 mL) was added Chlorox bleach (8.25% NaOCl, 10.5 mL, 12.9 mmol) dropwise and the reaction stirred for 10 min. The reaction was then diluted with water and DCM.

The phases were separated and the aqueous phase was extracted with DCM (2×). The combined organics were washed with saturated aqueous sodium bicarbonate, brine, dried over sodium sulfate, filtered and concentrated. The residue was subjected to silica gel chromatography using a 0-50% EtOAc/heptane gradient to yield the product as a colorless oil, 1.60 g (69%). $^1$H NMR (400 MHz, CDCl$_3$) δ 7.29-7.43 (m, 5H), 4.76-4.89 (m, 1H), 4.70 (d, J=13.7 Hz, 1H), 4.58 (q, J=12.0 Hz, 2H), 4.17 (dd, J=1.4, 13.5 Hz, 1H), 3.45-3.61 (m, 4H), 1.92-2.04 (m, 1H), 1.48-1.61 (m, J=10.9 Hz, 1H), 1.27 (d, J=6.2 Hz, 3H).

Step 8: Synthesis of (3S,3aR,5S,7aR)-3-((benzyloxy)methyl)-7a-(4-bromothiazol-2-yl)-5-methylhexahydro-1H-pyrano[3,4-c]isoxazole (C30)

2,4-Dibromothiazole (2.0 g, 8.2 mmol) was dissolved in a toluene:THF mixture (49.5 mL, 10:1 toluene:THF) and cooled to −78° C. Boron trifluoride etherate (1 mL, 8.1 mmol) was then added, followed by dropwise addition of nBuLi (3.0 mL, 7.5 mmol, 2.5 M), and the reaction was stirred for 30 min. (3S,3aR,5S)-3-((Benzyloxy)methyl)-5-methyl-3,3a,4,5-tetrahydro-7H-pyrano[3,4-c]isoxazole (C29) (1.6 g, 6.3 mmol) was dissolved in 5.5 mL of the toluene:THF solution and added to the reaction mixture dropwise. The reaction was allowed to stir at −78° C. for 45 min before being quenched with saturated aqueous ammonium chloride. The reaction was warmed to rt and diluted with water and EtOAc. The phases were separated and the aqueous phase was extracted with EtOAc (3×). The combined organics were washed with brine, dried over sodium sulfate, filtered and concentrated. The residue was subjected to silica gel chromatography (gradient: 0-45% ethyl acetate in heptane) to provide the desired product as a colorless solid, 2.05 g (77%). LCMS m/z 425.3 [M+H]$^+$. $^1$H NMR (400 MHz, CDCl$_3$) δ 7.17-7.31 (m, 5H), 6.50 (s, 1H), 4.43-4.53 (m, 1H), 4.34-4.43 (m, 1H), 3.86-4.01 (m, 2H), 3.75-3.84 (m, 1H), 3.55-3.67 (m, 1H), 3.46-3.55 (m, 2H), 3.18-3.30 (m, 1H), 1.53-1.65 (m, 1H), 1.23-1.38 (m, 1H), 1.17 (d, J=6.2 Hz, 3H).

Step 9: Synthesis of (S)-1-((2S,4R,5R)-5-amino-5-(4-bromothiazol-2-yl)-2-methyltetrahydro-2H-pyran-4-yl)-2-(benzyloxy)ethan-1-ol (C31)

(3S,3aR,5S,7aR)-3-((Benzyloxy)methyl)-7a-(4-bromothiazol-2-yl)-5-methyl hexahydro-1H-pyrano[3,4-c]isoxazole (C30) (1.7 g, 4.0 mmol) was dissolved in acetonitrile (37 mL) and water (3 mL). Mo(CO)$_6$ (0.54 g, 2.0 mmol) was added to the solution and heated to 80° C. for 2 h. The reaction was cooled to 0° C. and NaBH$_4$ (2 equiv) was added in one portion to the reaction mixture. The reaction mixture was left stirring at 0° C. for 1 h. The resulting brown heterogeneous solution was filtered through a Celite pad to remove the brown solids. The Celite pad was washed with DCM (3×). The resulting organic filtrate was washed with brine (1×), dried over Na$_2$SO$_4$, filtered and concentrated under reduced pressure. A black solid was obtained and this solid was treated with MeOH. The resulting methanolic solution of organic crude was concentrated under reduced pressure after stirring at rt for 10 min to yield a brown solid, which was treated with MeOH (2×) and concentrated after stirring at rt for 10 min, each time. The residue was subjected to silica gel chromatography (gradient: 0-100% ethyl acetate in heptane) to yield 1.37 g (80%). LCMS m/z 427.3 [M+H]$^+$. $^1$H NMR (400 MHz, CDCl$_3$) δ 7.25-7.40 (m, 5H), 7.17-7.24 (m, 1H), 4.49 (s, 2H), 3.77-3.85 (m, 1H), 3.73 (d, J=11.3 Hz, 1H), 3.57-3.69 (m, 1H), 3.53 (d, J=11.3 Hz, 1H), 3.34-3.45 (m, 2H), 2.55-2.70 (m, 2H), 2.42-2.52 (m, 1H), 1.82 (s, 1H), 1.46-1.58 (m, 1H), 1.28 (d, J=6.2 Hz, 3H).

Step 10: Synthesis of N-(((3R,4R,6S)-4-((S)-2-(benzyloxy)-1-hydroxyethyl)-3-(4-bromothiazol-2-yl)-6-methyltetrahydro-2H-pyran-3-yl)carbamothioyl)benzamide (C32)

(S)-1-((2S,4R,5R)-5-Amino-5-(4-bromothiazol-2-yl)-2-methyltetrahydro-2H-pyran-4-yl)-2-(benzyloxy)ethan-1-ol (C31) (1.37 g, 3.2 mmol) was dissolved in DCM (32 mL) and benzoyl isocyanate (0.43 mL, 3.1 mmol) was added. The reaction mixture was stirred for 18 h and then concentrated in vacuo. The crude product was taken on to the next step without further purification. LCMS m/z 589.2 [M−H$^+$].

Step 11: Synthesis of N-((4S,4aR,6S,8aR)-4-((benzyloxy)methyl)-8a-(4-bromothiazol-2-yl)-6-methyl-4,4a,5,6,8,8a-hexahydropyrano[3,4-d][1,3]oxazin-2-yl)benzamide (C33)

To a solution of N-(((3R,4R,6S)-4-((S)-2-(benzyloxy)-1-hydroxyethyl)-3-(4-bromothiazol-2-yl)-6-methyltetrahydro-2H-pyran-3-yl)carbamothioyl)benzamide (C32) (1.9 g, 3.2 mmol) in acetonitrile (32 mL) was added EDC (0.67 g, 3.5 mmol). The reaction was stirred for 18 h then concentrated. The residue was taken up in EtOAc and water. The phases were separated and the aqueous phase was extracted with EtOAc. The combined organics were washed with brine, dried over Na$_2$SO$_4$, filtered, and concentrated. The residue was subjected to silica gel chromatography (gradient: 0-50% ethyl acetate in heptane) to yield the product 1.25 g (71%). LCMS m/z 558.2 [M−H$^+$]. $^1$H NMR (400 MHz, CDCl$_3$) b 12.08 (br. s., 1H), 8.26 (d, J=7.4 Hz, 2H), 7.25-7.56 (m, 7H), 4.56-4.63 (m, 1H), 4.44-4.54 (m, 1H), 4.37 (dt, J=2.3, 6.4 Hz, 1H), 4.03-4.10 (m, 1H), 3.90-4.00 (m, 1H), 3.64-3.78 (m, 2H), 3.56-3.64 (m, 1H), 3.08 (s, 1H), 1.53-1.64 (m, 1H), 1.35-1.44 (m, 1H), 1.26-1.33 (m, 2H), 1.21-1.25 (m, 3H).

Step 12: Synthesis of N-((4S,4aR,6S,8aR)-8a-(4-bromothiazol-2-yl)-4-(hydroxymethyl)-6-methyl-4,4a,5,6,8,8a-hexahydropyrano[3,4-d][1,3]oxazin-2-yl)benzamide (C34)

N-((4S,4aR,6S,8aR)-4-((Benzyloxy)methyl)-8a-(4-bromothiazol-2-yl)-6-methyl-4,4a,5,6,8,8a-hexahydropyrano[3,4-d][1,3]oxazin-2-yl)benzamide (C33) (1.15 g, 1.82 mmol) was dissolved in DCM (15.2 mL) and triflic acid (0.56 mL, 6.36 mmol) was added dropwise. The reaction was stirred at rt for 20 min before being cooled to 0° C. and quenched with 1N NaOH, slowly, until the solution was basic. The phases were separated and the aqueous phase was extracted with DCM (1×). The combined organics were washed with brine, dried over Na$_2$SO$_4$, filtered, and concentrated. The residue was subjected to silica gel chromatography (gradient: 0-100% ethyl acetate in heptane) to yield 0.8 g (94%). LCMS m/z 468.2 [M+H]$^+$. $^1$H NMR (400 MHz, CDCl$_3$) δ 12.01 (br. s., 1H), 8.15 (d, J=7.0 Hz, 2H), 7.44 (d, J=7.4 Hz, 1H), 7.32-7.40 (m, 2H), 7.20 (s, 1H), 4.20-4.27 (m, 1H), 3.95-4.01 (m, 1H), 3.85-3.93 (m, 2H), 3.59-3.70 (m, 2H), 2.95-3.04 (m, 1H), 2.33-2.48 (m, 1H), 1.59-1.69 (m, 1H), 1.31-1.44 (m, 1H), 1.14-1.25 (m, 3H).

Step 13: Synthesis of N-((4S,4aR,6S,8aR)-8a-(4-bromothiazol-2-yl)-4-(fluoromethyl)-6-methyl-4,4a,5,6,8,8a-hexahydropyrano[3,4-d][1,3]oxazin-2-yl)benzamide (C35)

N-((4S,4aR,6S,8aR)-8a-(4-Bromothiazol-2-yl)-4-(hydroxymethyl)-6-methyl-4,4a,5,6,8,8a-hexahydropyrano[3, 4-d][1,3]oxazin-2-yl)benzamide (C34) (99 mg, 0.21 mmol) was dissolved in THF (2.1 mL) under a nitrogen atmosphere and cooled to 0° C. TEA (0.27 mL, 1.91 mmol), TEA-3HF (0.1 mL, 0.64 mmol), and perfluorobutanesulfonyl fluoride (74 mg, 0.64 mmol) were added sequentially. The reaction was warmed to rt and stirred for 45 min. Kryptofix (480 mg, 1.27 mmol) and KF (58 mg, 1.27 mmol) were then added, and the reaction stirred for 5 min. The reaction was then diluted with EtOAc and saturated aqueous sodium bicarbonate. The phases were separated and the aqueous phase was extracted with EtOAc (2×). The combined organics were washed with brine, dried over $Na_2SO_4$, filtered, and concentrated. The residue was subjected to silica gel chromatography (gradient: 0-50% ethyl acetate in heptane) to yield the product 81 mg (81%). LCMS m/z 470.2 [M+H$^+$]. $^1$H NMR (400 MHz, CDCl$_3$) δ 12.00-12.22 (m, 1H), 8.18-8.28 (m, 2H), 7.47-7.57 (m, 1H), 7.44 (d, J=7.8 Hz, 2H), 7.28 (s, 1H), 4.61 (d, J=10.2 Hz, 2H), 4.38-4.47 (m, 1H), 4.01-4.09 (m, 1H), 3.92-4.01 (m, 1H), 3.66-3.78 (m, 1H), 3.04-3.19 (m, 1H), 1.67-1.77 (m, 1H), 1.43-1.57 (m, 1H), 1.24-1.30 (m, 3H).

Step 14: Synthesis of N-((4S,4aR,6S,8aR)-8a-(4-((2,4-dimethoxyphenyl)amino) thiazol-2-yl)-4-(fluoromethyl)-6-methyl-4,4a,5,6,8,8a-hexahydropyrano [3,4-d][1,3]oxazin-2-yl)benzamide (C36)

A flask under nitrogen atmosphere was charged with Pd$_2$(dba)$_3$ (8.0 mg, 9 μmol), tButyl XPhos (12 mg, 0.027 mmol), and NaOtBu (42 mg, 0.43 mmol). The flask was purged with nitrogen and vacuum (3×). Anhydrous dioxane (1 mL) was added and the reaction was heated to 95° C. In a separate flask under nitrogen atmosphere was added N-((4S,4aR,6S,8aR)-8a-(4-bromothiazol-2-yl)-4-(fluoromethyl)-6-methyl-4,4a,5,6,8,8a-hexahydropyrano[3,4-d][1,3]oxazin-2-yl)benzamide (C35) (81 mg, 0.17 mmol), 2,4-dimethoxybenzylamine (50 mg, 0.29 mmol) and dioxane (1 mL). This solution was added to the reaction at 95° C. after 5 min of stirring. The reaction was stirred for 15 min at 95° C. then cooled to rt. Celite was then added to the reaction, followed by water. The mixture was then filtered through a pad of Celite, DCM was used as an eluent (3×). The pH of the resulting aq. layer was measured to be pH 12. The layers were isolated and the resulting organic layer was washed with H$_2$O (3×) until a pH neutral was achieved on the resulting aqueous layer from the extractions. Then the resulting organic layer was washed with 5% aqueous citric acid (2×). The pH of the resulting aqueous layers was measured to be pH 4 on the first wash and pH 2 on the second wash. The resulting organic layer was then washed with saturated aqueous NaHCO$_3$ (2×), brine (1×), dried over Na$_2$SO$_4$ and filtered. The material was carried on to the next step without further purification, 90 mg (94%). LCMS m/z 555.4 [M+H]$^+$.

Step 15: Synthesis of N-(2-((4S,4aR,6S,8aR)-2-benzamido-4-(fluoromethyl)-6-methyl-4,4a,5,6-tetrahydropyrano[3,4-d][1,3]oxazin-8a(8H)-yl)thiazol-4-yl)-5-(difluoromethoxy)-N-(2,4-dimethoxybenzyl) picolinamide (C37)

5-(Difluoromethoxy)picolinic acid (49 mg, 0.26 mmol) was suspended in EtOAc (0.32 mL) and TEA (90 μL, 0.65 mmol). T3P (50% wt in EtOAc, 0.39 mL, 0.65 mmol) was added and the reaction stirred at 60° C. for 20 min. N-((4S,4aR,6S,8aR)-8a-(4-((2,4-dimethoxyphenyl)amino)thiazol-2-yl)-4-(fluoromethyl)-6-methyl-4,4a,5,6,8,8a-hexahydropyrano[3,4-d][1,3]oxazin-2-yl)benzamide (C36) (90 mg, 0.16 mmol) was then added and the reaction mixture was stirred at 60° C. for 1 h. The reaction mixture was then cooled to rt, diluted with EtOAc and quenched with water. The layers were separated and the aqueous layer extracted with EtOAc (2×). The combined organics were washed with brine, dried over sodium sulfate, filtered and concentrated. The material was taken on to the next step without further purification. LCMS m/z 726.4 [M+H]$^+$.

Step 16: Synthesis of N-(2-((4S,4aR,6S,8aR)-2-benzamido-4-(fluoromethyl)-6-methyl-4,4a,5,6-tetrahydropyrano[3,4-d][1,3]oxazin-8a(8H)-yl)thiazol-4-yl)-5-(difluoromethoxy) picolinamide (C38)

N-(2-((4S,4aR,6S,8aR)-2-Benzamido-4-(fluoromethyl)-6-methyl-4,4a,5,6-tetrahydropyrano[3,4-d][1,3]oxazin-8a(8H)-yl)thiazol-4-yl)-5-(difluoromethoxy)-N-(2,4-dimethoxybenzyl)picolinamide (C37) (115 mg, 01.16 mmol) was dissolved in DCM (0.79 mL) and TFA (0.30 mL, 3.96 mmol) was added. The reaction mixture was stirred at rt for 18 h. The reaction mixture was concentrated and the residue was re-dissolved in EtOAc and saturated aqueous sodium bicarbonate. The aqueous layer was extracted with EtOAc (3×). The combined organics were washed with brine, dried over sodium sulfate, filtered and concentrated. The residue was subjected to silica gel chromatography (gradient: 0-100% ethyl acetate in heptane) to afford 42 mg of a colorless oil (46%). LCMS m/z 576.3 [M+H]$^+$. $^1$H NMR (400 MHz, CDCl$_3$) δ 12.09 (br. s., 1H), 10.44 (s, 1H), 8.46-8.51 (m, 1H), 8.29-8.34 (m, 1H), 8.21-8.29 (m, 1H), 7.83 (s, 1H), 7.63-7.74 (m, 1H), 7.49-7.57 (m, 1H), 7.40-7.48 (m, 2H), 6.45-6.85 (m, 1H), 4.69-4.77 (m, 1H), 4.57-4.67 (m, 1H), 4.47-4.56 (m, 1H), 4.04 (d, J=2.4 Hz, 1H), 3.65-3.80 (m, 1H), 3.03-3.11 (m, 1H), 1.69-1.88 (m, 1H), 1.50-1.63 (m, 2H), 1.22-1.35 (m, 4H).

Step 17: Synthesis of N-(2-((4S,4aR,6S,8aR)-2-amino-4-(fluoromethyl)-6-methyl-4,4a,5,6-tetrahydropyrano[3,4-d][1,3]oxazin-8a(8H)-yl)thiazol-4-yl)-5-(difluoromethoxy) picolinamide (6)

N-(2-((4S,4aR,6S,8aR)-2-Benzamido-4-(fluoromethyl)-6-methyl-4,4a,5,6-tetrahydropyrano[3,4-d][1,3]oxazin-8a(8H)-yl)thiazol-4-yl)-5-(difluoromethoxy) picolinamide (C38) (42 mg, 0.07 mmol) was dissolved in MeOH (1.46 mL) and DBU (14 μL, 0.09 mmol) was added. The reaction mixture was heated to 60° C. for 2 h. The reaction mixture was concentrated and the residue was subjected to silica gel chromatography using a 0-10% MeOH/DCM gradient to afford product as a colorless solid, 17 mg (50%). LCMS m/z 472.3 [M+H]$^+$. $^1$H NMR (400 MHz, CD$_3$OD) δ 8.58 (d, J=2.7 Hz, 1H), 8.29 (d, J=8.6 Hz, 1H), 7.83 (dd, J=2.7, 9.0 Hz, 1H), 7.75 (s, 1H), 6.89-7.31 (m, 1H), 4.57-4.64 (m, 1H), 4.45-4.53 (m, 1H), 4.12-4.23 (m, 1H), 3.89-3.98 (m, 1H), 3.77-3.86 (m, 1H), 3.62-3.73 (m, 1H), 2.83-2.95 (m, 1H), 1.58-1.70 (m, 1H), 1.29-1.43 (m, 1H), 1.25 (d, J=6.2 Hz, 3H).

Example 7

N-(2-((4S,4aR,6S,8aR)-2-amino-6-methyl-4-(trifluoromethyl)-4,4a,5,6-tetrahydropyrano [3,4-d][1,3] oxazin-8a(8H)-yl)thiazol-4-yl)-5-(difluoromethoxy) picolinamide

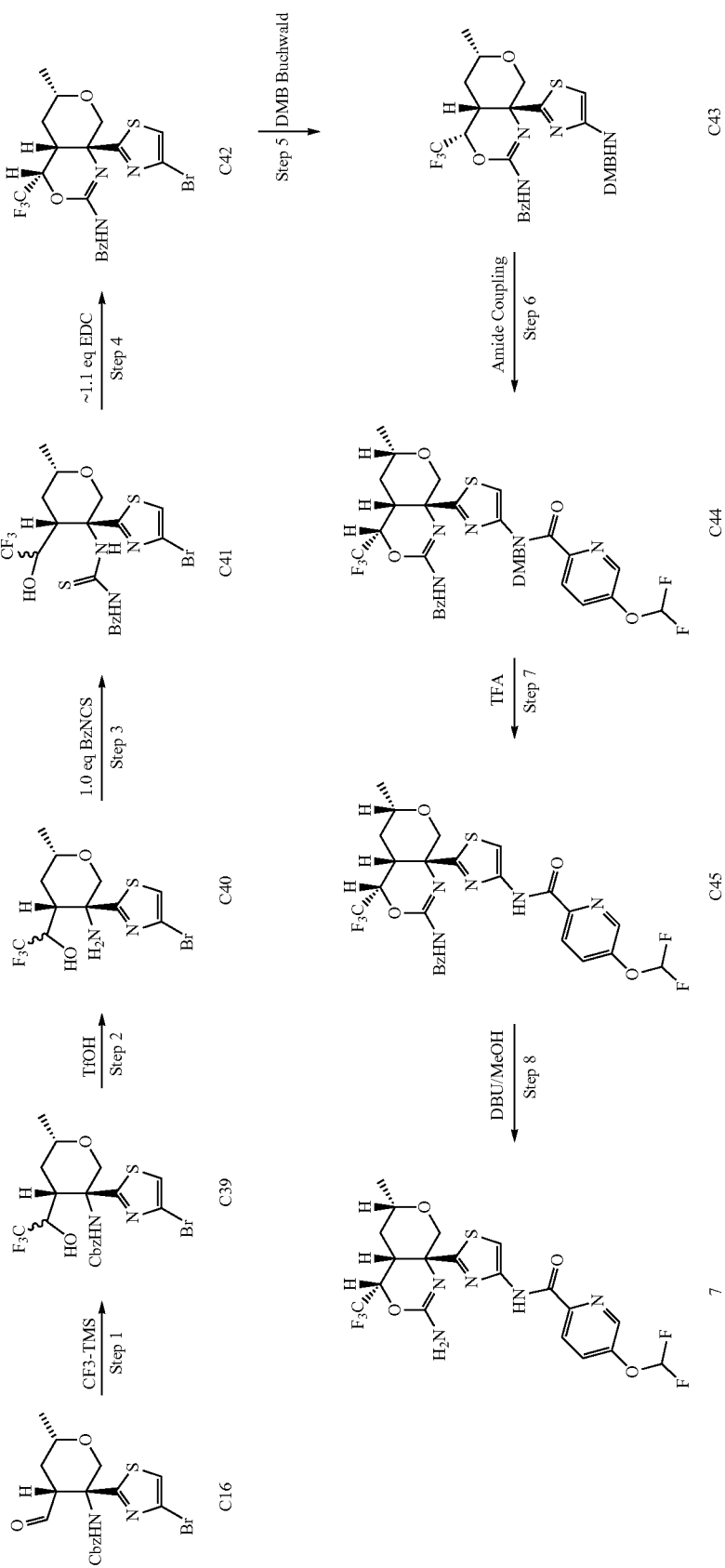

Step 1: Synthesis of benzyl ((3R,4R,6S)-3-(4-bromothiazol-2-yl)-6-methyl-4-((R)-2,2,2-trifluoro-1-hydroxyethyl)tetrahydro-2H-pyran-3-yl)carbamate (C39)

Benzyl ((3R,4R,6S)-3-(4-bromothiazol-2-yl)-4-formyl-6-methyltetrahydro-2H-pyran-3-yl)carbamate (C16) (600 mg, 1.37 mmol) was dissolved in THF (18 mL) under nitrogen atmosphere and cooled to 0° C. (Trimethylsilyl)trifluoromethane (529 mg, 3.68 mmol) was added, followed by the dropwise addition of TBAF (0.50 mL, 0.5 mmol, 1M in THF). The reaction was stirred at rt for 2 h. The reaction was concentrated and the residue taken up in DCM and aqueous ammonium chloride. The layers were separated and the aqueous layer was extracted with DCM. The combined organics were washed with brine, dried over sodium sulfate, filtered and concentrated. The residue was subjected to silica gel chromatography using a 0-100% EtOAc/heptane gradient to afford product as a colorless solid, 231 mg (33.2%). LCMS m/z 511.1 [M+H]$^+$. $^1$H NMR (400 MHz, CDCl$_3$) δ 7.25-7.36 (m, 5H), 7.15 (s, 1H), 6.11-6.26 (m, 1H), 4.94-5.15 (m, 2H), 4.22-4.43 (m, 2H), 3.63 (d, J=12.1 Hz, 2H), 2.79-2.97 (m, 1H), 2.54-2.69 (m, 1H), 1.67-1.89 (m, 2H), 1.15-1.27 (m, 3H).

Step 2: Synthesis of 1-((2S,4R,5R)-5-amino-5-(4-bromothiazol-2-yl)-2-methyl tetrahydro-2H-pyran-4-yl)-2,2,2-trifluoroethan-1-ol (C40)

Benzyl ((3R,4R,6S)-3-(4-bromothiazol-2-yl)-6-methyl-4-((R)-2,2,2-trifluoro-1-hydroxyethyl)tetrahydro-2H-pyran-3-yl)carbamate (C39) (228 mg, 0.45 mmol) was dissolved in DCM (1.5 mL) and treated with triflic acid (0.17 mL, 1.92 mmol). The reaction was stirred at rt for 15 min then diluted with DCM and saturated aqueous sodium bicarbonate. The aqueous layer was extracted with DCM (2×). The combined organics were washed with brine, dried over sodium sulfate, filtered and concentrated. The material was taken on to the next step without further purification. LCMS m/z 377.2 [M+H]$^+$.

Step 3: Synthesis of N-(((3R,4R,6S)-3-(4-bromothiazol-2-yl)-6-methyl-4-(2,2,2-trifluoro-1-hydroxyethyl)tetrahydro-2H-pyran-3-yl)carbamothioyl)benzamide (C41)

1-((2S,4R,5R)-5-Amino-5-(4-bromothiazol-2-yl)-2-methyltetrahydro-2H-pyran-4-yl)-2,2,2-trifluoroethan-1-ol (C40) (196 mg, 0.52 mmol) was dissolved in DCM (5.0 mL) under nitrogen atmosphere. Benzoyl isothiocyanate (60 μL, 0.45 mmol) was added in one portion and the reaction mixture was stirred at 35° C. for 18 h. The reaction mixture was then concentrated and the residue was subjected to silica gel chromatography (gradient: 0-45% ethyl acetate in heptane) to yield a pale yellow solid, 206 mg (73%). LCMS m/z 538.2 [M+H]$^+$. $^1$H NMR (400 MHz, CDCl$_3$) δ 11.85 (s, 1H), 8.82-9.01 (m, 1H), 7.79-7.96 (m, 2H), 7.59-7.73 (m, 1H), 7.47-7.58 (m, 2H), 7.28 (s, 1H), 5.00-5.08 (m, 1H), 4.93-5.00 (m, 1H), 3.74-3.84 (m, 2H), 3.25 (d, J=7.0 Hz, 1H), 2.88 (dd, J=4.1, 12.7 Hz, 1H), 1.86-2.10 (m, 2H), 1.35 (d, J=5.9 Hz, 3H).

Step 4: Synthesis of N-((4S,4aR,6S,8aR)-8a-(4-bromothiazol-2-yl)-6-methyl-4-(trifluoromethyl)-4,4a,5,6,8,8a-hexahydropyrano[3,4-d][1,3]oxazin-2-yl)benzamide (C42)

N-(((3R,4R,6S)-3-(4-Bromothiazol-2-yl)-6-methyl-4-(2,2,2-trifluoro-1-hydroxyethyl) tetrahydro-2H-pyran-3-yl)carbamothioyl)benzamide (C41) (200 mg, 0.37 mmol) was dissolved in acetonitrile (0.34 mL) and EDC (85 mg, 0.44 mmol) was added. The reaction was stirred for 18 h then concentrated. The residue was taken up in EtOAc and water. The phases were separated and the aqueous phase was extracted with EtOAc (2×). The combined organics were washed with brine, dried over sodium sulfate, filtered and concentrated. The residue was subjected to silica gel chromatography using a 0-40% EtOAc/heptane gradient to afford product as a colorless solid, 142 mg (76%). LCMS m/z 506.2 [M+H]$^+$. $^1$H NMR (400 MHz, CDCl$_3$) δ 11.96-12.06 (m, 1H), 8.14-8.26 (m, 2H), 7.44-7.52 (m, 1H), 7.39 (d, J=7.8 Hz, 2H), 7.25 (s, 1H), 4.38-4.47 (m, 1H), 3.93 (s, 2H), 3.62-3.72 (m, 1H), 3.21-3.31 (m, J=2.3, 5.1 Hz, 1H), 1.76-1.85 (m, 1H), 1.51-1.61 (m, 1H), 1.22 (d, J=6.2 Hz, 3H).

Step 5: Synthesis of N-((4S,4aR,6S,8aR)-8a-(4-((2,4-dimethoxybenzyl) amino)thiazol-2-yl)-6-methyl-4-(trifluoromethyl)-4,4a,5,6,8,8a-hexahydropyrano[3,4-d][1,3]oxazin-2-yl)benzamide (C43)

A flask under nitrogen atmosphere was charged with Pd$_2$(dba)$_3$ (12.5 mg, 14 μmol), tButyl XPhos (18 mg, 42 μmol), and NaOtBu (66 mg, 0.68 mmol). The flask was purged with nitrogen and vacuum (3×). Anhydrous dioxane (1 mL) was added and the reaction mixture heated to 95° C. In a separate flask under nitrogen atmosphere was added N-((4S,4aR,6S,8aR)-8a-(4-bromothiazol-2-yl)-6-methyl-4-(trifluoromethyl)-4,4a,5,6,8,8a-hexahydropyrano[3,4-d][1,3]oxazin-2-yl)benzamide (C42) (138 mg, 0.27 mmol), 2,4-dimethoxybenzylamine (78 mg, 0.46 mmol) and dioxane (1.5 mL). This solution was added to the reaction at 95° C. after 5 min of stirring. The reaction mixture was stirred for 15 min at 95° C. then cooled to rt. Celite was then added to the reaction mixture, followed by water. The mixture was then filtered through a pad of Celite, DCM was used as an eluent (3×). The pH of the resulting aq. layer was measured to be pH 12. The layers were isolated and the resulting organic layer was washed with H$_2$O (3×) until a neutral pH was achieved on the resulting aqueous layer from the extractions. Then the resulting organic layer was washed with 5% aqueous citric acid (2×). The pH of the resulting aqueous layers was measured to be pH 4 on the first wash and pH 2 on the second wash. The resulting organic layer was then washed with saturated aqueous NaHCO$_3$ (2×), brine (1×), dried over Na$_2$SO$_4$ and filtered. The material was carried on to the next step without further purification, 97 mg (60%). LCMS m/z 591.3 [M+H]$^+$.

Step 6: Synthesis of N-(2-((4S,4aR,6S,8aR)-2-benzamido-6-methyl-4-(trifluoromethyl)-4,4a,5,6-tetrahydropyrano[3,4-d][1,3]oxazin-8a(8H)-yl)thiazol-4-yl)-5-(difluoromethoxy)-N-(2,4-dimethoxybenzyl) picolinamide (C44)

5-(Difluoromethoxy)picolinic acid (19 mg, 0.10 mmol) was suspended in EtOAc (0.12 mL) and TEA (35 μL, 0.25 mmol). T3P (50% wt in EtOAc, 0.15 mL, 0.25 mmol) was added and the reaction stirred at 60° C. for 20 min. N-((4S,4aR,6S,8aR)-8a-(4-((2,4-Dimethoxybenzyl)amino)thiazol-2-yl)-6-methyl-4-(trifluoromethyl)-4,4a,5,6,8,8a-hexahydropyrano[3,4-d][1,3]oxazin-2-yl)benzamide (C43) (37 mg, 0.06 mmol) was then added and the reaction stirred at 60° C. for 1 h. The reaction was then cooled to rt, diluted with EtOAc and quenched with water. The layers were separated and the aqueous layer extracted with EtOAc (2×). The combined organics were washed with brine, dried over sodium sulfate, filtered and concentrated. The material was taken on to the next step without further purification, 44 mg (92%). LCMS m/z 762.3 [M+H]+.

Step 7: Synthesis of N-(2-((4S,4aR,6S,8aR)-2-benzamido-6-methyl-4-(trifluoromethyl)-4,4a,5,6-tetrahydropyrano[3,4-d][1,3]oxazin-8a(8H)-yl)thiazol-4-yl)-5-(difluoromethoxy) picolinamide (C45)

N-(2-((4S,4aR,6S,8aR)-2-Benzamido-6-methyl-4-(trifluoromethyl)-4,4a,5,6-tetrahydropyrano[3,4-d][1,3]oxazin-8a(8H)-yl)thiazol-4-yl)-5-(difluoromethoxy)-N-(2,4-dimethoxybenzyl)picolinamide (C44) (44 mg, 0.06 mmol) was dissolved in DCM (0.3 mL) and TFA (0.11 mL, 1.44 mmol) was added. The reaction mixture was stirred at rt for 18 h. The reaction was concentrated and the residue re-dissolved in EtOAc and saturated aqueous sodium bicarbonate. The aqueous layer was extracted with EtOAc (3×). The combined organics were washed with brine, dried over sodium sulfate, filtered and concentrated to give 34 mg of crude product (96%). LCMS m/z 612.4 [M+H]+.

Step 8: Synthesis of N-(2-((4S,4aR,6S,8aR)-2-amino-6-methyl-4-(trifluoromethyl)-4,4a,5,6-tetrahydropyrano[3,4-d][1,3]oxazin-8a(8H)-yl)thiazol-4-yl)-5-(difluoromethoxy) picolinamide (7)

N-(2-((4S,4aR,6S,8aR)-2-Benzamido-6-methyl-4-(trifluoromethyl)-4,4a,5,6-tetrahydropyrano[3,4-d][1,3]oxazin-8a(8H)-yl)thiazol-4-yl)-5-(difluoromethoxy) picolinamide (C45) (34 mg, 0.06 mmol) was dissolved in MeOH (1.11 mL) and DBU (10 µL, 0.07 mmol) was added. The reaction was heated to 60° C. for 2 h. The reaction was concentrated and the residue was subjected to silica gel chromatography using a 0-10% MeOH/DCM gradient to afford product as a colorless solid, 21 mg (74%). LCMS m/z 508.2 [M+H]+. $^1$H NMR (400 MHz, CDCl$_3$) δ 10.48 (s, 1H), 8.55 (d, J=2.7 Hz, 1H), 8.33-8.43 (m, 1H), 7.83 (s, 1H), 7.74 (dd, J=2.7, 8.6 Hz, 1H), 6.44-6.94 (m, 1H), 4.56 (br. s, 2H), 4.29-4.38 (m, 1H), 3.92-4.01 (m, 1H), 3.82-3.92 (m, 1H), 3.64-3.76 (m, 1H), 2.83-3.20 (m, 1H), 1.68-1.87 (m, 1H), 1.51-1.67 (m, 1H), 1.29-1.41 (m, 3H).

Preparation P3:
5-(difluoromethoxy)-3-methylpicolinic acid (C13)

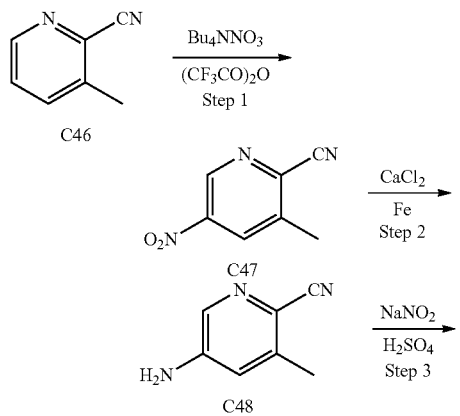

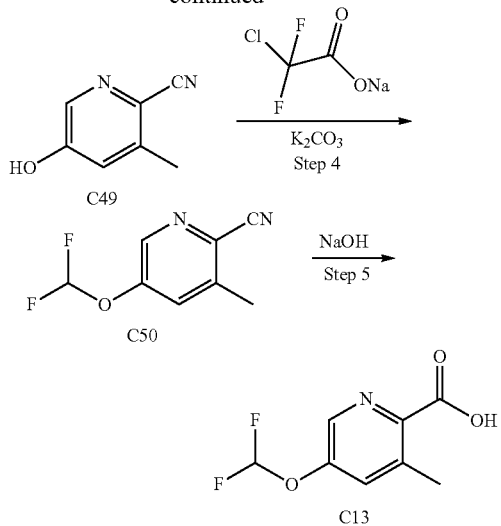

Step 1: Synthesis of 3-methyl-5-nitropicolinonitrile (C47)

A mixture of 3-methylpicolinonitrile (C46) (128 g, 1.08 mol) and tetrabutylammonium nitrate (363 g, 1.19 mol) in tert-butyl methyl ether (1.3 L) was cooled to 4° C. Trifluoroacetic anhydride (171 mL, 1.21 mol) was added, and the reaction mixture was allowed to stir at room temperature for 60 hours. It was then adjusted to a pH of approximately 7 by addition of 20% aqueous sodium hydroxide solution, and extracted with dichloromethane (3×1 L). The combined organic layers were dried, filtered, and concentrated in vacuo; purification via silica gel chromatography (Gradient: 0% to 10% ethyl acetate in petroleum ether) afforded 3-methyl-5-nitropicolinonitrile as a yellow solid. Yield: 70 g, 0.43 mmol, 40%. $^1$H NMR (400 MHz, CDCl$_3$) δ 9.31-9.36 (m, 1H), 8.47-8.52 (m, 1H), 2.74 (s, 3H).

Step 2: Synthesis of 5-amino-3-methylpicolinonitrile (C48)

To a solution of 3-methyl-5-nitropicolinonitrile (C47) (40.0 g, 245 mmol) in ethanol (630 mL) and water (70 mL) was added calcium chloride (13.6 g, 123 mmol), followed by iron powder (123 g, 2.20 mol), and the reaction mixture was stirred overnight at room temperature. After filtration of the reaction mixture, the filtrate was concentrated in vacuo, and the residue was purified by chromatography on silica gel (Gradient: 10% to 50% ethyl acetate in petroleum ether). 5-Amino-3-methylpicolinonitrile was obtained as a yellow solid. Yield: 20.0 g, 150 mmol, 61%. $^1$H NMR (400 MHz, CDCl$_3$) δ 7.94 (d, J=2.5 Hz, 1H), 6.81 (d, J=2.5 Hz, 1H), 4.07-4.19 (br s, 2H), 2.45 (s, 3H).

Step 3: Synthesis of 5-hydroxy-3-methylpicolinonitrile (C49)

Sodium nitrite (1.6 M aqueous solution containing 10.3 g of sodium nitrite, 149 mmol) was slowly added to a 0° C. solution of 5-amino-3-methylpicolinonitrile (C48) (18.0 g, 135 mmol) in water (243 mL) and concentrated sulfuric acid (67.5 mL). The reaction mixture was warmed to room temperature and then stirred at 100° C. for 3 hours, whereupon it was cooled and extracted with ethyl acetate (3×75 mL). The combined organic layers were washed with water (2×75 mL) and with saturated aqueous sodium chloride solution (2×75 mL), dried, filtered, and concentrated under reduced pressure to afford 5-hydroxy-3-methylpicolinonitrile as a yellow solid. Yield: 16 g, 120 mmol, 89%. $^1$H NMR (400 MHz, DMSO-$d_6$) δ 11.07 (br s, 1H), 8.08 (d, J=2.6 Hz, 1H), 7.20 (d, J=2.3 Hz, 1H), 2.40 (s, 3H).

Step 4: Synthesis of 5-(difluoromethoxy)-3-methylpicolinonitrile (C50)

A mixture of 5-hydroxy-3-methylpicolinonitrile (C49) (5.70 g, 42.5 mmol), sodium chlorodifluoroacetate (13.0 g, 85.3 mmol), and potassium carbonate (17.6 g, 127 mmol) in N,N-dimethylformamide (175 mL) was stirred for 30 minutes at 100° C. The reaction mixture was then diluted with ethyl acetate (400 mL), and sequentially washed with saturated aqueous ammonium chloride solution (3×200 mL) and saturated aqueous sodium chloride solution (3×200 mL). The combined aqueous layers were extracted with ethyl acetate (200 mL), and the combined organic layers were dried over sodium sulfate, filtered, and concentrated in vacuo. Silica gel chromatography (Gradient: 5% to 15% ethyl acetate in petroleum ether) provided 5-(difluoromethoxy)-3-methylpicolinonitrile as a colorless oil. Yield: 3.9 g, 21 mmol, 49%. $^1$H NMR (400 MHz, CDCl$_3$) δ 8.39 (br d, J=2.1 Hz, 1H), 7.43-7.47 (m, 1H), 6.64 (t, $J_{HF}$=71.5 Hz, 1H), 2.59 (s, 3H).

Step 5: Synthesis of 5-(difluoromethoxy)-3-methylpicolinic acid (C13)

Aqueous sodium hydroxide solution (1 M, 124 mL, 124 mmol) was added to a solution of 5-(difluoromethoxy)-3-methylpicolinonitrile (C50) (7.60 g, 41.3 mmol) in ethanol (200 mL), and the reaction mixture was stirred for 16 hours at 70° C. It was then diluted with tert-butyl methyl ether (200 mL) and extracted with water (2×100 mL). The combined aqueous layers were washed with tert-butyl methyl ether (100 mL), acidified to pH 2 with 1 M aqueous hydrochloric acid, and extracted with tert-butyl methyl ether (2×200 mL). The combined organic extracts were dried over sodium sulfate, filtered, and concentrated in vacuo to afford 5-(difluoromethoxy)-3-methylpicolinic acid as a white solid. Yield: 6.6 g, 32 mmol, 77%. LCMS m/z 203.7 [M+H]$^+$. $^1$H NMR (400 MHz, CD$_3$OD) δ 8.32 (br d, J=2.1 Hz, 1H), 7.58-7.62 (m, 1H), 7.06 (t, $J_{HF}$=72.7 Hz, 1H), 2.64 (s, 3H).

Preparation P4: 5-(difluoromethoxy)picolinic acid (C9)

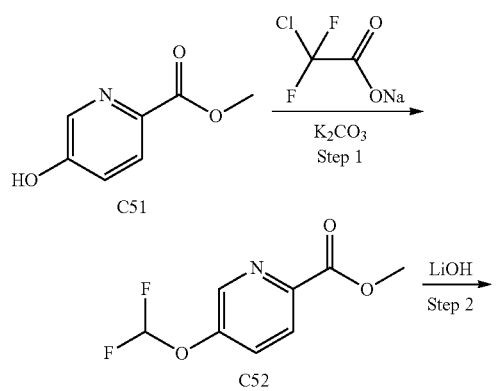

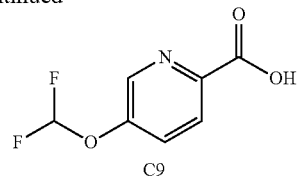

Step 1: Synthesis of methyl 5-(difluoromethoxy)picolinate (C52)

Potassium carbonate (45.1 g, 326 mmol) was added to a solution of methyl 5-hydroxypicolinate (C51) (20 g, 130 mmol) in N,N-dimethylformamide (500 mL), and the reaction mixture was stirred at room temperature for 0.5 hours. Sodium chloro(difluoro)acetate (63.7 g, 418 mmol) was introduced, and the resulting mixture was heated at 100° C. for 5 hours, whereupon it was partitioned between saturated aqueous sodium chloride solution (300 mL) and ethyl acetate (300 mL). The aqueous layer was extracted with ethyl acetate (3×200 mL), and the combined organic layers were washed with saturated aqueous sodium chloride solution (2×200 mL), dried, filtered, and concentrated in vacuo. Silica gel chromatography (Eluent: 5/1 petroleum ether/ ethyl acetate) afforded methyl 5-(difluoromethoxy)picolinate as a pale yellow oil (17 g, 65% yield). $^1$H NMR (400 MHz, CDCl$_3$) δ 8.56 (s, 1H), 8.17 (d, J=8.7 Hz, 1H), 7.59 (br d, J=8.7 Hz, 1H), 6.64 (t, $J_{HF}$=71.9 Hz, 1H), 4.00 (s, 3H).

Step 2: Synthesis of 5-(difluoromethoxy)picolinic acid (C9)

A solution of methyl 5-(difluoromethoxy)picolinate (C52) (17 g, 84 mmol) in tetrahydrofuran (100 mL) and water (50 mL) was cooled to 0° C. and treated with lithium hydroxide (6.0 g, 250 mmol). After the reaction mixture had stirred at room temperature for 2 hours, it was acidified to a pH of 3 with 1M aqueous hydrochloric acid. The aqueous layer was extracted with ethyl acetate (3×100 mL), and the combined organic layers were washed with saturated aqueous sodium chloride solution (100 mL), dried, filtered, and concentrated under reduced pressure to provide 5-(difluoromethoxy) picolinic acid as a white solid (13 g, 82% yield). LCMS m/z 189.8 [M+H]$^+$. $^1$H NMR (400 MHz, CDCl$_3$) δ 8.52 (d, J=2.4 Hz, 1H), 8.29 (d, J=8.5 Hz, 1H), 7.73 (dd, J=8.6, 2.4 Hz, 1H), 6.68 (t, $J_{HF}$=71.5 Hz, 1H).

Preparation P5: 3-chloro-5-(difluoromethoxy)picolinic acid (C11)

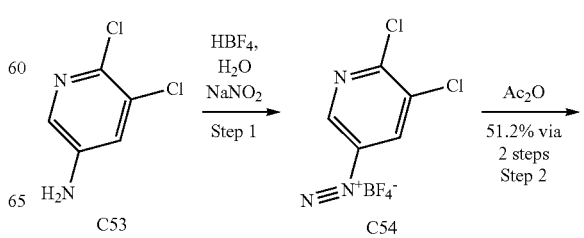

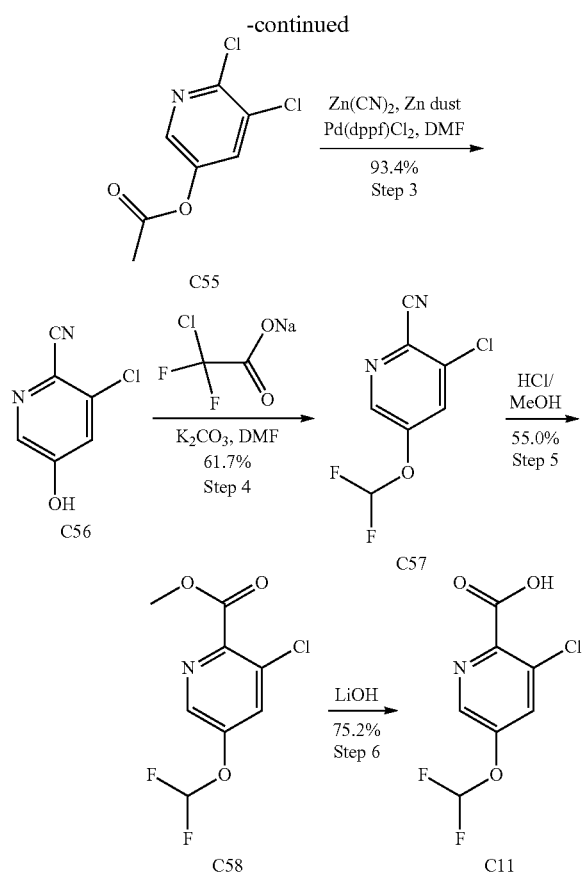

Step 1: Synthesis of 5,6-dichloropyridine-3-diazonium tetrafluoroborate (C54)

To a solution of 5,6-dichloropyridin-3-amine (C53) (15 g, 92.02 mmol) in tetrafluoroboric acid (~45% in water, 150 mL) was added a solution of sodium nitrite (6.67 g, 96.6 mmol) in water (90 mL) dropwise at 0° C., during which time the diazonium salt precipitated. After the addition, the mixture was stirred at 0° C. for 1 hour. The mixture was filtered and the filter cake was washed with petroleum ether (200 mL×3) and dried under vacuum at room temperature for 15 hours to afford crude 5,6-dichloropyridine-3-diazonium tetrafluoroborate (25.8 g) as a pale red solid that was used in the next step without purification.

Step 2: Synthesis of 5,6-dichloropyridin-3-yl acetate (C55)

Crude 5,6-dichloropyridine-3-diazonium tetrafluoroborate (C54) (25.8 g, 92.02 mmol) was dissolved in acetic anhydride (75 mL) and slowly warmed to 70° C. When the evolution of $N_2$ had ceased, stirring was continued for 1 hour at 70° C. and then the solvent was evaporated. The residue was dissolved in tert-butyl methyl ether (100 mL) and washed with water (40 mL×4). The combined aqueous layers were extracted with additional tert-butyl methyl ether (50 mL×3). The combined organic layers were washed with brine solution (20 mL×5), dried over anhydrous sodium sulfate, filtered and concentrated. The residue was purified by flash column chromatography (40 g silica gel, 0 to 25% ethyl acetate in petroleum ether) to afford 5,6-dichloropyridin-3-yl acetate (9.7 g, 51.2% yield—2 steps) as yellow oil. $^1$H NMR (400 MHz, DMSO-$d_6$) δ 8.33 (d, J=2.5 Hz, 1H), 8.18 (d, J=2.5 Hz, 1H), 2.32 (s, 3H).

Step 3: Synthesis of 3-chloro-5-hydroxypicolinonitrile (C56)

To a solution of 5,6-dichloropyridin-3-yl acetate (C55) (9.7 g, 47.1 mmol) in DMF (60 mL) was added zinc cyanide (2.6 g, 22.1 mmol), zinc dust (145 mg, 2.21 mmol) and [1,1'-Bis(diphenylphosphino)ferrocene]dichloropalladium (II) (1.72 g, 2.35 mmol) at room temperature. The resulting mixture was stirred at 140° C. for 13 hours under nitrogen. TLC (petroleum ether:ethyl acetate=3:1) showed the reaction was complete. The mixture was diluted with tert-butyl methyl ether (200 mL) and water (150 mL) and filtered through a Celite pad. The filtrate was separated and the aqueous layer was extracted with additional tert-butyl methyl ether (50 mL×3). The combined organic layers were washed with brine solution (50 mL×8), dried over anhydrous sodium sulfate, filtered and concentrated to afford 3-chloro-5-hydroxypicolinonitrile (6.8 g, 93.4% yield) as a brown solid. $^1$H NMR (400 MHz, $CD_3OD$) δ 8.16 (d, J=2.5 Hz, 1H), 7.38 (d, J=2.5 Hz, 1H).

Step 4: Synthesis of 3-chloro-5-(difluoromethoxy)picolinonitrile (C57)

A mixture of 3-chloro-5-hydroxypicolinonitrile (C56) (6.8 g, 44 mmol), sodium chloro(difluoro)acetate (20 g, 176 mmol) and potassium carbonate (36.5 g, 264 mmol) in DMF (70 mL) was stirred at 100° C. for 40 minutes (until no gas evolution can be seen). TLC (petroleum ether:ethyl acetate=3:1) showed the reaction was complete. The mixture was diluted with tert-butyl methyl ether (200 mL) and water (150 mL) and separated. The aqueous layer was extracted with additional tert-butyl methyl ether (100 mL×3). The combined organic layers were washed with brine solution (50 mL×8), dried over anhydrous sodium sulfate, filtered and concentrated to afford a brown oil (7.2 g) that was purified by flash column chromatography (40 g silica gel, 0% to 20% ethyl acetate in petroleum ether) to afford 3-chloro-5-(difluoromethoxy)picolinonitrile (5.55 g, 61.7% yield) as a yellow oil. $^1$H NMR (400 MHz, $CDCl_3$) δ 8.44-8.53 (m, 1H), 7.64-7.74 (m, 1H), 6.68 (t, $J_{HF}$=70.8 Hz, 1H).

Step 5: Synthesis of methyl 3-chloro-5-(difluoromethoxy)picolinate (C58)

A solution of 3-chloro-5-(difluoromethoxy)picolinonitrile (C57) (4.82 g, 23.6 mmol) in 4 N HCl/MeOH (75 mL) was stirred at 60° C. for 13 hours. TLC (petroleum ether:ethyl acetate=3:1) showed most of the starting material was consumed. The mixture was diluted with water (50 mL) and stirred at room temperature for 30 minutes. The mixture was concentrated and the residual aqueous phase was neutralized by saturated aqueous sodium bicarbonate (200 mL) and extracted with ethyl acetate (60 mL×3). The combined organic layers were washed with brine solution (30 mL), dried over anhydrous sodium sulfate, filtered and concentrated to give crude product (5.28 g) as brown oil, which was combined with previous batch from smaller scale (528 mg) and was purified together by flash column chromatography (40 g silica gel, 0% to 20% ethyl acetate in petroleum ether) to afford methyl 3-chloro-5-(difluoromethoxy)picolinate (3.4 g, 55.0% yield) as yellow oil, which solidified while left standing at room temperature. ¹H NMR (400 MHz, CDCl₃) δ 8.41-8.50 (m, 1H), 7.65 (d, J=1.5 Hz, 1H), 6.64 (t, $J_{HF}$=71.3 Hz, 1H), 4.02 (s, 3H).

Step 6: Synthesis of
3-chloro-5-(difluoromethoxy)picolinic acid (C11)

To a solution of methyl 3-chloro-5-(difluoromethoxy)picolinate (C58) (1 g, 4.21 mmol) in tetrahydrofuran (40 mL) and water (20 mL) was added lithium hydroxide monohydrate (279 mg, 6.31 mmol) at room temperature. The reaction mixture was stirred at room temperature for 3 hours, concentrated and the residual aqueous phase was adjusted to pH 2-3 with 2 N aqueous hydrochloric acid and extracted with ethyl acetate (20 mL×7). The organic layers were dried over anhydrous sodium sulfate, filtered and concentrated to afford 3-chloro-5-(difluoromethoxy)picolinic acid (720 mg, 75.2% yield) as a pale yellow solid. LCMS m/z 222.0 [M−H]⁻ with chlorine isotope pattern observed. ¹H NMR (400 MHz, DMSO-d₆) δ 8.51 (d, J=2.0 Hz, 1H), 8.06 (d, J=2.0 Hz, 1H), 7.44 (t, $J_{HF}$=72.8 Hz, 1H).

Preparation P6: 5,5-dimethyl-3,3a,4,5-tetrahydro-7H-pyrano[3,4-c]isoxazole (#C906)

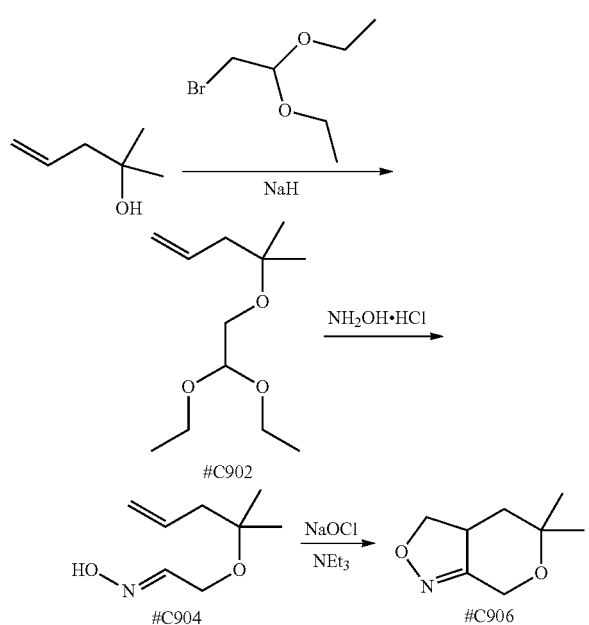

Step 1: Synthesis of
4-(2,2-diethoxyethoxy)-4-methylpent-1-ene (#C902)

2-Methylpent-4-en-2-ol (89 g, 0.89 mmol) was added dropwise to a suspension of sodium hydride (60% in mineral oil; 107 g, 2.67 mol) in tetrahydrofuran (1.5 L). The reaction mixture was stirred for 45 minutes at room temperature, whereupon 2-bromo-1,1-diethoxyethane (90%, 292 g, 1.33 mol) was slowly added. After the reaction mixture had been heated at reflux for 36 hours, it was poured into ice-water (2 L) and extracted with ethyl acetate (3×1 L). The combined organic layers were washed with saturated aqueous sodium chloride solution (2×1.5 L), dried over sodium sulfate, filtered, and concentrated in vacuo. Purification via chromatography on alumina (Eluent: petroleum ether) afforded the product as a yellow oil. By ¹H NMR, this material contained a significant percentage of 2-bromo-1,1-diethoxyethane; half of this material was taken directly to the following step. ¹H NMR (400 MHz, CDCl₃), characteristic product peaks: δ 5.92-5.78 (m, 1H), 5.06 (s, 1H), 5.05-5.01 (m, 1H), 4.68 (t, J=5.5 Hz, 1H), 3.43 (d, J=5.3 Hz, 2H), 2.24 (br d, J=7.3 Hz, 2H).

Step 2: Synthesis of N-hydroxy-2-[(2-methylpent-4-en-2-yl)oxy]ethanimine (#C904)

To a solution of #C902 (from the previous step; 85.0 g, ≤445 mmol) in ethanol (1.4 L) and water (700 mL) was added hydroxylamine hydrochloride (81.9 g, 1.18 mol) at room temperature (~12° C.). The reaction mixture was stirred at 50° C. for 15 hours, whereupon it was extracted with dichloromethane (2×100 mL). The combined organic layers were washed with saturated aqueous sodium chloride solution (2×1 L), dried over sodium sulfate, filtered, and concentrated in vacuo. Silica gel chromatography (Gradient: 0% to 10% ethyl acetate in petroleum ether) provided the product as a colorless oil. By ¹H NMR, this product was somewhat impure, and consisted of a mixture of geometric isomers around the oxime. Yield: 40.0 g, 254 mmol, 57% over 2 steps. ¹H NMR (400 MHz, CDCl₃), product peaks only: δ [7.47 (t, J=5.4 Hz) and 6.88 (t, J=3.4 Hz), total 1H], 5.90-5.76 (m, 1H), 5.09 (br s, 1H), 5.08-5.03 (m, 1H), [4.31 (d, J=3.6 Hz) and 4.05 (d, J=5.5 Hz), total 2H], 2.27 (d, J=7.2 Hz, 2H), 1.19 (s, 6H).

Step 3: Synthesis of 5,5-dimethyl-3,3a,4,5-tetrahydro-7H-pyrano[3,4-c][1,2]oxazole (#C906)

Triethylamine (1.93 g, 19.1 mmol) was added to a solution of #C904 (40.0 g, 254 mmol) in dichloromethane (1.2 L) at room temperature (~15° C.). Aqueous sodium hypochlorite solution (5%, 1.2 L) was then slowly added via syringe while the internal reaction temperature was maintained between 22° C. and 25° C. After completion of the addition, the reaction mixture was separated; the organic layer was washed with saturated aqueous sodium chloride solution (2×500 mL), dried over sodium sulfate, filtered, and concentrated in vacuo. Silica gel chromatography (Gradient: 0% to 10% ethyl acetate in petroleum ether) afforded the product as a colorless oil. Yield: 18 g, 120 mmol, 47%. LCMS m/z 155.7 [M+H]⁺. ¹H NMR (400 MHz, CDCl₃) δ 4.59 (dd, J=9.9, 7.9 Hz, 1H), 4.52 (d, half of AB quartet, J=14.0 Hz, 1H), 4.36 (br dd, half of ABX pattern, J=14.0, 0.8 Hz, 1H), 3.75 (dd, J=11.6, 7.8 Hz, 1H), 3.62-3.50 (m, 1H), 2.05 (dd, J=13.0, 6.3 Hz, 1H), 1.61 (dd, J=12, 12 Hz, 1H), 1.33 (s, 3H), 1.28 (s, 3H).

Preparation P7: tert-butyl (2-((3R,4R)-3-amino-4-(hydroxymethyl)-6,6-dimethyl tetrahydro-2H-pyran-3-yl)thiazol-4-yl)carbamate (#C928)

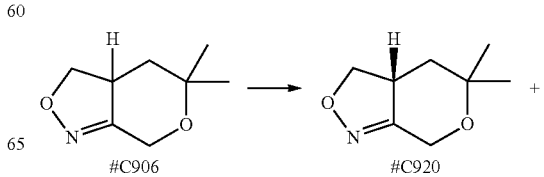

-continued

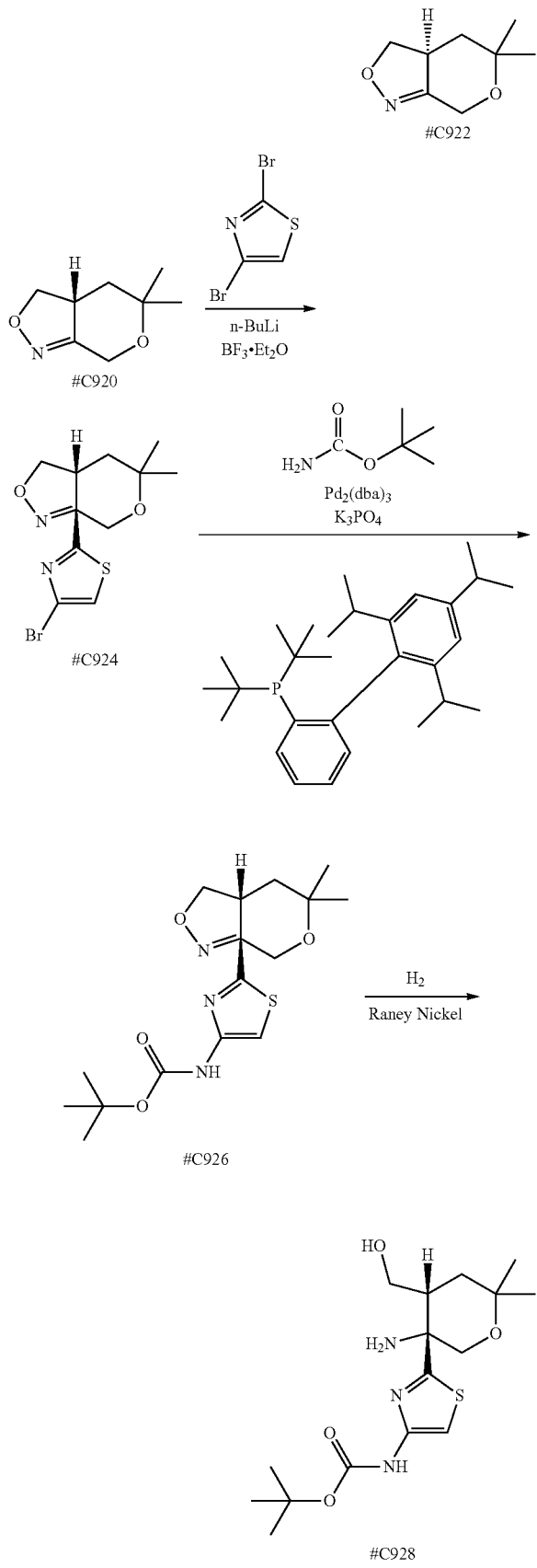

Step 1: Synthesis of (3aR)-5,5-dimethyl-3,3a,4,5-tetrahydro-7H-pyrano[3,4-c][1,2]oxazole (#C920) and (3aS)-5,5-dimethyl-3,3a,4,5-tetrahydro-7H-pyrano[3,4-c][1,2]oxazole (#C922)

Separation of #C906 (710 g) into its component enantiomers was carried out via supercritical fluid chromatography (Column: Chiral Technologies Chiralpak IC, 10 μm; Mobile phase: 7:3 carbon dioxide/2-propanol). Compound #C920 was the first-eluting enantiomer from the column, isolated as a brown solid. Yield: 270 g, 38% for the isolation. Compound #C922 was the second-eluting enantiomer from the column, also isolated as a brown solid. Yield: 270 g, 38% for the isolation.

The indicated absolute stereochemistry for these two products was assigned on the following basis. Compound #C920 was used in the synthesis of two Examples herein, both of which exhibited substantial biological activity; this indicates that the absolute stereochemistry of #C920 matches that of related active compounds in the literature: See C. R. Butler et al., *J. Med. Chem.* 2015, 58, 2678-2702 and M. A. Brodney, *J. Med. Chem.* 2015, 58, 3223-3252. The same rationale was used to assign the absolute stereochemistry of Examples below that were separated into their component enantiomers in the final step.

C920: LCMS m/z 155.8 [M+H]$^+$. $^1$H NMR (400 MHz, CDCl$_3$) δ 4.59 (dd, J=9.9, 7.9 Hz, 1H), 4.51 (d, half of AB quartet, J=14.0 Hz, 1H), 4.36 (dd, half of ABX pattern, J=14.0, 1.2 Hz, 1H), 3.74 (dd, J=11.6, 7.8 Hz, 1H), 3.62-3.49 (m, 1H), 2.05 (dd, J=12.9, 6.3 Hz, 1H), 1.60 (dd, J=12.4, 12.3 Hz, 1H), 1.33 (s, 3H), 1.28 (s, 3H).

C922: LCMS m/z 155.8 [M+H]$^+$. $^1$H NMR (400 MHz, CDCl$_3$) δ 4.60 (dd, J=10.0, 7.8 Hz, 1H), 4.52 (d, half of AB quartet, J=14.0 Hz, 1H), 4.36 (dd, half of AB quartet, J=14.0, 1.4 Hz, 1H), 3.75 (dd, J=11.6, 7.8 Hz, 1H), 3.63-3.49 (m, 1H), 2.06 (dd, J=12.8, 6.3 Hz, 1H), 1.61 (dd, J=12.3, 12.3 Hz, 1H), 1.34 (s, 3H), 1.28 (s, 3H).

Step 2: Synthesis of (3aR,7aR)-7a-(4-bromo-1,3-thiazol-2-yl)-5,5-dimethylhexahydro-1H-pyrano[3,4-c][1,2]oxazole (#C924)

Boron trifluoride diethyl etherate (3.00 mL, 23.7 mmol) was added to a −65° C. slurry of 2,4-dibromo-1,3-thiazole (5.63 g, 23.2 mmol) in toluene (50 mL). n-Butyllithium (2.5 M solution in hexanes; 10 mL, 25 mmol) was then slowly added, and the reaction mixture was allowed to stir at −65° C. for 10 minutes. A solution of #C920 (3.0 g, 19 mmol) in tetrahydrofuran (5 mL) was added drop-wise, and stirring was continued for 30 minutes at −65° C., whereupon the reaction was quenched via addition of saturated aqueous ammonium chloride solution (150 mL) and the temperature warmed to −10° C. to 0° C. The aqueous layer was extracted with ethyl acetate (2×100 mL), and the combined organic layers were washed with saturated aqueous sodium chloride solution (2×100 mL), dried over sodium sulfate, filtered, and concentrated in vacuo. Silica gel chromatography (Gradient: 0% to 10% ethyl acetate in petroleum ether) afforded the product as a yellow solid. Yield: 4.3 g, 13 mmol, 68%. $^1$H NMR (400 MHz, CDCl$_3$) δ 7.21 (s, 1H), 6.42 (s, 1H), 4.09 (d, J=13.0 Hz, 1H), 3.79-3.68 (m, 3H), 3.47-3.36 (m, 1H), 1.76 (dd, J=14.0, 6.6 Hz, 1H), 1.57 (br dd, J=13, 13 Hz, 1H), 1.42 (s, 3H), 1.30 (s, 3H).

Step 3: Synthesis of tert-butyl {2-[(3aR,7aR)-5,5-dimethyltetrahydro-1H-pyrano[3,4-c][1,2]oxazol-7a(7H)-yl]-1,3-thiazol-4-yl}carbamate (#C926)

A mixture of #C924 (4.30 g, 13.5 mmol), tert-butyl carbamate (2.37 g, 20.2 mmol), potassium phosphate (10 g, 47 mmol), tris(dibenzylideneacetone)dipalladium(0) (2.47 g, 2.70 mmol), and di-tert-butyl[2',4',6'-tri(propan-2-yl)biphenyl-2-yl]phosphane (572 mg, 1.35 mmol) in toluene (100 mL) was stirred at 115° C. for 18 hours. After the reaction mixture had cooled to room temperature, it was filtered through diatomaceous earth; the filter pad was washed with ethyl acetate (200 mL), and the combined filtrates were concentrated under reduced pressure. Chromatography on silica gel (Gradient: 0% to 25% ethyl acetate in petroleum ether) provided the product as a yellow foam. Yield: 2.95 g, 8.30 mmol, 61%. $^1$H NMR (400 MHz, CDCl$_3$), characteristic peaks: δ 7.24 (br s, 1H), 7.15 (br s, 1H), 6.36 (s, 1H), 4.03 (d, J=13.0 Hz, 1H), 3.79-3.69 (s, 3H), 3.33-3.23 (m, 1H), 1.72 (dd, half of ABX pattern, J=13.9, 6.5 Hz, 1H), 1.52 (s, 9H), 1.38 (s, 3H), 1.30 (s, 3H).

Step 4: Synthesis of tert-butyl {2-[(3R,4R)-3-amino-4-(hydroxymethyl)-6,6-dimethyltetrahydro-2H-pyran-3-yl]-1,3-thiazol-4-yl}carbamate (#C928)

Raney nickel (1.94 g, 33.0 mmol) was added to a solution of #C926 (4.70 g, 13.2 mmol) in 2-propanol (30 mL) and tetrahydrofuran (30 mL). The resulting mixture was subjected to three cycles of degassing and being charged with hydrogen, and then stirred at 50° C. under a hydrogen balloon for 4 hours. After the reaction mixture had cooled to room temperature, it was combined with a similar reaction mixture carried out using #C926 (2.0 g, 5.6 mmol) and filtered through a pad of diatomaceous earth. The filter cake was washed with ethyl acetate (200 mL), and the combined filtrates were concentrated in vacuo to provide the product as a yellow gum. Yield: 6.8 g, 19 mmol, quantitative. LCMS m/z 358.1 [M+H]$^+$.

Preparation P8

N-((4aR,8aR)-8a-(4-aminothiazol-2-yl)-6,6-dimethyl-4,4a,5,6,8,8a-hexahydropyrano[3,4-d][1,3]oxazin-2-yl)benzamide (C931)

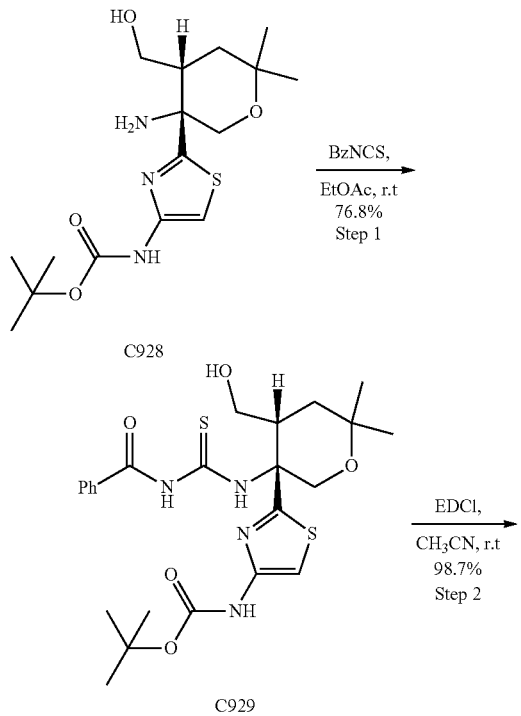

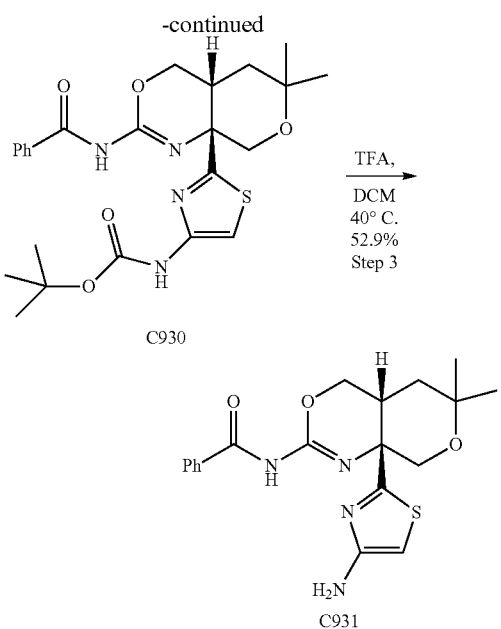

Step 1: Synthesis of tert-butyl (2-((3R,4R)-3-(3-benzoylthioureido)-4-(hydroxymethyl)-6,6-dimethyltetrahydro-2H-pyran-3-yl)thiazol-4-yl)carbamate (C929)

To a solution of tert-butyl (2-((3R,4R)-3-amino-4-(hydroxymethyl)-6,6-dimethyltetrahydro-2H-pyran-3-yl)thiazol-4-yl)carbamate (C928) (2.95 g, 8.25 mmol, 1 eq) in tetrahydrofuran (50 mL) was added benzoyl isothiocyanate (1.41 g, 8.67 mmol, 1.05 eq) in one portion at room temperature. The reaction mixture was stirred for 3 hours at room temperature. TLC analysis (petroleum ether:ethyl acetate=2:1, Rf~0.45, UV) indicated the starting material was consumed completely and a main less polar spot. The reaction mixture was concentrated in vacuo to afford to a dark yellow oil (6.7 g) then purified by flash column chromatography (80 g silica gel, 0% to 30% ethyl acetate in petroleum ether) to afford tert-butyl (2-((3R,4R)-3-(3-benzoylthioureido)-4-(hydroxymethyl)-6,6-dimethyltetrahydro-2H-pyran-3-yl)thiazol-4-yl)carbamate (3.3 g, yield: 76.8%) as a yellow solid. LCMS 543.1 [M+Na]$^+$ $^1$H NMR (400 MHz, CDCl$_3$) δ 11.72 (s, 1H), 8.96 (s, 1H), 7.86 (d, J=7.5 Hz, 2H), 7.60-7.66 (m, 1H), 7.46-7.56 (m, 3H), 7.24 (br. s., 1H), 4.99 (d, J=12.0 Hz, 1H), 3.96 (d, J=12.6 Hz, 1H), 3.77-3.89 (m, 2H), 2.83 (br. s., 1H), 2.52 (qd, J=4.4, 13.0 Hz, 1H), 1.94 (t, J=13.8 Hz, 1H), 1.65 (dd, J=4.0, 14.0 Hz, 1H), 1.51 (s, 9H), 1.36 (s, 3H), 1.35 (s, 3H).

Step 2: Synthesis of tert-butyl (2-((4aR,8aR)-2-benzamido-6,6-dimethyl-4,4a,5,6-tetrahydropyrano[3,4-d][1,3]oxazin-8a(8H)-yl)thiazol-4-yl)carbamate (C930)

EDCl (1.2 g, 6.25 mmol, 1.2 eq) was added in one portion at room temperature to a mixture of tert-butyl (2-((3R,4R)-3-(3-benzoylthioureido)-4-(hydroxymethyl)-6,6-dimethyl-tetrahydro-2H-pyran-3-yl)thiazol-4-yl)carbamate (C929) (2.71 g, 5.20 mmol, 1 eq) in acetonitrile (30 mL). The suspension stirred at room temperature for 15 hours, concentrated, then diluted with ethyl acetate (100 mL) and water (50 mL). The phases were separated and the aqueous layer was extracted with additional ethyl acetate (50 mL). The combined organic layers were washed with 0.1 N aqueous hydrochloric acid (50 mL). The aqueous phase was extracted with additional ethyl acetate (50 mL) and the combined organic phases were washed with saturated aqueous sodium bicarbonate (50 mL). The aqueous layer (pH 8-9) was extracted with additional ethyl acetate (50 mL). The combined organic layers were washed with brine solution (80 mL), dried over anhydrous sodium sulfate, filtered and concentrated to afford tert-butyl (2-((4aR,8aR)-2-benzamido-6,6-dimethyl-4,4a,5,6-tetrahydropyrano[3,4-d][1,3]oxazin-8a(8H)-yl)thiazol-4-yl)carbamate (2.5 g, yield: 98.7%) as a pale yellow foam that was carried on to the next step without further purification. LCMS m/z 487.2 [M+H]⁺

Step 3: Synthesis of N-((4aR,8aR)-8a-(4-aminothiazol-2-yl)-6,6-dimethyl-4,4a,5,6,8,8a-hexahydropyrano[3,4-d][1,3]oxazin-2-yl)benzamide (C931)

To a yellow solution of tert-butyl (2-((4aR,8aR)-2-benzamido-6,6-dimethyl-4,4a,5,6-tetrahydropyrano[3,4-d][1,3]oxazin-8a(8H)-yl)thiazol-4-yl)carbamate (C930) (2.5 g, 5.14 mmol, 1 eq) in dichloromethane (5 mL) was added trifluoroacetic acid (5 mL) at room temperature. The yellow solution was stirred at 40° C. for 30 minutes. The mixture was diluted with dichloromethane (100 mL) and poured into saturated aqueous sodium bicarbonate (80 mL) at room temperature. The mixture was stirred for 5 minutes, and then separated. The aqueous phase (pH 7-8) was extracted with dichloromethane (50 mL×3). The combined organic layers were washed with brine solution (50 mL), dried over anhydrous sodium sulfate, filtered and concentrated to obtain a yellow foam (1.92 g). This was dissolved in dichloromethane (30 mL) and ethyl acetate (30 mL), concentrated to ~20 mL volume and the resulting suspension was left standing at room temperature for 1 hour and filtered. The filtrate was concentrated to ~10 mL volume. The resulting suspension was left standing at room temperature for 30 minutes and filtered. The pale yellow filter cakes were combined to afford N-((4aR,8aR)-8a-(4-aminothiazol-2-yl)-6,6-dimethyl-4,4a,5,6,8,8a-hexahydropyrano[3,4-d][1,3]oxazin-2-yl)benzamide (1.05 g, yield: 52.9%, 87.63% purity determined by LCMS m/z 387.1 [M+H]⁺)

Example 8

N-(2-((4aR,8aR)-2-Amino-6,6-dimethyl-4,4a,5,6-tetrahydropyrano[3,4-d][1,3]oxazin-8a(8H)-yl)thiazol-4-yl)-5-(difluoromethoxy)picolinamide (8) from Chiral N-((4aR,8aR)-8a-(4-aminothiazol-2-yl)-6,6-dimethyl-4,4a,5,6,8,8a-hexahydropyrano[3,4-d][1,3]oxazin-2-yl)benzamide (C931)

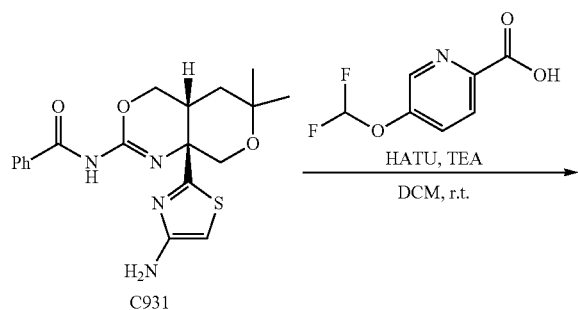

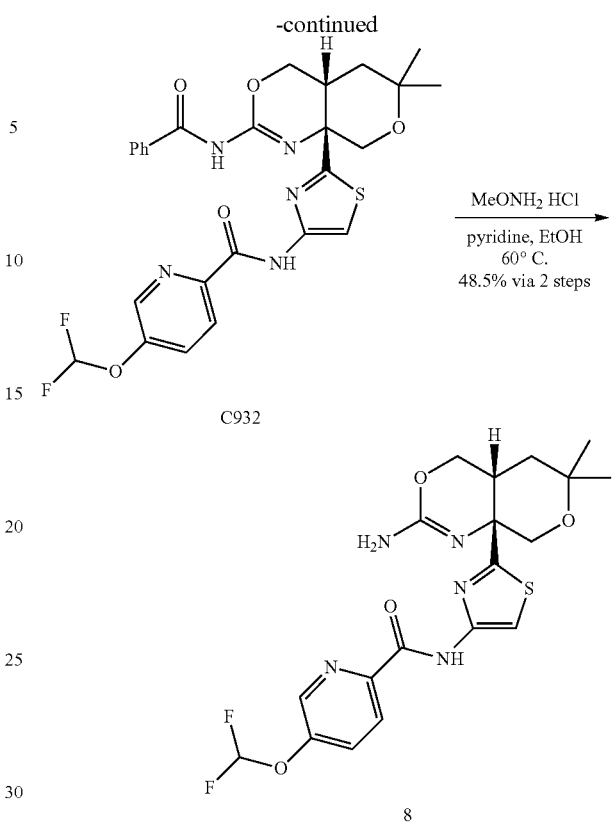

To a solution of 5-(difluoromethoxy) picolinic acid (92 mg, 0.486 mmol, 1.43 eq) in dichloromethane (20 mL) was added HATU (188 mg, 0.493 mmol, 1.45 eq) and triethylamine (60 mg, 0.593 mmol, 1.743 eq) at room temperature and stirred for 1 hour. N-((4aR,8aR)-8a-(4-aminothiazol-2-yl)-6,6-dimethyl-4,4a,5,6,8,8a-hexahydropyrano[3,4-d][1,3]oxazin-2-yl)benzamide (C931) (150 mg, 0.34 mmol, 1 eq) was added in one portion then stirred at room temperature for 2 hours. The reaction mixture was diluted with dichloromethane (50 mL) and washed with brine solution. The organic extract was concentrated to afford N-(2-((4aR,8aR)-2-benzamido-6,6-dimethyl-4,4a,5,6-tetrahydropyrano[3,4-d][1,3]oxazin-8a(8H)-yl)thiazol-4-yl)-5-(difluoromethoxy) picolinamide (C932) (360 mg, 0.34 mmol, LCMS m/z 580.1 [M+Na]⁺) as an orange solid, which was carried into the benzoyl deprotection reaction by suspending in ethanol (20 mL), adding methoxylamine hydrochloride (284 mg, 3.4 mmol) and pyridine (2.69 g, 34 mmol) at room temperature, then stirring the resulting solution at 60° C. for 12 hours. This mixture was combined with another benzoyl deprotection reaction (⅛ᵗʰ the scale, 0.045 mmol) and concentrated to afford the crude product (680 mg) which was purified by achiral preparative HPLC (Column: Phenomenex Gemini C18 250 mm×21.2 mm, 5 μm; Mobile phase: from 34% acetonitrile in water containing 0.05% ammonia to 54% acetonitrile in water containing 0.05% ammonia over 10 minutes, hold at 54% acetonitrile in water containing 0.05% ammonia for 2 minutes; flow rate: 30 mL/min). Lyophilization afforded pure N-(2-((4aR,8aR)-2-amino-6,6-dimethyl-4,4a,5,6-tetrahydropyrano[3,4-d][1,3]oxazin-8a(8H)-yl)thiazol-4-yl)-5-(difluoromethoxy) picolinamide (85 mg, Yield: 48.5% overall for the two steps and combined reactions) as a white solid. LCMS m/z 453.9 [M+H]⁺ ¹H NMR (400 MHz, CDCl₃) δ 10.40 (s, 1H), 8.49 (d, J=2.5 Hz, 1H), 8.32

(d, J=8.5 Hz, 1H), 7.72 (s, 1H), 7.68 (dd, J=2.5, 8.5 Hz, 1H), 6.65 (t, $J_{HF}$=72.0 Hz, 1H), 4.18 (br. s., 2H), 4.08 (d, J=11.5 Hz, 1H), 4.00-4.06 (m, 1H), 3.79 (d, J=11.0 Hz, 1H), 3.65 (d, J=11.5 Hz, 1H), 2.76-2.84 (m, 1H), 1.77 (t, J=13.6 Hz, 1H), 1.50 (dd, J=4.8, 13.3 Hz, 1H), 1.44 (s, 3H), 1.34 (s, 3H).

Example 9

N-(2-((4aR,8aR)-2-amino-6,6-dimethyl-4,4a,5,6-tetrahydropyrano[3,4-d][1,3]oxazin-8a(8H)-yl)thiazol-4-yl)-5-(difluoromethoxy)-3-methylpicolinamide (9) from Chiral N-((4aR,8aR)-8a-(4-aminothiazol-2-yl)-6,6-dimethyl-4,4a,5,6,8,8a-hexahydro pyrano[3,4-d][1,3]oxazin-2-yl)benzamide (C931)

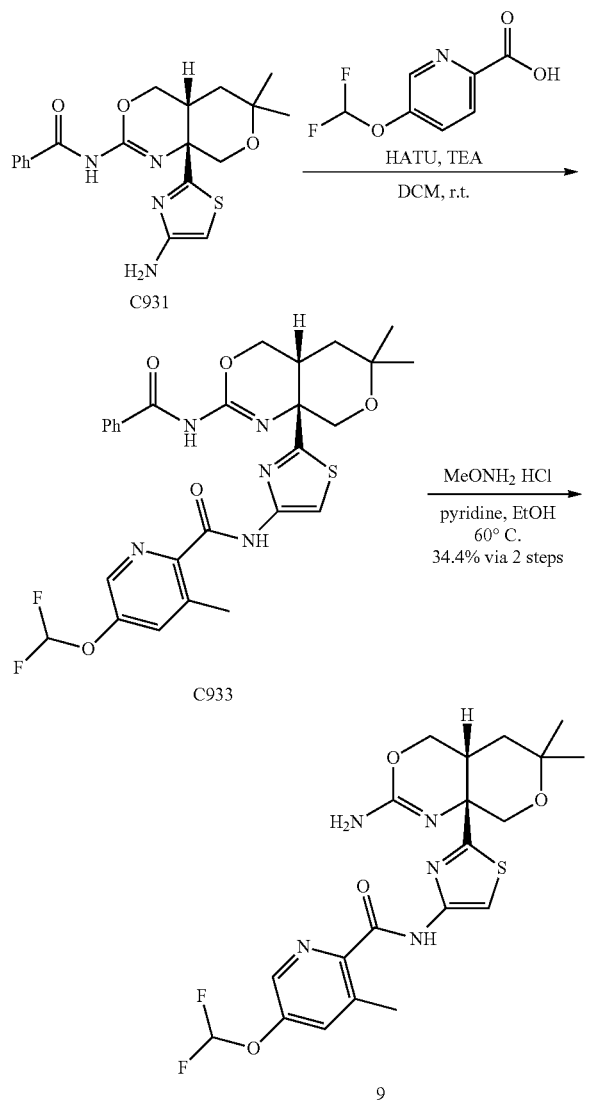

N-(2-((4aR,8aR)-2-Amino-6,6-dimethyl-4,4a,5,6-tetrahydropyrano[3,4-d][1,3]oxazin-8a(8H)-yl)thiazol-4-yl)-5-(difluoromethoxy)-3-methylpicolinamide (9) was synthesized in two steps according to the procedure for N-(2-((4aR,8aR)-2-amino-6,6-dimethyl-4,4a,5,6-tetrahydropyrano[3,4-d][1,3]oxazin-8a(8H)-yl)thiazol-4-yl)-5-(difluoromethoxy) picolinamide using N-((4aR,8aR)-8a-(4-aminothiazol-2-yl)-6,6-dimethyl-4,4a,5,6,8,8a-hexahydropyrano[3,4-d][1,3]oxazin-2-yl)benzamide (C931) (150 mg, 0.34 mmol, 1 eq), 5-(difluoromethoxy)-3-methylpicolinic acid (98 mg, 0.482 mmol), dichloromethane (20 mL), HATU (188 mg, 0.493 mmol, 1.45 eq), triethylamine (60 mg, 0.593 mmol, 1.743 eq) in the amide formation step and ethanol (20 mL), methoxylamine hydrochloride (284 mg, 3.4 mmol) and pyridine (2.69 g, 34 mmol) in the benzoyl deprotection step. This afforded crude N-(2-((4aR,8aR)-2-amino-6,6-dimethyl-4,4a,5,6-tetrahydropyrano[3,4-d][1,3]oxazin-8a(8H)-yl)thiazol-4-yl)-5-(difluoromethoxy)-3-methylpicolinamide (9) (658 mg from this sequence also combined with a similar reaction on ⅛$^{th}$ the scale, or 0.045 mmol additional) which was purified by achiral preparative HPLC (Column: Phenomenex Gemini C18 250 mm×21.2 mm, 5 μm Mobile phase: from 39% acetonitrile in water containing 0.05% ammonia to 59% acetonitrile in water containing 0.05% ammonia over 10 minutes, hold at 59% acetonitrile in water containing 0.05% ammonia for 2 minutes; flow rate: 30 mL/min). Lyophilization afforded pure N-(2-((4aR,8aR)-2-amino-6,6-dimethyl-4,4a,5,6-tetrahydropyrano[3,4-d][1,3]oxazin-8a(8H)-yl)thiazol-4-yl)-5-(difluoromethoxy)-3-methylpicolinamide (933) (62 mg, Yield: 34.4% overall for the two steps and combined reactions) as a white solid. LCMS m/z 468.0 [M+H]$^+$ $^1$H NMR (400 MHz, CDCl$_3$) δ 10.57 (s, 1H), 8.30-8.37 (m, 1H), 7.68 (s, 1H), 7.38-7.46 (m, 1H), 6.63 (t, $J_{HF}$=72.3 Hz, 1H), 4.18 (br. s., 2H), 4.08 (d, J=12.0 Hz, 1H), 4.00-4.06 (m, 1H), 3.78 (d, J=10.5 Hz, 1H), 3.64 (d, J=12.0 Hz, 1H), 2.84 (s, 3H), 2.76-2.83 (m, 1H), 1.72-1.82 (m, 1H), 1.49 (dd, J=4.5, 13.0 Hz, 1H), 1.44 (s, 3H), 1.34 (s, 3H).

Preparation P9

Racemic (+/−)-N-((4aR*,6R*,8aR*)-8a-(4-aminothiazol-2-yl)-6-(trifluoromethyl)-4,4a,5,6,8,8a-hexahydropyrano[3,4-d][1,3]oxazin-2-yl)benzamide (C65)

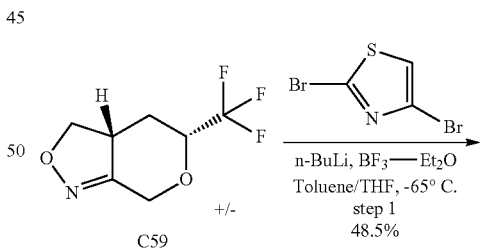

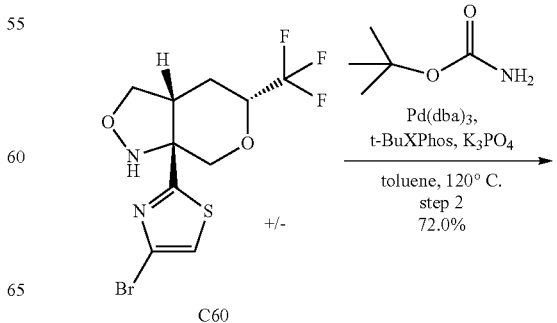

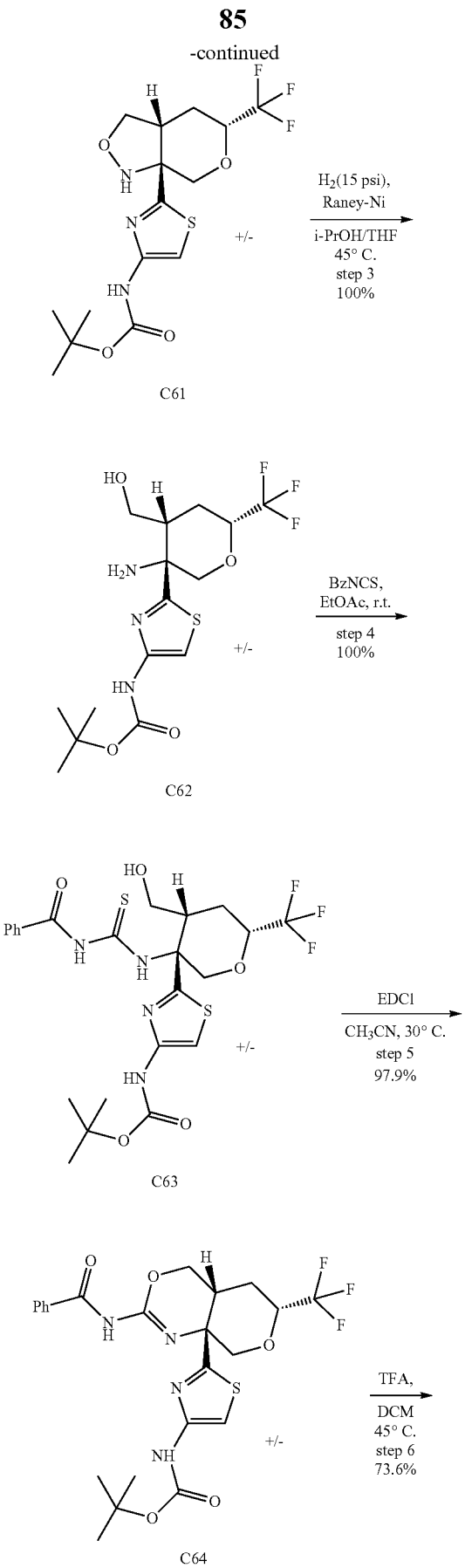

(+/−)-(3aR*,5R*)-5-(Trifluoromethyl)-3,3a,4,5-tetrahydro-7H-pyrano[3,4-c]isoxazole (C59) was prepared by methods known in the art (such as methods described in US2010/0093999 A1) starting from commercially available racemic 1,1,1-trifluoro-4-penten-2-ol.

Step 1: Synthesis of (+/−)-(3aR*,5R*,7aR*)-7a-(4-bromothiazol-2-yl)-5-(trifluoromethyl)hexahydro-1H-pyrano[3,4-c]isoxazole (C60)

To a thick slurry of 2,4-dibromothiazole (11 g, 45.3 mmol, 1.36 eq) in toluene (150 mL) was added $BF_3 \cdot Et_2O$ (6.78 g, 6 mL, 47.8 mmol, 1.435 eq) at −65° C., followed by slow addition of n-BuLi (20 mL, 2.5 M in hexane, 50 mmol, 1.5 eq). The resulting yellow solution was stirred for 25 minutes at this temperature, and then a solution of (+/−)-(3aR*,5R*)-5-(trifluoromethyl)-3,3a,4,5-tetrahydro-7H-pyrano[3,4-c]isoxazole (C59) (6.5 g, 33.3 mmol, 1 eq) in THF (20 mL) was added dropwise at −65° C. The brown solution was stirred for another 30 minutes at the same temperature. TLC (petroleum ether:ethyl acetate=5:1, Rf~0.65, UV and then stained by $KMnO_4$) showed most of the starting material was consumed. The mixture was quenched with saturated aqueous $NH_4Cl$ (200 mL) and the temperature warmed up to −10~0° C. The color of the mixture turned to purple and then to yellow. The mixture was diluted with ethyl acetate (150 mL), partitioned and separated. The aqueous layer was extracted with ethyl acetate (150 mL×2). The combined organic layers were washed with brine (150 mL), dried over anhydrous $Na_2SO_4$, filtered and concentrated to give a crude brown oil (16.1 g) that was purified by flash column chromatography (40 g silica gel, gradient: 0% to 20% ethyl acetate in petroleum ether) to afford (+/−)-(3aR*,5R*,7aR*)-7a-(4-bromothiazol-2-yl)-5-(trifluoromethyl)hexahydro-1H-pyrano[3,4-c]isoxazole (C60) (5.8 g, yellow solid, yield: 48.5%). $^1$H NMR (400 MHz, $CDCl_3$) δ 6.40 (s, 1H), 3.98-4.18 (m, 3H), 3.85 (δ, J=8.0 Hz, 1H), 3.78 (dd, J=5.0, 7.5 Hz, 1H), 3.46 (td, J=5.8, 11.5 Hz, 1H), 2.11 (ddd, J=2.0, 6.8, 13.8 Hz, 1H), 1.72-1.85 (m, 1H).

Step 2: Synthesis of (+/−)-tert-butyl (2-((3aR*,5R*,7aR*)-5-(trifluoromethyl)tetrahydro-1H-pyrano[3,4-c]isoxazol-7a(7H)-yl)thiazol-4-yl)carbamate (C61)

A mixture of racemic (+/−)-(3aR*,5R*,7aR*)-7a-(4-bromothiazol-2-yl)-5-(trifluoromethyl)hexahydro-1H-pyrano[3,4-c]isoxazole (C60) (5.8 g, 16.1 mmol, 1 eq), tert-butyl carbamate (2.84 g, 24.2 mmol, 1.5 eq), $K_3PO_4$ (12 g, 56.5 mmol, 3.5 eq), $Pd_2(dba)_3$ (2.96 g, 3.23 mmol, 0.2 eq) and t-BuXPhos (686 mg, 1.61 mmol, 0.1 eq) in toluene (120 mL) was stirred at 120° C. for 18 h under $N_2$. The mixture was cooled to room temperature and filtered through Celite. The pad was washed with ethyl acetate (200 mL). The filtrate was concentrated to give a crude product (12.5 g) as a brown solid, which was purified by flash column chromatography (80 g silica gel, gradient: 0% to 20% ethyl acetate in petroleum ether) to afford (+/−)-tert-butyl (2-((3aR*,5R*,7aR*)-5-(trifluoromethyl)tetrahydro-1H-pyrano[3,4-c]isoxazol-7a(7H)-yl)thiazol-4-yl)carbamate (C61) (4.6 g, yellow foam, yield: 72.0%). $^1$H NMR (400 MHz, CDCl$_3$) δ 7.22 (br. S., 2H NH Boc overlapping with NH isoxazoline), 4.10 (d, J=12.6 Hz, 1H), 3.94-4.02 (m, 2H), 3.82 (d, J=7.5 Hz, 1H), 3.76 (dd, J=4.8, 7.8 Hz, 1H), 3.23-3.34 (m, 1H), 2.05-2.12 (m, 1H), 1.72-1.85 (m, 1H), 1.53 (s, 9H). LCMS m/z 418.1 [M+Na]$^+$ Step 3: Synthesis of (+/−)-tert-butyl (2-((3R*,4R*,6R*)-3-amino-4-(hydroxymethyl)-6-(trifluoromethyl)tetrahydro-2H-pyran-3-yl)thiazol-4-yl)carbamate (C62)

To a solution of (+/−)-tert-butyl (2-((3aR*,5R*,7aR*)-5-(trifluoromethyl)tetrahydro-1H-pyrano[3,4-c]isoxazol-7a(7H)-yl)thiazol-4-yl)carbamate (C61) (4.60 g, 11.6 mmol, 1 eq) in isopropanol (30 mL) and THF (30 mL) was added Raney-Ni (2.39 g, 40.7 mmol, 3.5 eq) at room temperature (~16° C.) under argon. The resulting black mixture was degassed three times with hydrogen and stirred at 45° C. under a hydrogen balloon for 2 hours. TLC (petroleum ether:EtOAc=2:1, Rf~0.2, UV) indicated most of the starting material was consumed and a main new spot was shown. The mixture was cooled to room temperature and filtered through a Celite pad. The filtered cake was washed with THF (200 mL) and ethyl acetate (100 mL). The filtrate was concentrated to afford (+/−)-tert-butyl (2-((3R*,4R*,6R*)-3-amino-4-(hydroxymethyl)-6-(trifluoromethyl)tetrahydro-2H-pyran-3-yl)thiazol-4-yl)carbamate (C62) (4.7 g, yellow foam, yield: 100%) which was taken on to the next step without further purification. $^1$H NMR (400 MHz, CDCl$_3$) δ 7.29 (br. s., 1H), 7.20 (br. s., 1H), 3.93-4.03 (m, 1H), 3.75-3.80 (m, 1H), 3.72 (dd, J=3.0, 11.5 Hz, 1H), 3.63-3.69 (m, 1H), 3.51 (dd, J=3.3, 11.3 Hz, 1H), 2.07-2.58 (m, 4H), 1.91 (td, J=3.2, 13.7 Hz, 1H), 1.53 (s, 9H).

Step 4: Synthesis of (+/−)-tert-butyl (2-((3R*,4R*,6R*)-3-(3-benzoylthioureido)-4-(hydroxymethyl)-6-(trifluoromethyl)tetrahydro-2H-pyran-3-yl)thiazol-4-yl)carbamate (C63)

To a solution of crude (+/−)-tert-butyl (2-((3R*,4R*,6R*)-3-amino-4-(hydroxymethyl)-6-(trifluoromethyl)tetrahydro-2H-pyran-3-yl)thiazol-4-yl)carbamate (C62) (4.7 g, 11.6 mmol, 1 eq) in ethyl acetate (40 mL) was added benzoyl isothiocyanate (2 g, 12.2 mmol, 1.055 eq) in one portion at room temperature. The reaction mixture was stirred at room temperature for 16 hours after being determined complete by LC/MS. The reaction suspension was filtered. The filter cake was washed with ethyl acetate (100 mL). The filter cake was dried in vacuo to afford pure (+/−)-tert-butyl (2-((3R*,4R*,6R*)-3-(3-benzoylthioureido)-4-(hydroxymethyl)-6-(trifluoromethyl) tetrahydro-2H-pyran-3-yl)thiazol-4-yl)carbamate (C63) (3.1 g, white solid, yield: 47.7%). The filtrate was concentrated to afford additional product of lower purity (4.4 g, yellow solid; yield: 52.3%). $^1$H NMR (400 MHz, CDCl$_3$) δ 11.73 (s, 1H), 8.94 (s, 1H), 7.83-7.92 (m, 2H), 7.60-7.69 (m, 1H), 7.49-7.59 (m, 2H), 7.33 (br. s., 1H), 5.75 (d, 11.73 (s, 1H), 8.94 (s, 1H), 7.83-7.92 (m, 2H), 7.60-7.69 (m, 1H), 7.49-7.59 (m, 2H), 7.33 (br. s., 1H), 5.75 (d, J=12.0 Hz, 1H), 3.99-4.10 (m, 1H), 3.80-3.97 (m, 3H), 2.31-2.41 (m, 1H), 2.14-2.28 (m, 2H), 1.99-2.09 (m, 1H), 1.52 (s, 9H). LCMS m/z 583.1 [M+Na]$^+$. The analytical data is representative for the first cropping of material.

Step 5: Synthesis of (+/−)-tert-butyl (2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)carbamate (C64)

To a solution of pure (+/−)-tert-butyl (2-((3R*,4R*,6R*)-3-(3-benzoylthioureido)-4-(hydroxymethyl)-6-(trifluoromethyl)tetrahydro-2H-pyran-3-yl)thiazol-4-yl)carbamate (C63) (3.1 g, 5.53 mmol, 1 eq) in acetonitrile (50 mL) was added EDCl (1.27 g, 6.64 mmol, 1.2 eq) in one portion at room temperature. The suspension stirred at room temperature for 16 hours, then at 25-30° C. for 2 h, then at 30° C. for 16 h. The reaction solution was concentrated to give a white solid that was dissolved dichloromethane (200 mL) then washed with water (100 mL×2). The aqueous layer was washed with additional dichloromethane (100 mL), then the combined lower organic extracts were dried over anhydrous Na$_2$SO$_4$, filtered and concentrated to afford (+/−)-tert-butyl (2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)carbamate (C64) (2.85 g, white foam, yield: 97.9%). $^1$H NMR (400 MHz, CDCl$_3$) δ 12.11 (br. s., 1H), 8.25 (d, J=5.5 Hz, 2H), 7.49-7.56 (m, 1H), 7.41-7.48 (m, 2H), 7.23 (br. s., 1H), 4.27-4.34 (m, 1H), 4.08-4.23 (m, 2H), 3.98-4.08 (m, 2H), 2.82-2.92 (m, 1H), 1.95-2.08 (m, 2H), 1.53 (s, 9H). LCMS m/z 548.8 [M+Na]$^+$.

Step 6: Synthesis of (+/−)-N-((4aR*,6R*,8aR*)-8a-(4-aminothiazol-2-yl)-6-(trifluoromethyl)-4,4a,5,6,8,8a-hexahydropyrano[3,4-d][1,3]oxazin-2-yl)benzamide (C65)

To a yellow solution of (+/−)-tert-butyl (2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)carbamate (C64) (2.35 g, 4.46 mmol, 1 eq) in dichloromethane (10 mL) was added trifluoroacetic acid (6 mL) at room temperature. The yellow solution was stirred at 45° C. for 25 minutes and deemed complete by LCMS analysis. The reaction solution was combined with previous reaction solution on smaller scale (0.95 mmol same limiting reagent, 2 mL dichloromethane, 2 mL trifluoroacetic acid) and the resulting combined solution was diluted with dichloromethane (100 mL) and poured into saturated aqueous NaHCO$_3$ (100 mL) at room temperature. The aqueous phase was extracted with dichloromethane (40 mL×3). The combined organic layers were dried over anhydrous Na$_2$SO$_4$, filtered and concentrated to give a crude pale yellow solid (2.1 g) that was dissolved into dichloromethane:ethyl acetate (1:1 v:v, 50 mL), concentrated to until about 10 mL of solvent remained, left standing at room temperature for 20 minutes and then filtered to give a white solid (~1.4 g). The filtrate was concentrated to until ~5 mL of solvents remained and then left standing at room temperature overnight (~16 hours). More white solids were filtered and both crops of white solids were combined and dried in vacuo to afford (+/−)-N-((4aR*,6R*,8aR*)-8a-(4-aminothiazol-2-yl)-6-(trifluoromethyl)-4,4a,5,6,8,8a-hexahydropyrano[3,4-d][1,3]oxazin-2-yl)benzamide (C65) (1.7 g, white solid, average yield from both reactions: 73.6%). $^1$H NMR (400 MHz, CDCl$_3$) δ 12.06 (br. s., 1H), 8.25 (d, J=7.5 Hz, 2H), 7.49-7.56 (m, 1H), 7.40-7.48 (m, 2H), 5.99 (s, 1H), 4.35 (dd, J=2.8, 11.8 Hz, 1H), 4.16-4.23 (m, 1H), 3.99-4.16 (m, 5H), 2.95 (dd, J=7.5, 10.0 Hz, 1H), 1.94-2.08 (m, 2H). LCMS m/z 427.0 [M+H]+

Example 10

Chiral N-(2-((4aS,6S,8aS)-2-amino-6-(trifluoromethyl)-4,4a,5,6-tetrahydropyrano [3,4-d][1,3]oxazin-8a(8H)-yl)thiazol-4-yl)-5-chloropicolinamide (10b) and Chiral N-(2-((4aR,6R,8aR)-2-amino-6-(trifluoromethyl)-4,4a,5,6-tetrahydropyrano[3,4-d][1,3] oxazin-8a(8H)-yl)thiazol-4-yl)-5-chloropicolinamide (10a)

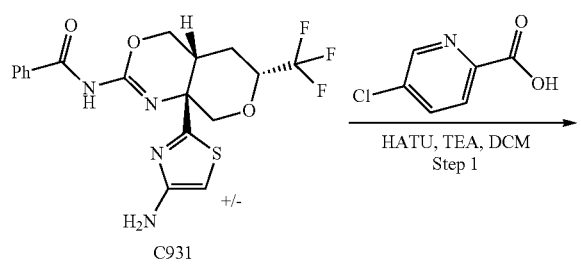

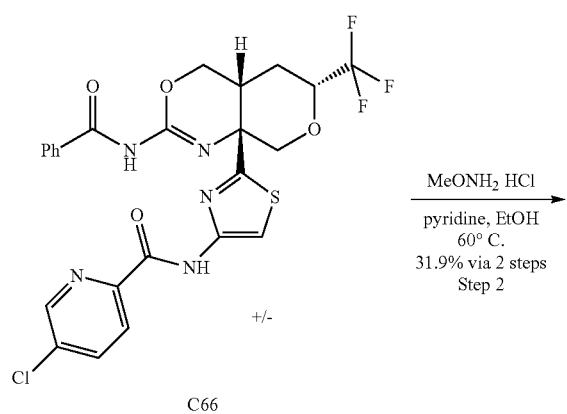

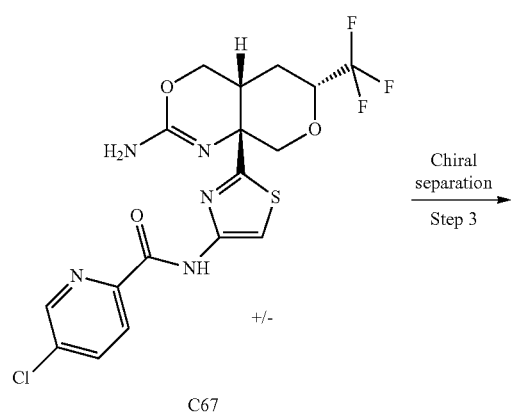

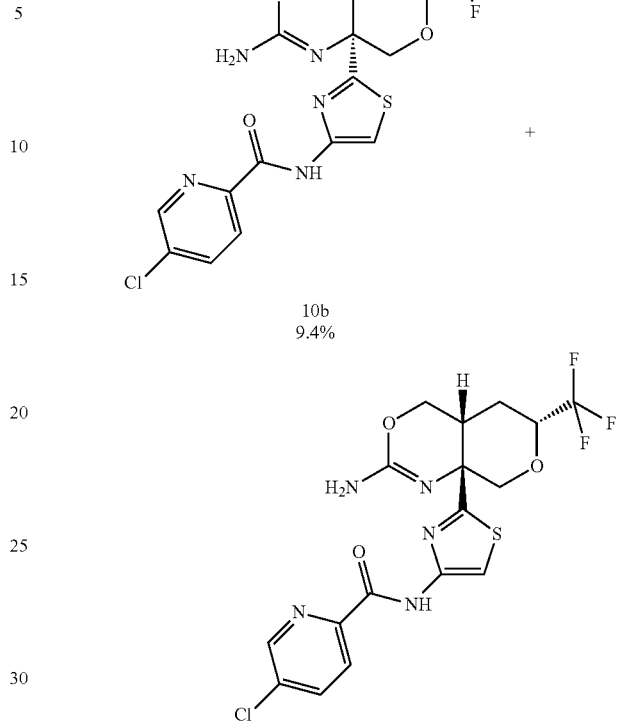

Step 1: Synthesis of (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-chloropicolinamide (C66)

To a stirring solution of commercially-available 5-chloropicolinic acid (96 mg, 0.609 mmol, 1.4 eq) in dichloromethane (20 mL) was added HATU (240 mg, 0.631 mmol, 1.45 eq) and triethylamine (75 mg, 0.741 mmol, 1.703 eq) at 15° C. After 30 minutes, (+/−)-N-((4aR*,6R*,8aR*)-8a-(4-aminothiazol-2-yl)-6-(trifluoromethyl)-4,4a,5,6,8,8a-hexahydropyrano[3,4-d][1,3]oxazin-2-yl)benzamide (C65) (200 mg, 0.435 mmol) was added in one portion. The resulting mixture was stirred at room temperature for 17 hours then diluted with dichloromethane (50 mL) and washed with brine solution (30 mL×2). The combined aqueous layers were washed with additional dichloromethane (25 mL). The combined organic layers were dried over anhydrous Na₂SO₄, filtered and concentrated to afford crude (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-chloropicolinamide (C66) (430 mg, 52.502% purity determined by LCMS m/z 566.1 [M+H]+ with chlorine isotope pattern observed) as an off-white solid, which was used directly for next step without further purification.

Step 2: Synthesis of (+/−)-N-(2-((4aR*,6R*,8aR*)-2-amino-6-(trifluoromethyl)-4,4a,5,6-tetrahydropyrano[3,4-d][1,3]oxazin-8a(8H)-yl)thiazol-4-yl)-5-chloropicolinamide (C67)

To a suspension of crude (+/−)-N-(2-((4aR*,6R*,8aR*)-2-benzamido-6-(trifluoromethyl)-4,4a,5,6-tetrahydropyrano

[3,4-d][1,3]oxazin-8a(8H)-yl)thiazol-4-yl)-5-chloropicolinamide (C66) (430 mg, 0.435 mmol, 1 eq) in ethanol (20 mL) was added methoxylamine hydrochloride (363 mg, 4.35 mmol, 10 eq) and pyridine (3.44 g, 43.5 mmol, 100 eq) at room temperature. The reaction mixture was stirred at 60° C. for 16 hours. The resulting solution was concentrated to afford crude product which was purified by achiral preparative HPLC (Column: Phenomenex Gemini C18 250 mm×21.2 mm×5 μm; Gradient: 46% acetonitrile in water containing 0.05% ammonia to 66% acetonitrile in water containing 0.05% ammonia; Gradient Time: 10 min; hold at 66% acetonitrile in water containing 0.05% ammonia for 2 min; flow rate: 30 mL/min) to afford (+/−)-N-(2-((4aR*,6R*,8aR*)-2-amino-6-(trifluoromethyl)-4,4a,5,6-tetrahydropyrano[3,4-d][1,3]oxazin-8a(8H)-yl)thiazol-4-yl)-5-chloropicolinamide (C67) (64 mg, 31.9% yield via 2 steps, 92.921% purity by LCMS m/z 462.0 [M+H]$^+$ with chlorine isotope pattern observed) as a white solid after lyophilization.

Step 3 (Chiral Separation)

(+/−)-N-(2-((4aR*,6R*,8aR*)-2-Amino-6-(trifluoromethyl)-4,4a,5,6-tetrahydro pyrano[3,4-d][1,3]oxazin-8a (8H)-yl)thiazol-4-yl)-5-chloropicolinamide (C67) (64 mg) was subjected to chiral supercritical fluid chromatography (Column: Chiralpak AD, 250 mm×30 mm, 5 μm; Mobile Phase: 6/4 carbon dioxide/ethanol containing 0.1% aqueous ammonium hydroxide; flow rate: 50 mL/min). After lyophilization, the first-eluting enantiomer was obtained as a white solid (13 mg) and was re-purified by two achiral preparative HPLC and lyophilization cycles (Column: Phenomenex Gemini C18 250 mm×50 mm, 10 μm; Mobile phase: 46% acetonitrile in water containing 0.05% ammonia to 66% acetonitrile in water containing 0.05% ammonia over 10 min, hold at 66% acetonitrile in water containing 0.05% ammonia for 2 min; flow rate: 30 mL/min). After final lyophilization (6 mg, 9.4% yield, white solid), the first enantiomer was assigned to N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-5-chloropicolinamide (10b) on the basis of this compound's biological activity (inactive). LCMS m/z 461.9 [M+H]$^+$ with chlorine isotope pattern observed. $^1$H NMR (400 MHz, CDCl$_3$) δ 10.39 (s, 1H), 8.53-8.62 (m, 1H), 8.24 (d, J=8.0 Hz, 1H), 7.88-7.93 (m, 1H), 7.76 (s, 1H), 4.29 (br. s., 2H), 3.85-4.08 (m, 5H), 2.75-2.83 (m, 1H), 1.84-1.96 (m, 2H).

After lyophilization, the second-eluting enantiomer was obtained as a white solid (11 mg) and re-purified by two achiral preparative HPLC and lyophilization cycles (Column: Phenomenex Gemini C18 250 mm×50 mm, 10 μm; Mobile phase: 46% acetonitrile in water containing 0.05% ammonia to 66% acetonitrile in water containing 0.05% ammonia over 10 min, hold at 66% acetonitrile in water containing 0.05% ammonia for 2 min; flow rate: 30 mL/min). After final lyophilization (8 mg, 12% yield, white solid), the second enantiomer was assigned N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-5-chloropicolinamide (10a) on the basis of this compound's biological activity (active). LCMS m/z 483.9 [M+Na]$^+$ with chlorine isotope pattern observed. $^1$H NMR (400 MHz, CDCl$_3$) δ 10.39 (br. s., 1H), 8.59 (d, J=2.0 Hz, 1H), 8.24 (d, J=8.0 Hz, 1H), 7.88-7.93 (m, 1H), 7.76 (s, 1H), 4.29 (br. s., 2H), 3.85-4.08 (m, 5H), 2.74-2.83 (m, 1H), 1.84-1.96 (m, 2H)

Example 11

Chiral N-(2-((4aS,6S,8aS)-2-amino-6-(trifluoromethyl)-4,4a,5,6-tetrahydropyrano [3,4-d][1,3]oxazin-8a(8H)-yl)thiazol-4-yl)-5-(difluoromethoxy)-3-methylpicolinamide (11a) and Chiral N-(2-((4aR,6R, 8aR)-2-amino-6-(trifluoromethyl)-4,4a,5,6-tetrahydropyrano [3,4-d][1,3]oxazin-8a(8H)-yl) thiazol-4-yl)-5-(difluoromethoxy)-3-methylpicolinamide (11b)

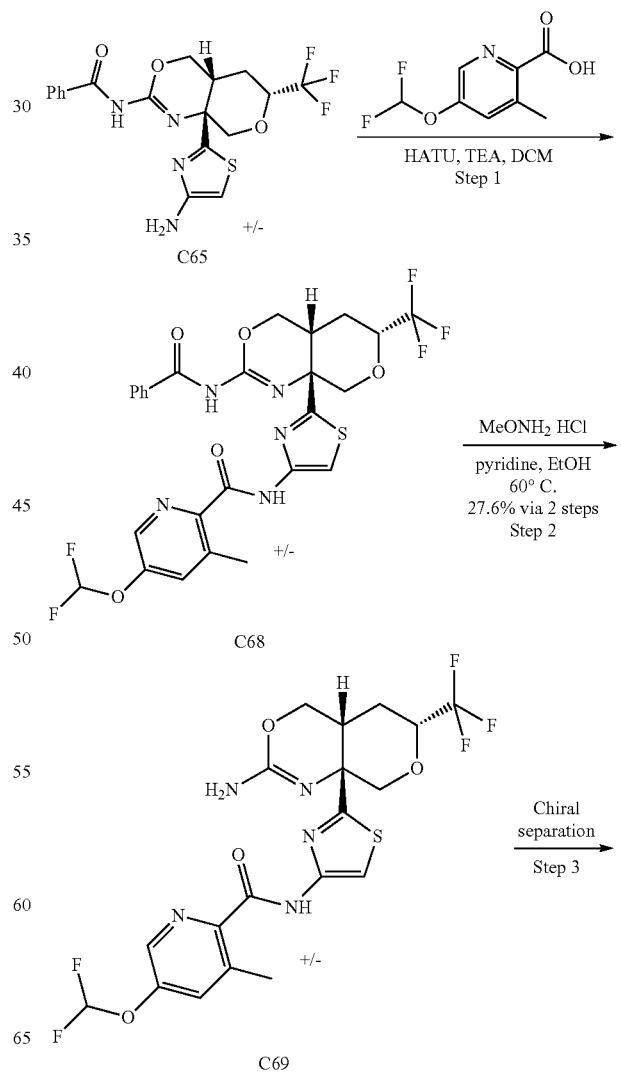

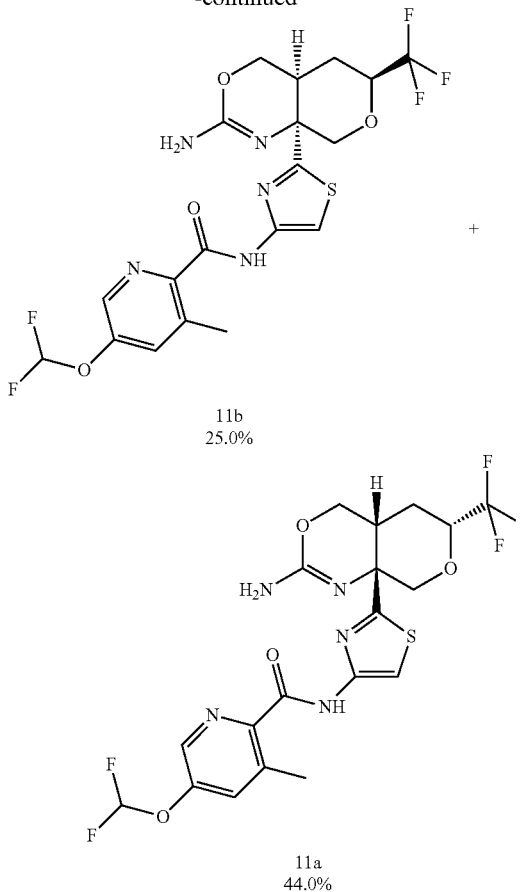

11b
25.0%

11a
44.0%

Step 1: Synthesis of (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide (C68)

This racemate was prepared according to the procedure for crude (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-chloropicolinamide (C66) using (+/−)-N-((4aR*,6R*,8aR*)-8a-(4-aminothiazol-2-yl)-6-(trifluoromethyl)-4,4a,5,6,8,8a-hexahydropyrano[3,4-d][1,3]oxazin-2-yl)benzamide (C65) (200 mg, 0.435 mmol), 5-(difluoromethoxy)-3-methylpicolinic acid (124 mg, 0.609 mmol), dichloromethane (20 mL), HATU (240 mg, 0.631 mmol, 1.45 eq) and triethylamine (75 mg, 0.741 mmol, 1.703 eq). Crude (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide (C68) (445 mg, 80.85% purity by LCMS m/z 612.1 [M+H]$^+$) was obtained as a thick yellow oil and used directly in the next step without further purification.

Step 2: Synthesis of (+/−)-N-(2-((4aR*,6R*,8aR*)-2-amino-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide (C69)

This racemate was prepared according to the procedure previously described for (+/−)-N-(2-((4aR*,6R*,8aR*)-2-amino-6-(trifluoromethyl)-4,4a,5,6-tetrahydropyrano[3,4-d][1,3]oxazin-8a(8H)-yl)thiazol-4-yl)-5-chloropicolinamide C67 using crude (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide (C68) (445 mg), ethanol (20 mL), methoxylamine hydrochloride (363 mg, 4.35 mmol) and pyridine (3.44 g, 43.5 mmol). Purification via achiral preparative HPLC (Column: Phenomenex Gemini C18 250 mm×21.2 mm, 5 μm; Gradient: 46% acetonitrile in water containing 0.05% ammonia to 66% acetonitrile in water containing 0.05% ammonia; Gradient Time: 10 min; hold at 66% acetonitrile in water containing 0.05% ammonia for 2 min; flow rate: 30 mL/min) afforded (+/−)-N-(2-((4aR*,6R*,8aR*)-2-amino-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide (C69) (61 mg, 27.6% yield via 2-steps, 90.93% purity by LCMS m/z 508.1 [M+H]$^+$) as a white solid after lyophilization.

Step 3 (Chiral Separation)

The racemate (C69) (61 mg) was subjected to chiral supercritical fluid chromatography (Column: Chiralpak AD, 250 mm×30 mm, 5 um; Mobile Phase: 75/25 carbon dioxide/ethanol containing 0.1% aqueous ammonium hydroxide; flow rate: 60 mL/min).

After lyophilization, the first-eluting enantiomer was obtained as a white solid (25 mg) and was re-purified by achiral preparative HPLC (Column: Phenomenex Luna C18 250 mm×50 mm, 10 μm; Mobile phase: 30% acetonitrile in water containing 0.05% ammonia to 70% acetonitrile in water containing 0.05% ammonia over 8 min, hold at 70% acetonitrile in water containing 0.05% ammonia for 1 min; flow rate: 35 mL/min). After lyophilization (15 mg, 25% yield, off-white solid), the first enantiomer was assigned to N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide (11b) on the basis of this compound's biological activity. LCMS m/z 508.0 [M+H]$^+$ $^1$H NMR (400 MHz, CDCl$_3$) δ 10.58 (s, 1H), 8.33 (d, J=1.5 Hz, 1H), 7.72 (s, 1H), 7.40-7.45 (m, 1H), 6.64 (t, $J_{HF}$=72.3 Hz, 1H), 4.23 (br. s., 2H), 3.94-4.09 (m, 3H), 3.89 (d, J=11.5 Hz, 2H), 2.84 (s, 3H), 2.74-2.81 (m, 1H), 1.82-1.99 (m, 2H).

After lyophilization, the second-eluting enantiomer was obtained as a white solid (27 mg, 44% yield) and assigned N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide (11a) on the basis of this compound's biological activity. LCMS m/z 508.0 [M+H]$^+$ $^1$H NMR (400 MHz, CDCl$_3$) δ 10.57 (s, 1H), 8.31-8.35 (m, 1H), 7.71 (s, 1H), 7.40-7.44 (m, 1H), 6.64 (t, $J_{HF}$=72.3 Hz, 1H), 4.27 (br. s., 2H), 3.94-4.09 (m, 3H), 3.89 (d, J=11.0 Hz, 2H), 2.84 (s, 3H), 2.74-2.81 (m, 1H), 1.82-1.99 (m, 2H).

Example 12

Chiral N-(2-((4aS,6S,8aS)-2-amino-6-(trifluoromethyl)-4,4a,5,6-tetrahydropyrano [3,4-d][1,3]oxazin-8a(8H)-yl)thiazol-4-yl)-5-(difluoromethoxy)picolinamide (12b) and Chiral N-(2-((4aR,6R,8aR)-2-amino-6-(trifluoromethyl)-4,4a,5,6-tetrahydropyrano [3,4-d][1,3]oxazin-8a(8H)-yl)thiazol-4-yl)-5-(difluoromethoxy)picolinamide (12a)

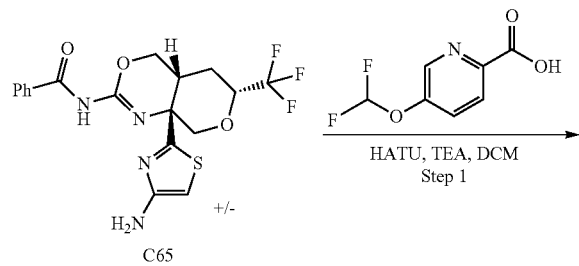

Step 1: Synthesis of (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-(difluoromethoxy) picolinamide (C70)

This racemate was prepared according to the procedure for crude (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-chloropicolinamide (C66) using (+/−)-N-((4aR*,6R*,8aR*)-8a-(4-aminothiazol-2-yl)-6-(trifluoromethyl)-4,4a,5,6,8,8a-hexahydropyrano[3,4-d][1,3]oxazin-2-yl)benzamide (C65) (200 mg, 0.435 mmol), 5-(difluoromethoxy) picolinic acid (115 mg, 0.609 mmol), dichloromethane (20 mL), HATU (240 mg, 0.631 mmol, 1.45 eq) and triethylamine (75 mg, 0.741 mmol, 1.703 eq). Crude (+/−)-N-(2-((4aR*,6R*,8aR*)-2-benzamido-6-(trifluoromethyl)-4,4a,5,6-tetrahydropyrano [3,4-d][1,3]oxazin-8a(8H)-yl)thiazol-4-yl)-5-(difluoromethoxy)picolinamide (C70) (395 mg, 84.91% purity by LCMS m/z 620.0 [M+Na]$^+$) was obtained as a white solid and used directly in the next step without further purification.

Step 2: Synthesis of (+/−)-N-(2-((4aR*,6R*,8aR*)-2-amino-6-(trifluoromethyl)-4,4a,5,6-tetrahydropyrano[3,4-d][1,3]oxazin-8a(8H)-yl)thiazol-4-yl)-5-(difluoromethoxy) picolinamide (C71)

This racemate was prepared according to the procedure previously described for (+/−)-N-(2-((4aR*,6R*,8aR*)-2-amino-6-(trifluoromethyl)-4,4a,5,6-tetrahydropyrano[3,4-d]

[1,3]oxazin-8a(8H)-yl)thiazol-4-yl)-5-chloropicolinamide (C67) using crude (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-(difluoromethoxy) picolinamide (C70) (395 mg), ethanol (20 mL), methoxylamine hydrochloride (363 mg, 4.35 mmol) and pyridine (3.44 g, 43.5 mmol). Purification via achiral preparative HPLC (Column: Phenomenex Gemini C18 250 mm×21.2 mm×5 μm; Gradient: 41% acetonitrile in water containing 0.05% ammonia to 61% acetonitrile in water containing 0.05% ammonia; Gradient Time: 10 min; hold at 61% acetonitrile in water containing 0.05% ammonia for 2 min; flow rate: 30 mL/min) afforded (+/−)-N-(2-((4aR*,6R*,8aR*)-2-amino-6-(trifluoromethyl)-4,4a,5,6-tetrahydropyrano[3,4-d][1,3]oxazin-8a(8H)-yl)thiazol-4-yl)-5-(difluoromethoxy) picolinamide (C71) (74 mg, 34.5% yield via 2-steps, 93.57% purity by LCMS m/z 494.1 [M+H]$^+$) as a white solid after lyophilization.

Step 5 (Chiral Separation)

The racemate (C71) (74 mg) was subjected to chiral supercritical fluid chromatography (Column: Chiralpak AD, 250 mm×30 mm, 5 μm; Mobile Phase: 65/35 carbon dioxide/ethanol containing 0.1% aqueous ammonium hydroxide; flow rate: 50 mL/min).

After lyophilization, the first-eluting enantiomer was obtained as a white solid (30 mg) and was re-purified by achiral preparative HPLC (Column: DuraShell C18 150 mm×25 mm, 5 μm; Mobile phase: 38% acetonitrile in water containing 0.05% ammonia to 58% acetonitrile in water containing 0.05% ammonia over 10 min, hold at 58% acetonitrile in water containing 0.05% ammonia for 2 min; flow rate: 30 mL/min). After lyophilization (16 mg, 22% yield, white solid), the first enantiomer was assigned to N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-5-(difluoromethoxy)picolinamide (12b) on the basis of this compound's biological activity. LCMS m/z 493.9 [M+H]$^+$ $^1$H NMR (400 MHz, CDCl$_3$) δ 10.39 (s, 1H), 8.46-8.51 (m, 1H), 8.32 (d, J=8.5 Hz, 1H), 7.75 (s, 1H), 7.68 (dd, J=1.8, 8.8 Hz, 1H), 6.66 (t, J$_{HF}$=72.0 Hz, 1H), 4.24 (br. s., 2H), 3.94-4.08 (m, 3H), 3.85-3.93 (m, 2H), 2.73-2.82 (m, 1H), 1.82-1.99 (m, 2H).

After lyophilization, the second-eluting enantiomer was obtained as a white solid (29 mg) and was re-subjected to chiral supercritical fluid chromatography (Column: Chiralpak AD, 250 mm×30 mm, 5 μm; Mobile Phase: 75/25 carbon dioxide/ethanol containing 0.1% aqueous ammonium hydroxide; flow rate: 60 mL/min), lyophilization, then achiral preparative HPLC (Column: DuraShell C18 150 mm×25 mm, 50 μm; Mobile phase: 38% acetonitrile in water containing 0.05% ammonia to 58% acetonitrile in water containing 0.05% ammonia over 10 min, hold at 58% acetonitrile in water containing 0.05% ammonia for 2 min; flow rate: 30 mL/min). After lyophilization, (14 mg, 19% yield, white solid), the second enantiomer was assigned to N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-5-(difluoromethoxy)picolinamide (12a) on the basis of this compound's biological activity. LCMS m/z 493.9 [M+H]$^+$ $^1$H NMR (400 MHz, CDCl$_3$) δ 10.39 (s, 1H), 8.48 (d, J=2.5 Hz, 1H), 8.32 (d, J=8.5 Hz, 1H), 7.75 (s, 1H), 7.68 (dd, J=2.5, 8.0 Hz, 1H), 6.66 (t, J$_{HF}$=720.0 Hz, 2H), 4.24 (br. s., 2H), 3.94-4.08 (m, 3H), 3.85-3.93 (m, 2H), 2.73-2.82 (m, 1H), 1.82-1.99 (m, 2H).

Example 13

Chiral N-(2-((4aS,6S,8aS)-2-amino-6-(trifluoromethyl)-4,4a,5,6-tetrahydropyrano [3,4-d][1,3]oxazin-8a(8H)-yl)thiazol-4-yl)-3-chloro-5-(difluoromethoxy)picolinamide (13b) and Chiral N-(2-((4aR,6R,8aR)-2-amino-6-(trifluoromethyl)-4,4a,5,6-tetrahydropyrano [3,4-d][1,3]oxazin-8a(8H)-yl)thiazol-4-yl)-3-chloro-5-(difluoromethoxy)picolinamide (13a)

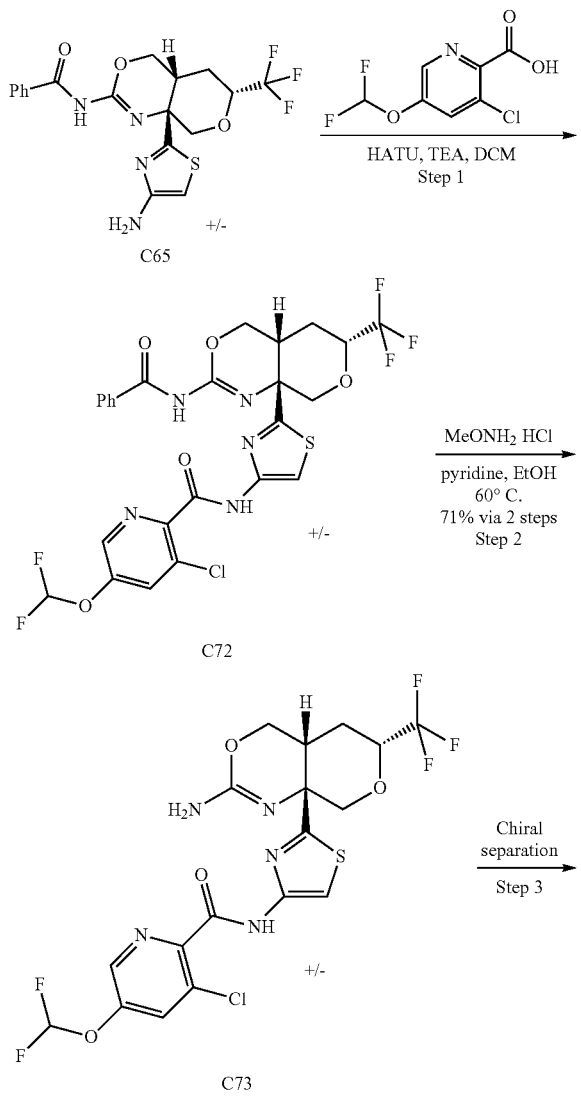

-continued

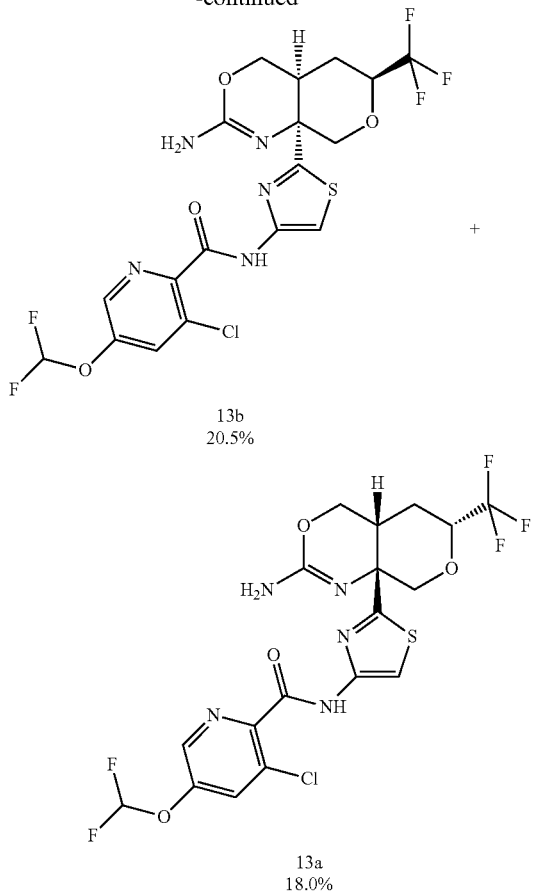

13b
20.5%

13a
18.0%

Step 1: Synthesis of (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-3-chloro-5-(difluoromethoxy)picolinamide (C72)

This racemate was prepared according to the procedure for crude (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-5-chloropicolinamide (C66) using (+/−)-N-((4aR*,6R*,8aR*)-8a-(4-aminothiazol-2-yl)-6-(trifluoromethyl)-4,4a,5,6,8,8a-hexahydro pyrano[3,4-d][1,3]oxazin-2-yl)benzamide (C65) (200 mg, 0.435 mmol), 3-chloro-5-(difluoromethoxy)picolinic acid (122 mg, 0.544 mmol), dichloromethane (20 mL), HATU (240 mg, 0.631 mmol, 1.45 eq) and triethylamine (75 mg, 0.741 mmol, 1.703 eq). (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-3-chloro-5-(difluoromethoxy)picolinamide (C72) (460 mg, 88.25% purity by LCMS m/z 654.0 [M+Na]+ with chlorine isotope pattern observed) was obtained as a thick yellow oil and used directly in the next step without further purification.

Step 2: Synthesis of (+/−)-N-(2-((4aR*,6R*,8aR*)-2-amino-6-(trifluoromethyl)-4,4a,5,6-tetrahydropyrano[3,4-d][1,3]oxazin-8a(8H)-yl)thiazol-4-yl)-3-chloro-5-(difluoromethoxy)picolinamide (C73)

The title compound (C73) was prepared according to the procedure previously described for (+/−)-N-(2-((4aR*,6R*,8aR*)-2-amino-6-(trifluoromethyl)-4,4a,5,6-tetrahydropyrano[3,4-d][1,3]oxazin-8a(8H)-yl)thiazol-4-yl)-5-chloropicolinamide (C67) using crude (+/−)-N-(2-((4aR*,6R*,8aR*)-2-benzamido-6-(trifluoromethyl)-4,4a,5,6-tetrahydropyrano[3,4-d][1,3]oxazin-8a(8H)-yl)thiazol-4-yl)-3-chloro-5-(difluoromethoxy) picolinamide (C72) (462 mg), ethanol (20 mL), methoxylamine hydrochloride (363 mg, 4.35 mmol) and pyridine (3.44 g, 43.5 mmol). Purification via achiral preparative HPLC (Column: Phenomenex Gemini C18 250 mm×21.2 mm×5 μm; Gradient: 44% acetonitrile in water containing 0.05% ammonia to 64% acetonitrile in water containing 0.05% ammonia; Gradient Time: 10 min; hold at 64% acetonitrile in water containing 0.05% ammonia for 2 min; flow rate: 30 mL/min) afforded (+/−)-N-(2-((4aR*,6R*,8aR*)-2-amino-6-(trifluoromethyl)-4,4a,5,6-tetrahydropyrano[3,4-d][1,3] oxazin-8a(8H)-yl)thiazol-4-yl)-3-chloro-5-(difluoromethoxy)picolinamide (C73) (163 mg, 71.0% yield via 2-steps, 93.18% purity by LCMS m/z 528.1 [M+H] with chlorine isotope pattern observed) as a white solid.

Step 9 (Chiral Separation)

The racemate (C73) (163 mg) was subjected to chiral supercritical fluid chromatography (Column: Chiralpak AD, 250 mm×30 mm, 5 μm; Mobile Phase: 75/25 carbon dioxide/isopropanol containing 0.1% aqueous ammonium hydroxide; flow rate: 60 mL/min).

After lyophilization, the first-eluting enantiomer was obtained as a white solid (52 mg) and was re-purified by achiral preparative HPLC (Column: DuraShell C18 150 mm×25 mm, 5 μm; Mobile phase: 41% acetonitrile in water containing 0.05% ammonia to 61% acetonitrile in water containing 0.05% ammonia over 10 min, hold at 61% acetonitrile in water containing 0.05% ammonia for 2 min; flow rate: 30 mL/min). After lyophilization (22 mg, 20.5% yield, white solid), the first enantiomer was assigned to N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-3-chloro-5-(difluoromethoxy)picolinamide on the basis of this compound's biological activity (13b) (inactive). LCMS m/z 527.9 [M+H]+ with chlorine isotope pattern observed. $^1$H NMR (400 MHz, CDCl$_3$) δ 10.34 (s, 1H), 8.42 (d, J=2.0 Hz, 1H), 7.78 (s, 1H), 7.70 (d, J=2.5 Hz, 1H), 6.67 (t, J$_{HF}$=71.3 Hz, 1H), 4.24 (br. s., 2H), 3.94-4.08 (m, 3H), 3.84-3.92 (m, 2H), 2.72-2.80 (m, 1H), 1.81-1.99 (m, 2H).

After lyophilization, the second-eluting enantiomer was obtained as a white solid (47 mg) and was re-purified by achiral preparative HPLC (Column: DuraShell C18 150 mm×25 mm, 5 μm; Mobile phase: 41% acetonitrile in water containing 0.05% ammonia to 61% acetonitrile in water containing 0.05% ammonia over 10 min, hold at 61% acetonitrile in water containing 0.05% ammonia for 2 min; flow rate: 30 mL/min). After lyophilization (19 mg, 18% yield, white solid), the second enantiomer was assigned to N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-3-chloro-5-(difluoromethoxy)picolinamide on the basis of this compound's biological activity (13a) (active,). LCMS m/z 527.9 [M+H]$^+$ with chlorine isotope pattern observed. $^1$H NMR (400 MHz, CDCl$_3$) δ 10.34 (s, 1H), 8.34 (d, J=2.5 Hz, 1H), 7.78 (s, 1H), 7.70 (d, J=2.0 Hz, 1H), 6.67 (t, J$_{HF}$=71.3 Hz, 1H), 4.23 (br. s., 2H), 3.94-4.08 (m, 3H), 3.85-3.93 (m, 2H), 2.72-2.80 (m, 1H), 1.82-1.99 (m, 2H).

Preparation P10

N-((4a'R,8a'R)-8a'-(4-aminothiazol-2-yl)-4a',5',8',8a'-tetrahydro-4'H-spiro[cyclobutane-1,6'-pyrano[3,4-d][1,3]oxazin-2'-yl)benzamide (C84)

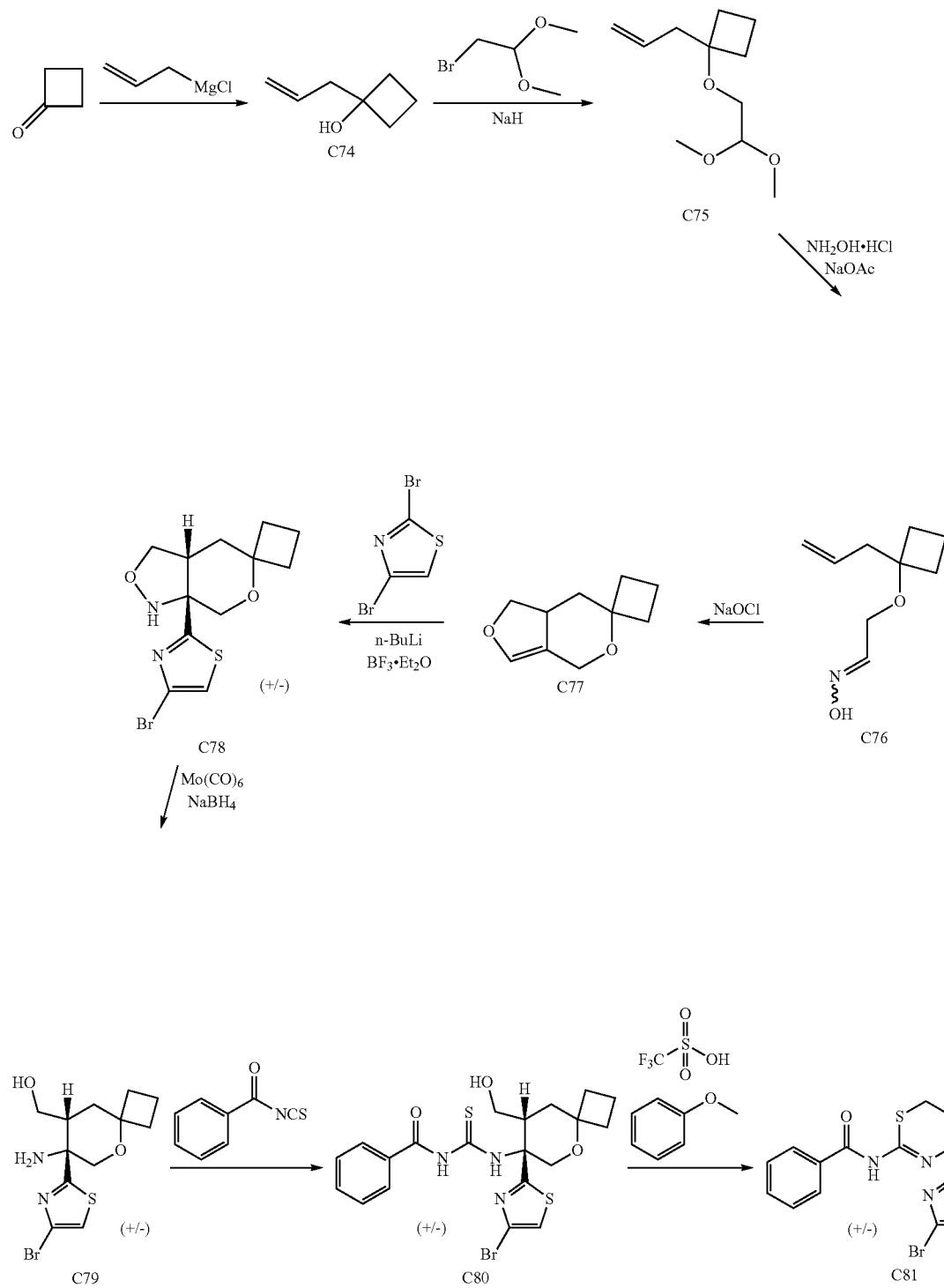

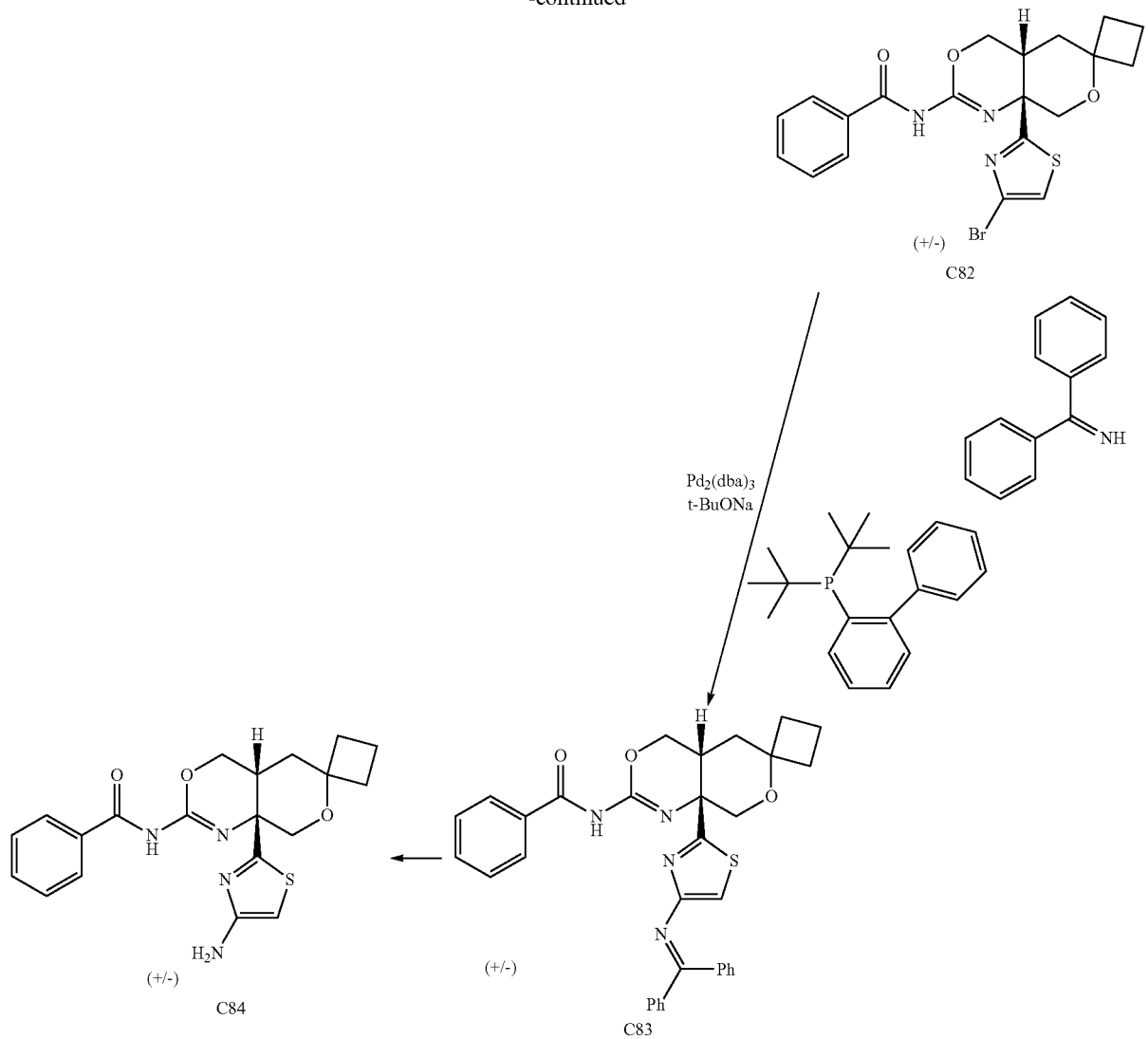

Step 1. Synthesis of 1-(prop-2-en-1-yl)cyclobutanol (C74)

Allylmagnesium chloride (2.0 M solution in tetrahydrofuran; 85.6 mL, 171 mmol) was added in a drop-wise manner to a 0° C. solution of cyclobutanone (6.00 g, 85.6 mmol) in tetrahydrofuran (60 mL). The reaction mixture was stirred at 0° C. for 1 hour and then at room temperature for 1 hour, whereupon saturated aqueous ammonium chloride solution (150 mL) was added, followed by aqueous hydrochloric acid (6 M, 25 mL). The resulting mixture was extracted with ethyl acetate (3×100 mL), and the combined organic layers were washed with saturated aqueous sodium bicarbonate solution (3×150 mL) until a basic pH was observed for the aqueous layer. The organic layer was washed with saturated aqueous sodium chloride solution (150 mL), dried over sodium sulfate, filtered, concentrated in vacuo, and adsorbed onto silica gel. Chromatography on silica gel (Gradient: 0% to 60% ethyl acetate in heptane) provided the product as a colorless oil. Yield: 5.13 g, 45.7 mmol, 53%. $^1$H NMR (400 MHz, CDCl$_3$) δ 5.94-5.83 (m, 1H), 5.22-5.20 (m, 1H), 5.20-5.16 (m, 1H), 2.39 (br d, J=7.2 Hz, 2H), 2.10-2.04 (m, 4H), 1.81-1.71 (m, 1H), 1.61-1.49 (m, 1H).

Step 2. Synthesis of 1-(2,2-dimethoxyethoxy)-1-(prop-2-en-1-yl)cyclobutane (C75)

To a suspension of sodium hydride (60% in mineral oil; 3.84 g, 96.0 mmol) in 1,4-dioxane (60 mL) was added C74 (5.13 g, 45.7 mmol) in a drop-wise manner. After the reaction mixture had been stirred for 45 minutes at room temperature, 2-bromo-1,1-dimethoxyethane (10.8 mL, 91.4 mmol) was slowly added, and the reaction mixture was heated at 100° C. for 16 hours, whereupon it was cooled and poured into ice water (800 mL). The resulting mixture was extracted with ethyl acetate (3×150 mL), and the combined organic layers were washed with saturated aqueous sodium chloride solution (2×200 mL), dried over sodium sulfate, filtered, and concentrated in vacuo. Chromatography on silica gel (Gradient: 0% to 70% ethyl acetate in heptane) afforded the product as a colorless oil. Yield: 3.45 g, 17.2 mmol, 38%. $^1$H NMR (400 MHz, CDCl$_3$) δ 5.91-5.80 (m, 1H), 5.17-5.12 (m, 1H), 5.12-5.08 (m, 1H), 4.46 (t, J=5.2 Hz, 1H), 3.40 (s, 6H), 3.36 (d, J=5.2 Hz, 2H), 2.41 (br d, J=7.0 Hz, 2H), 2.17-2.07 (m, 2H), 1.97-1.89 (m, 2H), 1.80-1.70 (m, 1H), 1.61-1.48 (m, 1H).

Step 3. Synthesis of N-hydroxy-2-{[1-(prop-2-en-1-yl)cyclobutyl]oxy}ethanimine (C76)

Hydroxylamine hydrochloride (1.72 g, 24.8 mmol) was added to a solution of C75 (3.45 g, 17.2 mmol) in ethanol (28 mL) and water (5 mL). The reaction mixture was heated to 70° C. for 90 minutes, whereupon it was cooled to room temperature and treated with a solution of sodium acetate (97%, 2.91 g, 34.4 mmol) in water (5 mL). The resulting mixture was stirred at room temperature for 10 minutes and concentrated in vacuo; the residue was partitioned between dichloromethane (100 mL) and water (150 mL). The aqueous layer was extracted with dichloromethane (2×150 mL), and the combined organic layers were washed with saturated aqueous sodium chloride solution (300 mL), dried over sodium sulfate, filtered, and concentrated under reduced pressure to afford the product as a colorless oil. By $^1$H NMR, this material was judged to be a mixture of geometric isomers around the oxime. Yield: 2.72 g, 16.1 mmol, 94%. $^1$H NMR (400 MHz, CDCl$_3$) δ [7.49 (t, J=5.6 Hz) and 6.90 (br t, J=3 Hz), total 1H], 5.90-5.77 (m, 1H), 5.18-5.14 (m, 1H), 5.14-5.10 (m, 1H), [4.23 (br d, J=3.5 Hz) and 3.99 (d, J=5.5 Hz), total 2H], 2.43 (br d, J=7 Hz, 2H), 2.18-2.07 (m, 2H), 2.00-1.92 (m, 2H), 1.83-1.73 (m, 1H), 1.65-1.51 (m, 1H).

Step 4. Synthesis of 3a', 4'-dihydro-3'H, 7'H-spiro [cyclobutane-1,5'-pyrano[3,4-c][1,2]oxazole] (C77)

Sodium hypochlorite solution (5.6-6%, 21.2 mL, 18 mmol) was added in a drop-wise manner to a solution of C76 (2.72 g, 16.1 mmol) in dichloromethane (76 mL) at an internal temperature of −10° C., at a rate such that the internal temperature of the reaction never rose above 0° C. After completion of the addition, the reaction mixture was stirred at −10° C. for 3 hours, whereupon it was allowed to warm slowly to room temperature over 16 hours. The reaction mixture was diluted with water (500 mL), and the aqueous layer was extracted with dichloromethane (2×250 mL). The combined organic layers were washed with saturated aqueous sodium chloride solution (500 mL), dried over sodium sulfate, filtered, and adsorbed onto silica gel. Chromatography on silica gel (Gradient: 0% to 80% ethyl acetate in heptane) provided the product as a colorless oil. Yield: 2.06 g, 12.3 mmol, 76%. $^1$H NMR (400 MHz, CDCl$_3$) δ 4.60 (dd, J=10.2, 7.9 Hz, 1H), 4.52 (d, J=13.6 Hz, 1H), 4.20 (dd, J=13.6, 1.3 Hz, 1H), 3.80 (dd, J=11.6, 7.9 Hz, 1H), 3.52-3.40 (m, 1H), 2.40 (dd, J=12.9, 6.3 Hz, 1H), 2.30-2.20 (m, 1H), 2.19-2.02 (m, 2H), 2.00-1.83 (m, 2H), 1.76-1.57 (m, 2H).

Step 5. Synthesis of cis-7a'-(4-bromo-1,3-thiazol-2-yl)tetrahydro-1'H,3'H-spiro[cyclobutane-1,5'-pyrano [3,4-c][1,2]oxazole] (C78)

To a −76° C. (internal temperature) solution of 2,4-dibromo-1,3-thiazole (3.78 g, 15.6 mmol) in a mixture of toluene and tetrahydrofuran (10:1, 80 mL) was added boron trifluoride diethyl etherate (1.85 mL, 14.6 mmol), followed by drop-wise addition of n-butyllithium (2.5 M solution in hexanes; 5.74 mL, 14.4 mmol). The internal temperature of the reaction mixture was maintained below −70° C. throughout both of these additions. The reaction mixture was then stirred at −76° C. (internal temperature) for 30 minutes, whereupon a solution of C77 (2.0 g, 12.0 mmol) in a mixture of toluene and tetrahydrofuran (10:1, 6 mL) was added. Additional toluene/tetrahydrofuran (10:1, 6 mL) was used to rinse the C77 flask; this was also added to the reaction mixture. Stirring was continued at −76° C. for 1 hour, at which time the reaction was quenched via addition of saturated aqueous ammonium chloride solution (200 mL) and then allowed to warm to room temperature. The resulting mixture was partitioned between ethyl acetate (200 mL) and water (500 mL); the organic layer was washed with saturated aqueous sodium chloride solution (300 mL), dried over sodium sulfate, filtered, and concentrated under reduced pressure. Chromatography on silica gel (Gradient: 0% to 80% ethyl acetate in heptane) afforded the product as a yellow solid. Yield: 3.32 g, 10.0 mmol, 83%. LCMS m/z 331.3, 333.2 [M+H]$^+$. $^1$H NMR (400 MHz, CDCl$_3$) δ 7.21 (s, 1H), 3.96 (d, J=12.8 Hz, 1H), 3.76-3.70 (m, 3H), 3.41-3.34 (m, 1H), 2.31-2.09 (m, 4H), 2.02-1.93 (m, 1H), 1.91-1.80 (m, 1H), 1.74-1.59 (m, 2H).

Step 6. Synthesis of [rel-(7R,8R)-7-amino-7-(4-bromo-1,3-thiazol-2-yl)-5-oxaspiro[3.5]non-8-yl] methanol (C79)

Conversion of C78 to C79 was carried out according to the procedure described for synthesis of C30 from C31 in Example 6. The product was isolated as an orange solid. Yield: 3.2 g, 9.6 mmol, 96%. $^1$H NMR (400 MHz, CDCl$_3$), characteristic peaks: δ 7.20 (s, 1H), 3.75 (d, J=11.5 Hz, 1H), 3.70 (dd, J=11.4, 3.7 Hz, 1H), 3.51 (dd, J=11.4, 3.9 Hz, 1H), 3.30 (d, J=11.5 Hz, 1H), 2.49-2.41 (m, 1H), 2.27-1.80 (m, 6H), 1.74-1.61 (m, 1H).

Step 7. Synthesis of N-{[rel-(7R,8R)-7-(4-bromo-1,3-thiazol-2-yl)-8-(hydroxymethyl)-5-oxaspiro[3.5] non-7-yl]carbamothioyl}benzamide (C80)

To a solution of C79 (2.2 g, 6.6 mmol) in dichloromethane (100 mL) was added benzoyl isothiocyanate (0.938 mL, 6.98 mmol). The reaction mixture was stirred at room temperature for 16 hours, whereupon it was concentrated in vacuo to provide the product as a yellow solid (3.3 g). This material was used directly in the following step.

Step 8. Synthesis of N-[cis-8a'-(4-bromo-1,3-thiazol-2-yl)-4a',5',8',8a'-tetrahydro-4'H-spiro[cyclobutane-1,6'-pyrano[3,4-d][1,3]thiazin]-2'-yl]benzamide (C81) and N-((4a'R,8a'R)-8a'-(4-bromothiazol-2-yl)-4a',5',8',8a'-tetrahydro-4'H-spiro[cyclobutane-1,6'-pyrano[3,4-d][1,3]oxazin]-2'-yl)benzamide (C82)

Trifluoromethanesulfonic acid (1.74 mL, 19.7 mmol) was rapidly added to a mixture of C24 (from the previous step, 3.3 g, ≤6.6 mmol) and methoxybenzene (2.17 mL, 20.0 mmol) in 1,2-dichloroethane (44 mL). The reaction mixture was stirred at room temperature for 30 minutes, whereupon it was diluted with dichloromethane (100 mL) and treated with 1 M aqueous sodium hydroxide solution (150 mL). The resulting biphasic mixture was stirred at room temperature for 15 minutes, at which time the aqueous layer was extracted with dichloromethane (2×100 mL); the combined organic layers were washed with saturated aqueous sodium chloride solution (250 mL), dried over sodium sulfate, filtered, and concentrated in vacuo. The resulting yellow solid was triturated with heptane (15 mL) to afford the product 81 (1.08 g) as a white solid. The filtrate from the trituration was concentrated under reduced pressure, dissolved in a mixture of dichloromethane and methanol (9:1), and adsorbed onto silica gel. Chromatography on silica gel (Gradient: 0% to 70% ethyl acetate in heptane) provided an off-white solid, which was triturated with heptane to provide additional product (0.77 g) as a white solid. Combined yield: 1.85 g, 3.87 mmol, 59% over 2 steps. $^1$H NMR (400 MHz, CDCl$_3$) δ 8.24-7.88 (br s, 2H), 7.60-7.52 (m, 1H), 7.52-7.40 (m, 2H), 7.23 (s, 1H), 3.82 (AB quartet, downfield doublet is broadened, $J_{AB}$=11.6 Hz, $\Delta v_{AB}$=85.4 Hz, 2H), 3.23-3.14 (m, 1H), 3.14-3.02 (m, 1H), 2.61 (br d, J=12.5 Hz, 1H), 2.31-2.11 (m, 3H), 2.11-1.95 (m, 2H), 1.93-1.80 (m, 2H), 1.75-1.61 (m, 1H). A small amount of C82 was also isolated from this reaction. This was combined with samples obtained from other similar reactions and used directly in the next step LCMS m/z 464.3 [M+H]$^+$ bromine isotope pattern observed. $^1$H NMR (400 MHz, CDCl$_3$) δ ppm 8.20-8.30 (m, 2H), 7.51 (m, J=7.4 Hz, 1H), 7.41-7.48 (m, 2H), 7.27 (s, 1H), 4.16-4.34 (m, 2H), 4.00 (d, J=12.5 Hz, 1H), 3.78 (br. s., 1H), 2.94-3.02 (m, 1H), 2.11-2.31 (m, 3H), 1.94-2.02 (m, 2H), 1.79-1.92 (m, 2H), 1.67 (m, J=11.5, 9.3, 9.3 Hz, 1H).

Step 9. N-((4a'R,8a'R)-8a'-(4-aminothiazol-2-yl)-4a',5',8',8a'-tetrahydro-4'H-spiro[cyclobutane-1,6'-pyrano[3,4-d][1,3]oxazin]-2'-yl)benzamide (C84)

To a flask containing C82 (68 mg, 0.15 mmol) was added tris (dibenzylideneacetone)dipalladium(0) (96% 12.2 mg, 13.4 μmol), [1,1'-biphenyl]-2-yldi-tert-butylphosphane (John Phos) (9.30 mg, 0.0312 mmol), sodium tert-butoxide (47.1 mg, 0.490 mmol) and benzophenone imine (32.3 mg, 0.178 mmol, 29.8 μL), followed by toluene (0.94 mL). The mixture was evacuated three times and back-filled with N$_2$. The mixture was stirred at 60° C. for 1 hour. Analysis by LCMS indicated that no starting material remained and the desired product molecular weight for the imine was observed: LCMS m/z 563.7 [M+H]$^+$. The reaction mixture was filtered through celite, then concentrated in vacuo. The recovered C83 was an amber oil and this material was used directly in the next step. C83 (83.0 mg, 0.15 mmol) was dissolved in methanol (2 mL) and hydroxylamine.HCl (20.5 mg, 0.295 mmol) and sodium acetate (24.2 mg, 0.295 mmol) were added. The reaction mixture was stirred at ambient temperature for ~45 mins. Analysis by LCMS showed complete deprotection. The reaction was quenched with saturated aqueous sodium bicarbonate and extracted twice with ethyl acetate. The combined organic extracts were washed with brine, and dried over sodium sulfate, followed by concentration in vacuo. The residue was chromatographed (SIM) on a 4 g gold column eluting with a 0-100% ethyl acetate/heptane gradient. There was recovered a yellow solid. Yield: 651 mg, 1.15 mmol, 55%. LCMS m/z 399.3 [M+H]$^+$ $^1$H NMR (400 MHz, CDCl$_3$) δ ppm 8.22-8.27 (m, 2H), 7.46-7.53 (m, 1H), 7.38-7.45 (m, 2H), 5.94 (s, 1H), 4.33 (dd, J=11.7, 2.7 Hz, 1H), 3.97-4.17 (m, 4H), 3.72 (d, J=12.5 Hz, 1H), 2.82-2.90 (m, 1H), 2.21 (m, J=9.0 Hz, 3H), 1.78-2.01 (m, 4H), 1.60-1.73 (m, 1H)

Example 14 Synthesis of N-(2-((4a'R,8a'R)-2'-amino-4a',5'-dihydro-4'H-spiro [cyclobutane-1,6'-pyrano 3,4-d][1,3]oxazin]-8a'(8'H)-yl)thiazol-4-yl)-5-(difluoromethoxy) picolinamide

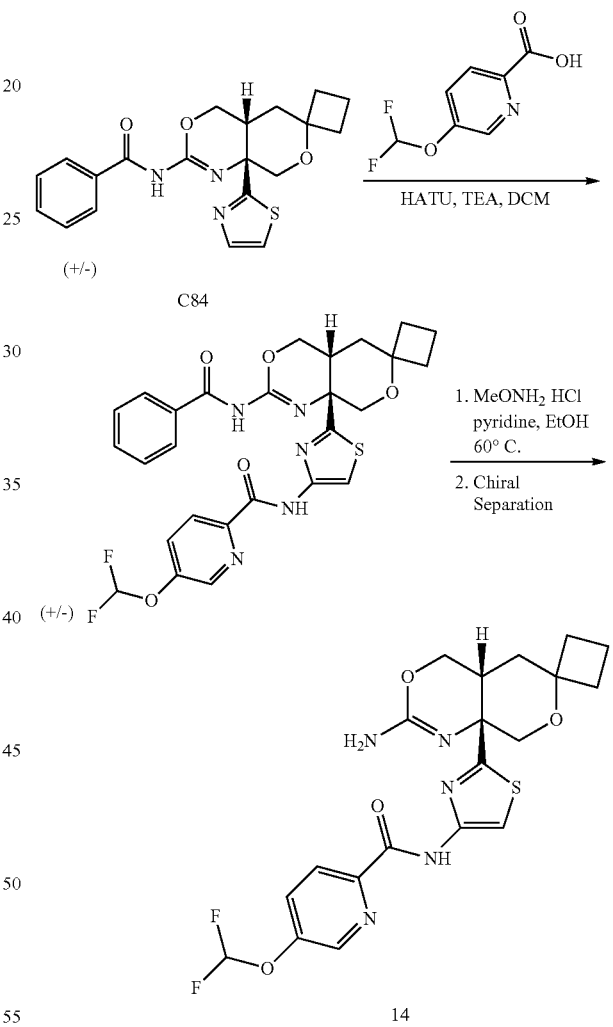

Conversion of C84 to Example 14 was carried out according to the procedure described for the conversion of C65 to Example 10a LCMS m/z 466.4 [M+H]$^+$. $^1$H NMR (400 MHz, CDCl$_3$) δ ppm 10.37 (s, 1H), 8.48 (d, J=2.7 Hz, 1H), 8.31 (dd, J=8.6, 0.8 Hz, 1H), 7.70 (s, 1H), 7.67 (dd, J=8.6, 2.7 Hz, 1H), 6.45-6.83 (m, 1H), 4.15 (br. s., 2H), 4.03 (dd, J=11.0, 2.7 Hz, 1H), 3.78-3.88 (m, 2H), 3.62 (d, J=11.7 Hz, 1H), 2.65-2.73 (m, 1H), 2.11-2.31 (m, 3H), 1.93-2.02 (m, 1H), 1.75-1.91 (m, 3H), 1.61-1.73 (m, 1H).

Example 15 Synthesis of N-(2-((4a'R,8a'R)-2'-amino-4a',5'-dihydro-4'H-spiro [cyclobutane-1,6'-pyrano [3,4-d][1,3]oxazin]-8a'(8'H)-yl)thiazol-4-yl)-5-(difluoromethoxy)-3-methyl picolinamide

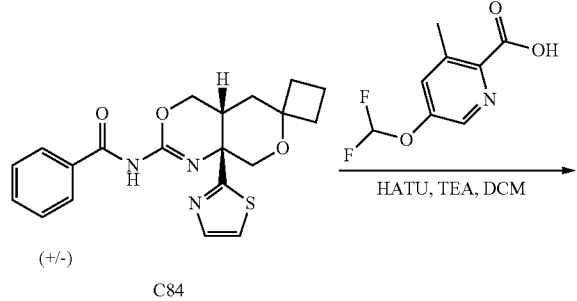

(+/-)
C84

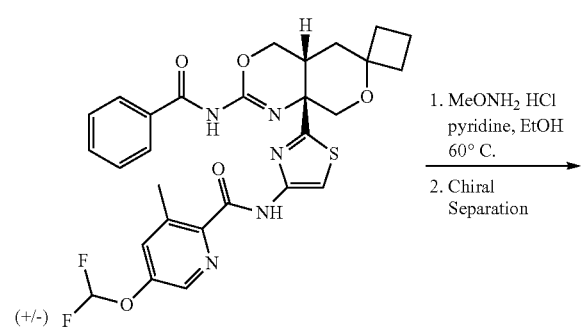

(+/-)

1. MeONH₂ HCl pyridine, EtOH 60° C.
2. Chiral Separation

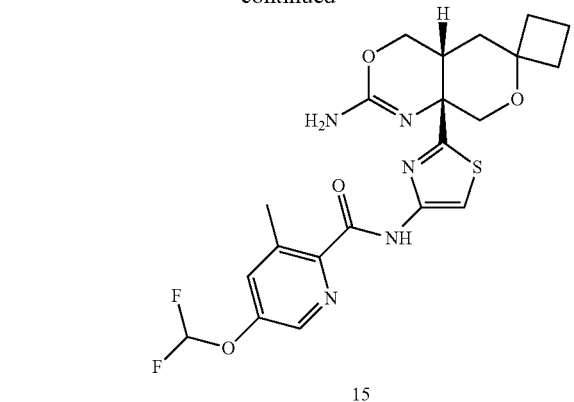

15

Conversion of C84 to Example 15 was carried out according to the procedure described for the conversion of C65 to Example 10a LCMS m/z 480.4 [M+H]⁺. ¹H NMR (400 MHz, CDCl₃) δ ppm 10.54 (s, 1H), 8.27-8.38 (m, 1H), 7.67 (s, 1H), 7.39-7.42 (m, 1H), 6.43-6.81 (m, 1H), 4.15 (br. s., 2H), 4.03 (dd, J=11.0, 3.1 Hz, 1H), 3.78-3.88 (m, 2H), 3.62 (d, J=11.4 Hz, 1H), 2.83 (s, 3H), 2.65-2.73 (m, 1H), 2.10-2.32 (m, 3H), 1.93-2.02 (m, 1H), 1.75-1.90 (m, 3H), 1.62-1.73 (m, 1H).

The compounds of Examples 16-19 can be prepared in a manner analogous to the preparation of the compounds of Examples 14 and 15 by coupling an appropriate acid of general formula R¹CO₂H with C84, followed by deprotection and chiral separation. The compounds of Examples 20-24 can be prepared in a manner analogous to the preparation of the compounds of Examples 10-13 (more specifically 10a, 11a, 12a and 13a) by coupling an appropriate acid of general formula R¹CO₂H with C65, followed by deprotection and chiral separation.

| Example Number | Method of Preparation; Intermediates | Structure | ¹H NMR (400 MHz, CDCl₃) δ (ppm); Mass spectrum, observed ion m/z (M + H⁺) or HPLC retention time; Mass spectrum m/z [M + H]⁺ (unless otherwise indicated) |
|---|---|---|---|
| 16 | Analogous to Examples 14-15; using C84 and 5-cyano picolinic acid | (structure shown) | ¹H NMR (400 MHz, Chloroform-d) δ 10.43 (s, 1H), 8.92 (dd, J = 2.0, 0.8 Hz, 1H), 8.42 (dd, J = 8.1, 0.9 Hz, 1H), 8.22 (dd, J = 8.1, 2.0 Hz, 1H), 7.77 (s, 1H), 5.25-4.25 (b, 2H), 4.07 (dd, J = 11.0, 2.8 Hz, 1H), 3.87 (dd, J = 14.5, 11.2 Hz, 2H), 3.69 (d, J = 11.6 Hz, 1H), 2.72 (d, J =12.9 Hz, 1H), 2.22 (m, 3H), 1.99 (m, 1H), 1.92-1.75 (m, 3H), 1.74-1.62 (m, 1H). |

-continued

| Example Number | Method of Preparation; Intermediates | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 17 | Analogous to Examples 14-15; using C84 and 5-(difluoromethoxy)pyrazine-2-carboxylic acid | 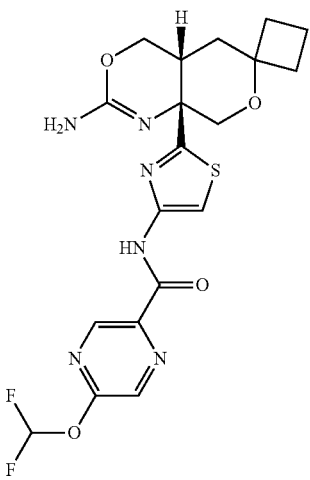 [SMILES: NC1=N[C@@]2(c3nc(NC(=O)c4cnc(OC(F)F)cn4)cs3)COC3(CCC3)C[C@H]2CO1] | $^1$H NMR(400 MHz, Chloroform-d) δ 10.09 (s, 1H), 9.06 (d, J = 1.3 Hz, 1H), 8.36 (d, J =1.4 Hz, 1H), 7.72 (s, 1H), 7.51 (t, J = 72.9 Hz, 1H), 4.65 (b, 2H), 4.04 (dd, J = 10.9, 2.9 Hz, 1H), 3.84 (dd, J = 11.0, 7.4 Hz, 2H), 3.65 (d, J = 11.5 Hz, 1H), 2.69 (d, J = 12.6 Hz, 1H), 2.35-2.09 (m, 3H), 2.06-1.92 (m, 1H), 1.91-1.74 (m, 3H), 1.69 (q, J = 9.5 Hz, 1H) |
| 18 | Analogous to Examples 14-15; using C84 and 3-chloro-5-(difluoromethoxy)picolinic acid | 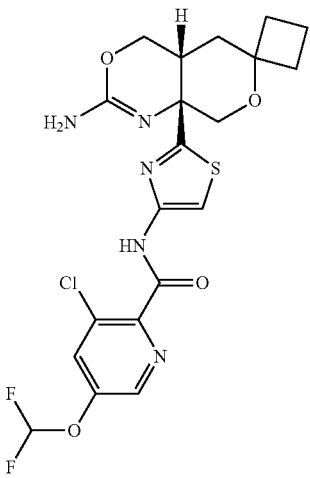 [SMILES: NC1=N[C@@]2(c3nc(NC(=O)c4ncc(OC(F)F)cc4Cl)cs3)COC3(CCC3)C[C@H]2CO1] | $^1$H NMR (400 MHz, DMSO-d$_6$) δ 11.42 (s, 1H), 8.53 (d, J = 2.4 Hz, 1H), 8.07 (d, J = 2.4 Hz, 1H), 7.66 (s, 1H), 7.39 (t, J = 72.7 Hz, 1H), 5.77 (s, 2H), 3.81 (d, J = 2.1 Hz, 2H), 3.68 (d, J =11.1 Hz, 1H), 3.40 (d, 2H), 2.55 (b, 1H), 2.17-1.83 (m, 5H), 1.74 (d, J = 10.2 Hz, 1H), 1.64 (q, J = 9.3 Hz, 1H), 1.52 (t, J =13.1 Hz, 1H). |
| 19 | Analogous to Examples 14-15; using C84 and 5-cyano-3-methyl picolinic acid | 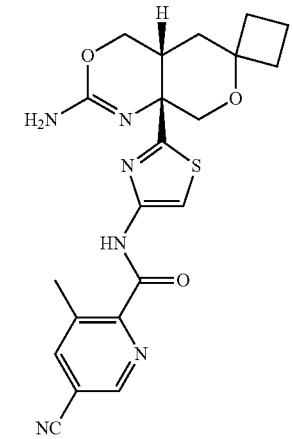 [SMILES: Cc1cc(C#N)cnc1C(=O)Nc1csc([C@]23COC4(CCC4)C[C@H]2COC(N)=N3)n1] | $^1$H NMR (400 MHz, Chloroform-d) δ 10.58 (s, 1H), 8.74 (d, J = 1.9 Hz, 1H), 8.01-7.90 (d, J = 1.9 Hz, 1H), 7.74 (s, 1H), 5.50-4.50 (b, 2H), 4.09 (dd, J = 11.0, 2.8 Hz, 1H), 3.90 (d, J = 11.0 Hz, 1H), 3.85 (d, J = 11.7 Hz, 1H), 3.72 (d, J = 11.7 Hz, 1H), 2.87 (s, 3H), 2.74 (d, J = 13.1 Hz, 1H), 2.22 (m, 3H), 1.99 (m, 1H), 1.92-1.74 (m, 3H), 1.68 (m, 1H). |

| Example Number | Method of Preparation; Intermediates | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 20 | Analogous to Examples 10-13; using C65 and 5-(difluoromethoxy) pyrazine-2-carboxylic acid | 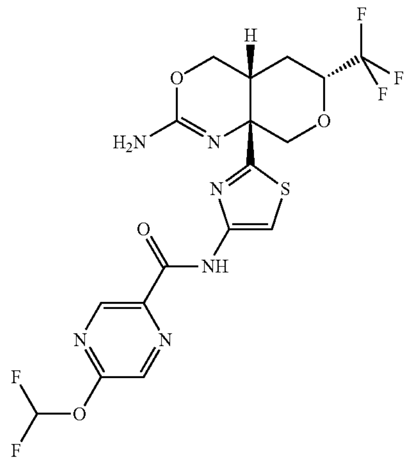 [SMILES: NC1=N[C@@]2(c3nc(NC(=O)c4cnc(OC(F)F)cn4)cs3)CO[C@@H](C(F)(F)F)C[C@H]2CO1] | $^1$H NMR (400 MHz, CD$_3$OD) δ (ppm) 9.01 (s, 1H), 8.51 (s, 1H), 7.87 (s, 1H), 7.67 (t, J = 71.3 Hz, 1H), 4.21-4.34 (m, 2H), 4.01-4.13 (m, 2H), 3.01 (m, 1H), 2.07 (m, 1H), 1.76 (q, J = 12.7 Hz, 1H), 1.27-1.39 (m, 1H); Mass spectrum, observed ion 495.0 m/z (M + H$^+$) |
| 21 | Analogous to Examples 10-13; using C65 and 5-cyano-3-methyl picolinic acid | 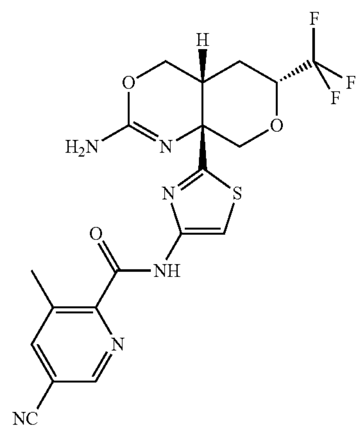 [SMILES: Cc1cc(C#N)cnc1C(=O)Nc1csc([C@]23CO[C@@H](C(F)(F)F)C[C@H]2COC(N)=N3)n1] | $^1$H NMR (400 MHz, CDCl$_3$) δ (ppm); 10.59 (s, 1H), 8.74 (d, J = 1.5 Hz, 1H), 7.96 (d, J = 2.0 Hz, 1H), 7.75 (s, 1H), 4.35 (br s, 2H), 3.95-4.05 (m, 3H), 3.87-3.91 (m, 2H), 2.74-2.80 (s, 3H), 2.77 (m, 1H), 1.83-1.97 (m, 2H); Mass spectrum, observed ion 467.0 m/z (M + H$^+$) |
| 22 | Analogous to Examples 10-13; using C65 and 5-(difluoromethoxy)-3-methyl pyrazine-2-carboxylic acid | 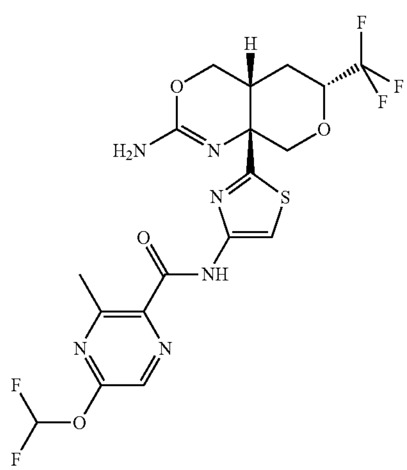 [SMILES: Cc1nc(OC(F)F)cnc1C(=O)Nc1csc([C@]23CO[C@@H](C(F)(F)F)C[C@H]2COC(N)=N3)n1] | $^1$H NMR (400 MHz, CDCl$_3$) δ (ppm); 10.31 (s, 1H), 8.20 (s, 1H), 7.73 (s, 1H), 7.54 (t, J = 71 Hz, 1H), 4.30 (br s, 2H), 3.93-4.07 (m, 3H), 3.86-3.92 (m, 2H), 2.99 (s, 3H), 2.72-2.78 (m, 1H), 1.82-1.96 (m, 2H); Mass spectrum, observed ion 509.0 m/z (M + H$^+$) |

| Example Number | Method of Preparation; Intermediates | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 23 | Analogous to Examples 10-13; using C65 and 5-methoxy-3-methyl pyrazine-2-carboxylic acid | 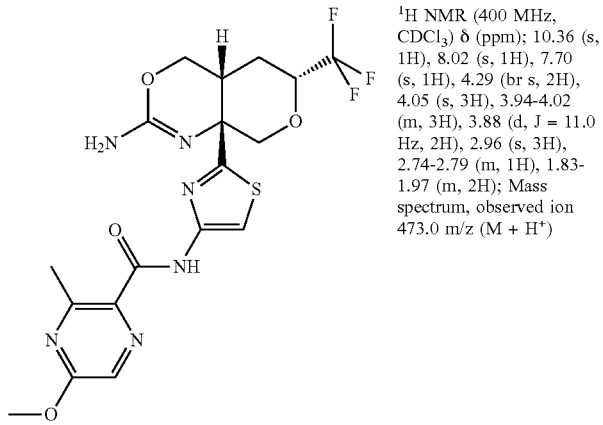 | $^1$H NMR (400 MHz, CDCl$_3$) δ (ppm); 10.36 (s, 1H), 8.02 (s, 1H), 7.70 (s, 1H), 4.29 (br s, 2H), 4.05 (s, 3H), 3.94-4.02 (m, 3H), 3.88 (d, J = 11.0 Hz, 2H), 2.96 (s, 3H), 2.74-2.79 (m, 1H), 1.83-1.97 (m, 2H); Mass spectrum, observed ion 473.0 m/z (M + H$^+$) |
| 24 | Analogous to Examples 10-13; using C65 and 5-cyano picolinic acid | 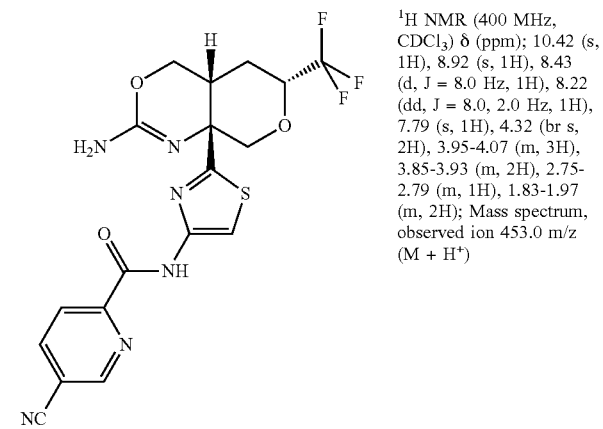 | $^1$H NMR (400 MHz, CDCl$_3$) δ (ppm); 10.42 (s, 1H), 8.92 (s, 1H), 8.43 (d, J = 8.0 Hz, 1H), 8.22 (dd, J = 8.0, 2.0 Hz, 1H), 7.79 (s, 1H), 4.32 (br s, 2H), 3.95-4.07 (m, 3H), 3.85-3.93 (m, 2H), 2.75-2.79 (m, 1H), 1.83-1.97 (m, 2H); Mass spectrum, observed ion 453.0 m/z (M + H$^+$) |

BIOLOGICAL ASSAYS

BACE1 Cell-Free Assay:

Beta-secretase (BACE) is one of the enzymes involved in the generation of the amyloid beta peptide found in the amyloid plaques of Alzheimer's disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY^EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a ½ log dose response curve from a top concentration of 100 μM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 μL assay buffer [100 mM sodium acetate, pH 4.5 (brought to pH with acetic acid), and 0.001% Tween-20]. Plates are covered and incubated for 3 hours at 37° C. The reaction is stopped with the addition of 30 μL of 1.5 μM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

IC50 data for Examples 1-19, as provided in Table 2 below, was obtained using the BACE1 Cell-Free Assay.

TABLE 2

| | | BACE1 Cell-Free Assay Mean IC50 | |
|---|---|---|---|
| Example | Structure | (µM) | IUPAC NAME |
| 1 | | 0.214 | N-(2-((4aR,6S,8aR)-2-amino-6-methyl-4,4a,5,6-tetrahydropyrano[3,4-d][1,3]oxazin-8a(8H)-yl)thiazol-4-yl)-5-(difluoromethoxy)picolinamide |
| 2 | | 0.123 | N-(2-((4aR,6S,8aR)-2-amino-6-methyl-4,4a,5,6-tetrahydropyrano[3,4-d][1,3]oxazin-8a(8H)-yl)thiazol-4-yl)-3-chloro-5-(difluoromethoxy)picolinamide |
| 3 | | 0.085 | N-(2-((4aR,6S,8aR)-2-amino-6-methyl-4,4a,5,6-tetrahydropyrano[3,4-d][1,3]oxazin-8a(8H)-yl)thiazol-4-yl)-5-(difluoromethoxy)-3-methylpicolinamide |

TABLE 2-continued

Biological Data, Structure and IUPAC Names for Examples 1-19

| Example | Structure | BACE1 Cell-Free Assay Mean IC50 (µM) | IUPAC NAME |
|---|---|---|---|
| 4 | 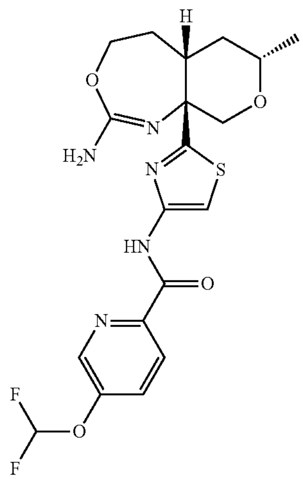 [SMILES: C[C@H]1C[C@H]2CCOC(N)=N[C@@]2(c2nc(NC(=O)c3ccc(OC(F)F)cn3)cs2)CO1] | 0.146 | N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy)picolinamide |
| 5 | 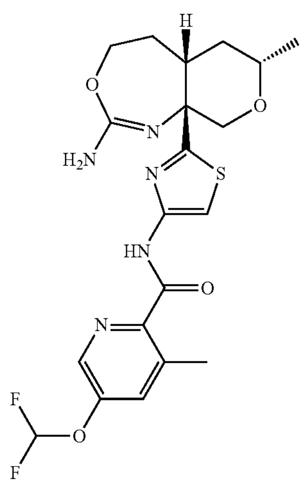 [SMILES: Cc1cc(OC(F)F)cnc1C(=O)Nc1csc([C@]23CO[C@@H](C)C[C@H]2CCOC(N)=N3)n1] | 0.071 | N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy)-3-methylpicolinamide |
| 6 | 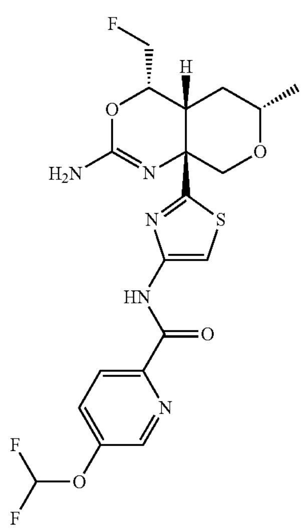 [SMILES: C[C@H]1C[C@H]2[C@@H](CF)OC(N)=N[C@@]2(c2nc(NC(=O)c3ccc(OC(F)F)cn3)cs2)CO1] | 0.270 | N-(2-((4S,4aR,6S,8aR)-2-amino-4-(fluoromethyl)-6-methyl-4,4a,5,6-tetrahydropyrano[3,4-d][1,3]oxazin-8a(8H)-yl)thiazol-4-yl)-5(difluoromethoxy)picolinamide |

TABLE 2-continued

Biological Data, Structure and IUPAC Names for Examples 1-19

| Example | Structure | BACE1 Cell-Free Assay Mean IC50 (µM) | IUPAC NAME |
|---|---|---|---|
| 7 | 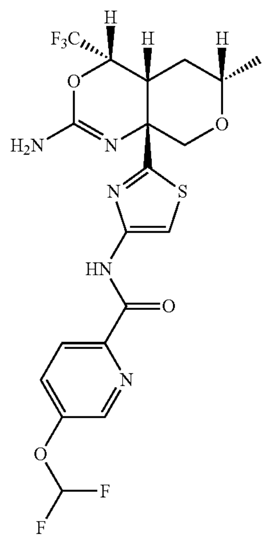 [SMILES: C[C@H]1C[C@H]2[C@@H](C(F)(F)F)OC(N)=N[C@@]2(c2nc(NC(=O)c3ccc(OC(F)F)cn3)cs2)CO1] | 0.112 | N-(2-((4S,4aR,6S,8aR)-2-amino-6-methyl-4-(trifluoromethyl)-4,4a,5,6-tetrahydropyrano[3,4-d][1,3]oxazin-8a(8H)-yl)thiazol-4-yl)-5-(difluoromethoxy)picolinamide |
| 8 | 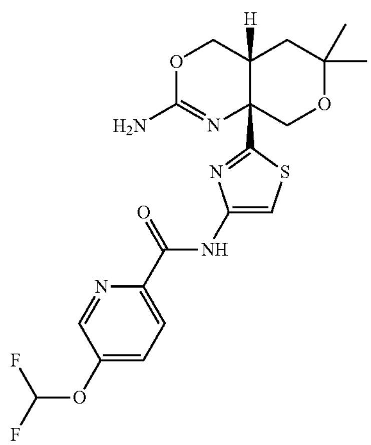 [SMILES: CC1(C)C[C@H]2COC(N)=N[C@@]2(c2nc(NC(=O)c3ccc(OC(F)F)cn3)cs2)CO1] | 0.610 | N-(2-((4aR,8aR)-2-amino-6,6-dimethyl-4,4a(5,6-tetrahydropyrano[3,4-d][1,3]oxazin-8a(8H)-yl)thiazol-4-yl)-5-(difluoromethoxy)picolinamide |
| 9 | 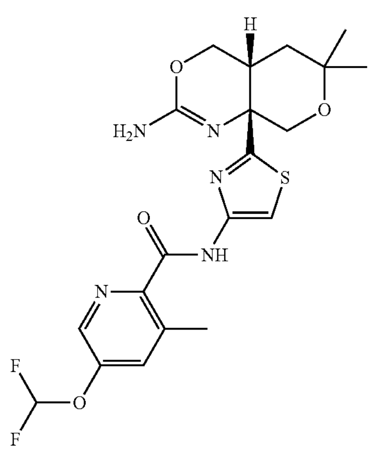 [SMILES: Cc1cc(OC(F)F)cnc1C(=O)Nc1csc([C@]23COC(C)(C)C[C@H]2COC(N)=N3)n1] | 0.475 | N-(2-((4aR,8aR)-2-amino-6,6-dimethyl-4,4a,5,6-tetrahydropyrano[3,4-d][1,3]oxazin-8a(8H)-yl)thiazol-4-yl)-5-(difluoromethoxy)-3-methylpicolinamide |

TABLE 2-continued

Biological Data, Structure and IUPAC Names for Examples 1-19

| Example | Structure | BACE1 Cell-Free Assay Mean IC50 (μM) | IUPAC NAME |
|---|---|---|---|
| 10b | 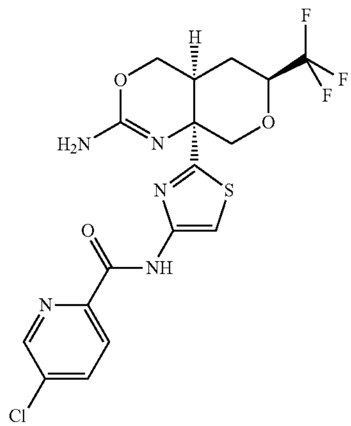 [SMILES: NC1=N[C@]2(c3nc(NC(=O)c4ccc(Cl)cn4)cs3)CO[C@H](C(F)(F)F)C[C@@H]2CO1] | 16.7 | N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-5-chloropicolinamide |
| 10a | 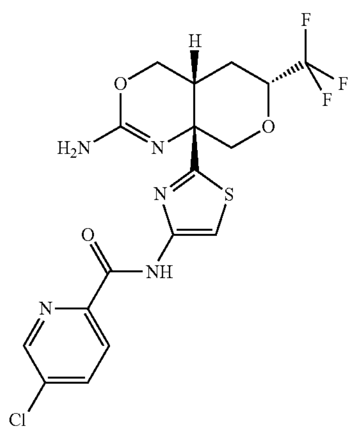 [SMILES: NC1=N[C@@]2(c3nc(NC(=O)c4ccc(Cl)cn4)cs3)CO[C@@H](C(F)(F)F)C[C@H]2CO1] | 3.10 | N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-5-chloropicolinamide |
| 11b | 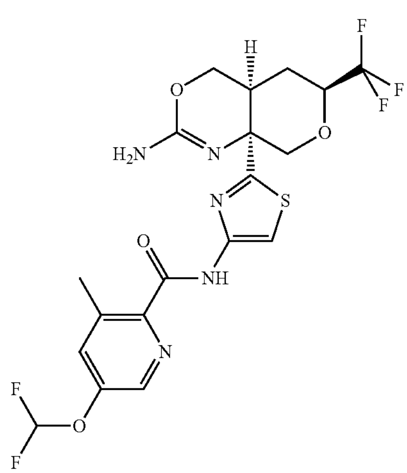 [SMILES: Cc1cc(OC(F)F)cnc1C(=O)Nc1csc([C@@]23CO[C@H](C(F)(F)F)C[C@@H]2COC(N)=N3)n1] | 10.8 | N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide |

TABLE 2-continued

Biological Data, Structure and IUPAC Names for Examples 1-19

| Example | Structure | BACE1 Cell-Free Assay Mean IC50 (μM) | IUPAC NAME |
|---|---|---|---|
| 11a | 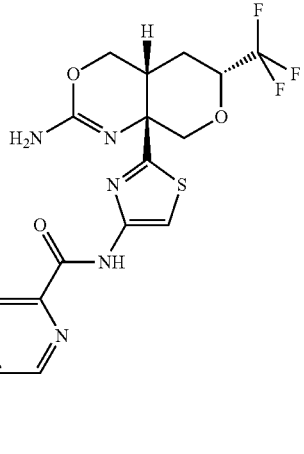 | 0.155 | N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-5-(difluoromethoxy)-3-methylpicolinamide |
| 12b | 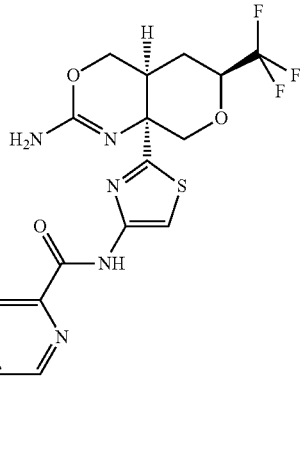 | 15.0 | N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-5-(difluoromethoxy)picolinamide |
| 12a | 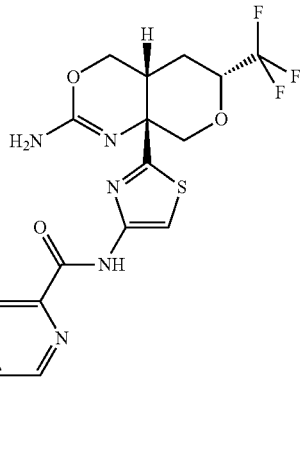 | 0.371 | N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-5-(difluoromethoxy)picolinamide |

TABLE 2-continued

Biological Data, Structure and IUPAC Names for Examples 1-19

| Example | Structure | BACE1 Cell-Free Assay Mean IC50 (μM) | IUPAC NAME |
|---|---|---|---|
| 13b | 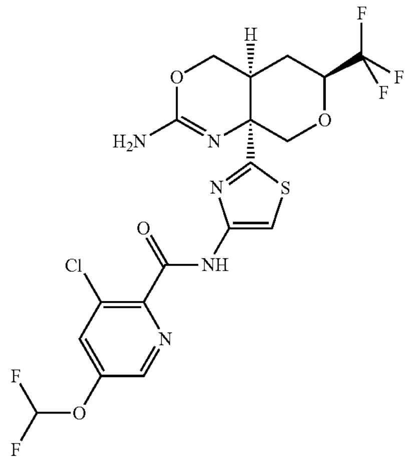 [SMILES: NC1=N[C@]2(c3nc(NC(=O)c4ncc(OC(F)F)cc4Cl)cs3)CO[C@H](C(F)(F)F)C[C@@H]2CO1] | 6.97 | N-(2-((4aS,6S,8aS)-2-amino-6-(trifluoromethyl)-4,4a,5,6-tetrahydropyrano[3,4-d][1,3]oxazin-8a(8H)-yl)thiazol-4-yl)-3-chloro-5-(difluoromethoxy)picolinamide |
| 13a | 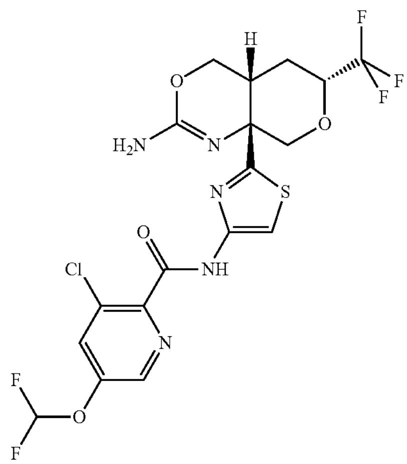 [SMILES: NC1=N[C@@]2(c3nc(NC(=O)c4ncc(OC(F)F)cc4Cl)cs3)CO[C@@H](C(F)(F)F)C[C@H]2CO1] | 0.184 | N-(2-((4aR,6R,8aR)-2-amino-6-(trifluoromethyl)-4,4a,5,6-tetrahydropyrano[3,4-d][1,3]oxazin-8a(8H)-yl)thiazol-4-yl)-3-chloro-5-(difluoromethoxy)picolinamide |
| 14 | 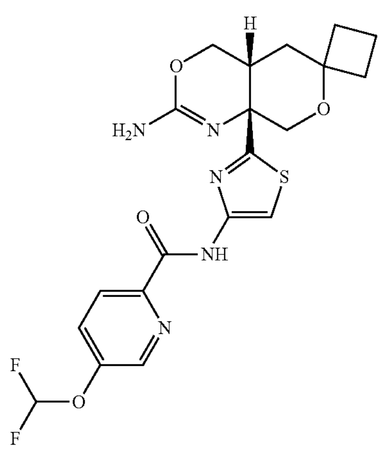 [SMILES: NC1=N[C@@]2(c3nc(NC(=O)c4ccc(OC(F)F)cn4)cs3)COC3(CCC3)C[C@H]2CO1] | 0.860 | N-(2-((4a'R,8a'R)-2'-amino-4a',5'-dihydro-4'H-spiro[cyclobutane-1,6'-pyrano3,4-d][1,3]oxazin]-8a'(8'H)-yl)thiazol-4-yl)-5-(difluoromethoxy)picolinamide |

TABLE 2-continued

Biological Data, Structure and IUPAC Names for Examples 1-19

| Example | Structure | BACE1 Cell-Free Assay Mean IC50 (μM) | IUPAC NAME |
|---|---|---|---|
| 15 | 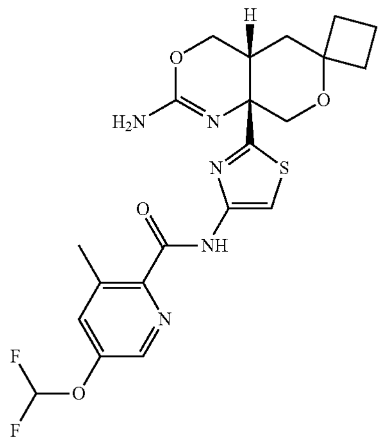 [SMILES: Cc1cc(OC(F)F)cnc1C(=O)Nc1csc([C@]23COC4(CCC4)C[C@H]2COC(N)=N3)n1] | 0.370 | N-(2-((4a'R,8a'R)-2'-amino-4a',5'-dihydro-4'H-spiro[cyclobutane-1,6'-pyrano[3,4-d][1,3]oxazin]-8a'(8'H)-yl)thiazol-4-yl)-5-(difluoromethoxy)-3-methyl picolinamide |
| 16 | 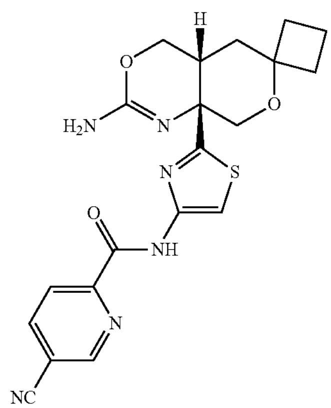 [SMILES: N#Cc1ccc(C(=O)Nc2csc([C@]34COC5(CCC5)C[C@H]3COC(N)=N4)n2)nc1] | 0.395 | N-(2-((4a'R,8a'R)-2'-amino-4a',5'-dihydro-4'H-spiro[cyclobutane-1,6'-pyrano[3,4-d][1,3]oxazin]-8a'(8'H)-yl)thiazol-4-yl)-5-cyano picolinamide |
| 17 | 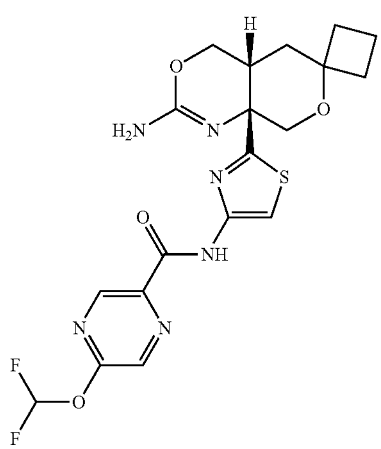 [SMILES: NC1=N[C@@]2(c3nc(NC(=O)c4cnc(OC(F)F)cn4)cs3)COC3(CCC3)C[C@H]2CO1] | 2.263 | N-(2-((4a'R,8a'R)-2'-amino-4a',5'-dihydro-4'H-spiro[cyclobutane-1,6'-pyrano[3,4-d][1,3]oxazin]-8a'(8'H)-yl)thiazol-4-yl)-5-(difluoromethoxy)pyrazine-2-carboxamide |

TABLE 2-continued

Biological Data, Structure and IUPAC Names for Examples 1-19

| Example | Structure | BACE1 Cell-Free Assay Mean IC50 (μM) | IUPAC NAME |
|---|---|---|---|
| 18 | 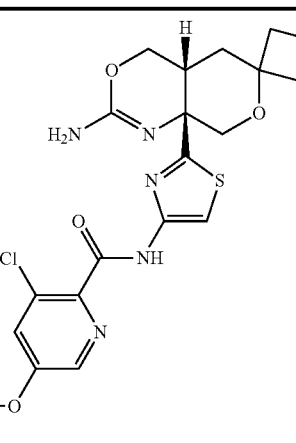 | 0.561 | N-(2-((4a'R,8a'R)-2'-amino-4a',5'-dihydro-4'H-spiro[cyclobutane-1,6'-pyrano[3,4-d][1,3]oxazin]-8a'(8'H)-yl)thiazol-4-yl)-3-chloro-5-(difluoromethoxy)picolinamide |
| 19 | 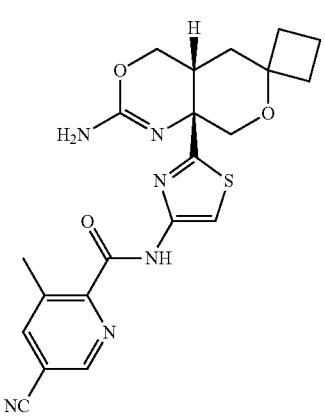 [SMILES: Cc1cc(C#N)cnc1C(=O)Nc1csc([C@]23COC4(CCC4)C[C@H]2COC(N)=N3)n1] | 0.185 | N-(2-((4a'R,8a'R)-2'-amino-4a',5'-dihydro-4'H-spiro[cyclobutane-1,6'-pyrano[3,4-d][1,3]oxazin]-8a'(8'H)-yl)thiazol-4-yl)-5-cyano-3-methylpicolinamide |

BACE1 Scintillation Proximity Binding Assay (SPA):

The BACE1 binding assay measured beta-site amyloid precursor protein-cleaving enzyme (BACE) binding as a decrease in the counts of radioligand bound in a scintillation proximity assay (SPA). Utilizing a radiolabeled small molecule BACE active site binding inhibitor and crude HEK cell membrane preparations over-expressing full length BACE1, the binding of enzyme by test compound was monitored as a reduction of specific counts bound at pH 6.0. Full length human BACE1 over-expressed in HEK cells was prepared by Pfizer scientists. Frozen stock cell paste was reacted in 50 mM sodium acetate buffer (pH=6.0) containing 3H-(4aR,6R,8aS)-8a-(2,4-difluorophenyl)-6-(1-methyl-1H-pyrazol-4-yl)-4,4a,5,6,8,8a-hexahydropyrano[3,4-d][1,3] thiazin-2-amine ligand, SPA bead and 60 μM to 600 pM of test compound in an assay volume of 27 uL. The compound plate also contained positive (BACE inhibitor) and negative (DMSO) control wells. The binding was carried out at room temperature for 30 minutes and then the plates were read on a TriLux Microbeta reader to determine the number of counts bound. The raw data was converted to percent effect compared to positive and negative control wells and the compound concentrations and % effect values for tested compounds were plotted to determine the 50% effect (IC50) with a four-parameter logistic dose response equation.

IC50 data for Examples 20-24, as provided in Table 3 below, was obtained using the BACE1 Scintillation Proximity Assay (SPA).

TABLE 3

Biological Data, Structure and IUPAC Names for Examples 20-24

| Example Number | Structure | BACE1 Scintillation Proximity Assay SPA Mean IC50 (μM) | IUPAC NAME |
|---|---|---|---|
| 20 | 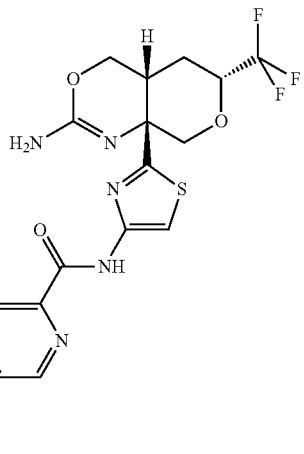 | 0.124 | N-{2-[(4aR,6R,8aR)-2-amino-6-(trifluoromethyl)-4,4a(5,6-tetrahydropyrano[3,4-d][1,3]oxazin-8a(8H)-yl]-1,3-thiazol-4-yl}-5-(difluoromethoxy)pyrazine-2-carboxamide |
| 21 | 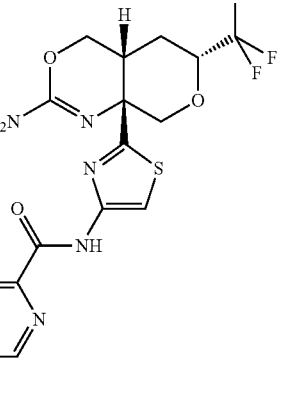 | 0.005 | N-{2-[(4aR,6R,8aR)-2-amino-6-(trifluoromethyl)-4,4a,5,6-tetrahydropyrano[3,4-d][1,3]oxazin-8a(8H)-yl]-1,3-thiazol-4-yl}-5-cyano-3-methylpyridine-2-carboxamide |
| 22 | 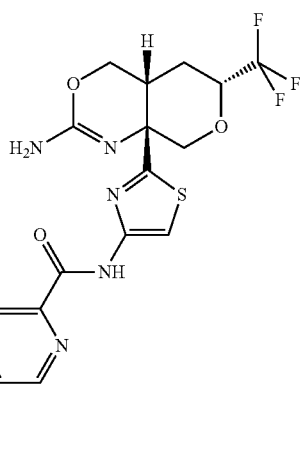 | 0.013 | N-{2-[{4aR,6R,8aR)-2-amino-6-(trifluoromethyl)-4,4a,5,6-tetrahydropyrano[3,4-d][1,3]oxazin-8a(8H)-yl]-1,3-thiazol-4-yl}-5-(difluoromethoxy)-3-methyl pyrazine-2-carboxamide |

TABLE 3-continued

Biological Data, Structure and IUPAC Names for Examples 20-24

| Example Number | Structure | BACE1 Scintillation Proximity Assay SPA Mean IC50 (μM) | IUPAC NAME |
|---|---|---|---|
| 23 | 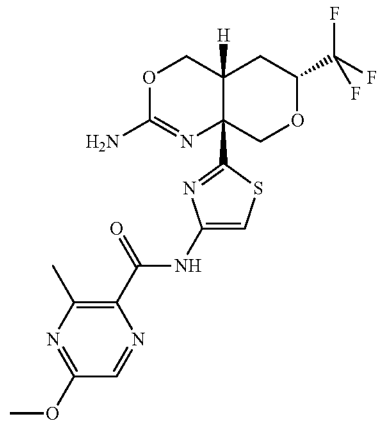 [SMILES: COc1cnc(C(=O)Nc2csc([C@]34CO[C@@H](C(F)(F)F)C[C@H]3COC(N)=N4)n2)c(C)n1] | 0.162 | N-{2-[(4aR,6R,8aR)-2-amino-6-(trifluoromethyl)-4,4a,5,6-tetrahydropyrano[3,4-d][1,3]oxazin-8a(8H)-yl]-1,3-thiazol-4-yl}-5-methoxy-3-methylpyrazine-2-carboxamide |
| 24 | 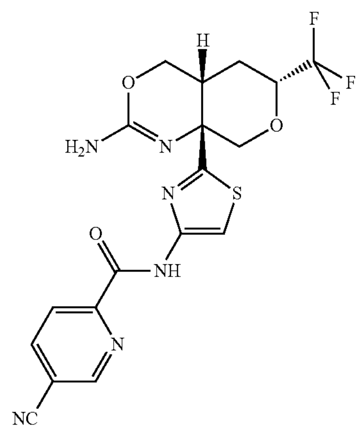 [SMILES: N#Cc1ccc(C(=O)Nc2csc([C@]34CO[C@@H](C(F)(F)F)C[C@H]3COC(N)=N4)n2)nc1] | 0.027 | N-{2-[(4aR,6R,8aR)-2-amino-6-(trifluoromethyl)-4,4a,5,6-tetrahydropyrano[3,4-d][1,3]oxazin-8a(8H)-yl]-1,3-thiazol-4-yl}-5-cyano pyridine-2-carboxamide |

We claim:

1. A pharmaceutical composition comprising a therapeutically effective amount of a compound of formula I

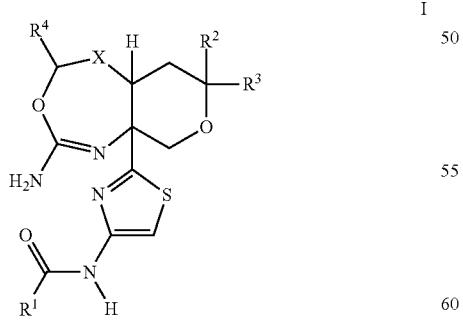

wherein $R^1$ is a 5- to 6-membered heteroaryl, having one to four heteroatoms independently selected from N, O or S, wherein at least one of the heteroatoms is N and wherein said N is optionally substituted with $R^6$; and wherein said 5- to 6-membered heteroaryl is optionally substituted on carbon with one to three $R^5$;

$R^2$ and $R^3$ are each independently selected from the group consisting of hydrogen, $C_{1-3}$alkyl, $C_{3-6}$cycloalkyl and 3- to 7-membered heterocycloalkyl; wherein the $C_{1-3}$alkyl is optionally and independently with one to three fluoro or $C_{1-3}$alkoxy, and the $C_{3-6}$cycloalkyl and 3- to 7-membered heterocycloalkyl are each optionally and independently substituted with one to three fluoro, $C_{1-3}$alkyl or $C_{1-3}$alkoxy;

or $R^2$ and $R^3$ taken together with the carbon to which they are attached form a $C_{3-6}$ cycloalkyl ring or a 3- to 7-membered heterocycloalkyl, each of which is optionally and independently substituted with one to three fluoro, $C_{1-3}$alkyl or $C_{1-3}$alkoxy;

$R^4$ is hydrogen or $C_{1-3}$alkyl optionally substituted with one to three fluoro;

X is $CH_2$ or a bond;

$R^5$ at each occurrence is independently selected from the group consisting of halo, hydroxy, cyano, $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl; wherein said $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-C1-6alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; and $R^6$ is hydrogen or $C_{1-6}$alkyl;

or a tautomer thereof or a pharmaceutically acceptable salt of said compound or tautomer;

one or more additional pharmaceutical agent; and a pharmaceutically acceptable vehicle, diluent or carrier.

2. The pharmaceutical composition of claim 1, comprising a therapeutically effective amount of a compound of formula Ia

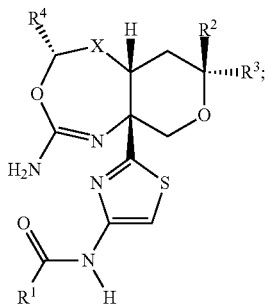

Ia or a tautomer thereof or a pharmaceutically acceptable salt of said compound or tautomer;

one or more additional pharmaceutical agent; and a pharmaceutically acceptable vehicle, diluent or carrier.

3. The pharmaceutical composition of claim 1, comprising a therapeutically effective amount of a compound formula Ib

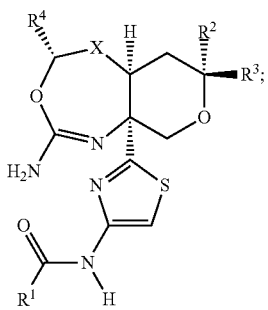

Ib or a tautomer thereof or a pharmaceutically acceptable salt of said compound or tautomer;

one or more additional pharmaceutical agent; and a pharmaceutically acceptable vehicle, diluent or carrier.

4. The pharmaceutical composition of claim 1 which the compound is selected from the group consisting of N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy) picolinamide; and N-(2-((5aR,7S,9aR)-2-amino-7-methyl-5,5a,6,7-tetrahydro-4H-pyrano[3,4-d][1,3]oxazepin-9a(9H)-yl)thiazol-4-yl)-5-(difluoromethoxy)-3-methylpicolinamide;

N-(2-((4aR,8aR)-2-amino-6,6-dimethyl-4,4a,5,6-tetrahydropyrano[3,4-d][1,3]oxazin-8a(8H)-yl)thiazol-4-yl)-5-(difluoromethoxy)picolinamide; and N-(2-((4aR,8aR)-2-amino-6,6-dimethyl-4,4a,5,6-tetrahydropyrano[3,4-d][1,3]oxazin-8a(8H)-yl)thiazol-4-yl)-5-(difluoromethoxy)-3-methylpicolinamide;

N-(2-((4aR,6S,8aR)-2-amino-6-methyl-4,4a,5,6-tetrahydropyrano[3,4-d][1,3]oxazin-8a(8H)-yl)thiazol-4-yl)-5-(difluoromethoxy)picolinamide;

N-(2-((4aR,6S,8aR)-2-amino-6-methyl-4,4a,5,6-tetrahydropyrano[3,4-d][1,3]oxazin-8a(8H)-yl)thiazol-4-yl)-3-chloro-5-(difluoromethoxy)picolinamide;

N-(2-((4aR,6S,8aR)-2-amino-6-methyl-4,4a,5,6-tetrahydropyrano[3,4-d][1,3]oxazin-8a(8H)-yl)thiazol-4-yl)-5-(difluoromethoxy)-3-methylpicolinamide;

N-(2-((4S,4aR,6S,8aR)-2-amino-4-(fluoromethyl)-6-methyl-4,4a,5,6-tetrahydropyrano [3,4-d][1,3]oxazin-8a(8H)-yl)thiazol-4-yl)-5-(difluoromethoxy)picolinamide;

N-(2-((4S,4aR,6S,8aR)-2-amino-6-methyl-4-(trifluoromethyl)-4,4a,5,6-tetrahydropyrano [3,4-d][1,3]oxazin-8a (8H)-yl)thiazol-4-yl)-5-(difluoromethoxy)picolinamide;

N-(2-((4aR,6R,8aR)-2-amino-6-(trifluoromethyl)-4,4a,5, 6-tetrahydropyrano[3,4-d][1,3]oxazin-8a(8H)-yl)thiazol-4-yl)-5-chloropicolinamide;

N-(2-((4aR,6R,8aR)-2-amino-6-(trifluoromethyl)-4,4a,5, 6-tetrahydropyrano[3,4-d][1,3]oxazin-8a(8H)-yl)thiazol-4-yl)-5-(difluoromethoxy)-3-methylpicolinamide;

N-(2-((4aR,6R,8aR)-2-amino-6-(trifluoromethyl)-4,4a,5, 6-tetrahydropyrano[3,4-d][1,3]oxazin-8a(8H)-yl)thiazol-4-yl)-5-(difluoromethoxy)picolinamide; and N-(2-((4aR,6R,8aR)-2-amino-6-(trifluoromethyl)-4,4a,5, 6-tetrahydropyrano[3,4-d][1,3]oxazin-8a(8H)-yl)thiazol-4-yl)-3-chloro-5-(difluoromethoxy)picolinamide;

N-(2-((4aS,6S,8aS)-2-amino-6-(trifluoromethyl)-4,4a,5, 6-tetrahydropyrano[3,4-d][1,3]oxazin-8a(8H)-yl)thiazol-4-yl)-5-chloropicolinamide;

N-(2-((4aS,6S,8aS)-2-amino-6-(trifluoromethyl)-4,4a,5, 6-tetrahydropyrano[3,4-d][1,3]oxazin-8a(8H)-yl)thiazol-4-yl)-5-(difluoromethoxy)-3-methylpicolinamide;

N-(2-((4aS,6S,8aS)-2-amino-6-(trifluoromethyl)-4,4a,5, 6-tetrahydropyrano[3,4-d][1,3]oxazin-8a(8H)-yl)thiazol-4-yl)-5-(difluoromethoxy)picolinamide; and N-(2-((4aS,6S,8aS)-2-amino-6-(trifluoromethyl)-4,4a,5, 6-tetrahydropyrano[3,4-d][1,3]oxazin-8a(8H)-yl)thiazol-4-yl)-3-chloro-5-(difluoromethoxy)picolinamide;

N-(2-((4a'R,8a'R)-2'-amino-4a',5'-dihydro-4'H-spiro [cyclobutane-1,6'-pyrano 3,4-d][1,3]oxazin]-8a'(8'H)-yl) thiazol-4-yl)-5-(difluoromethoxy) picolinamide;

N-(2-((4a'R,8a'R)-2'-amino-4a',5'-dihydro-4'H-spiro [cyclobutane-1,6'-pyrano [3,4-d][1,3]oxazin]-8a'(8'H)-yl) thiazol-4-yl)-5-(difluoromethoxy)-3-methyl picolinamide;

N-(2-((4a'R,8a'R)-2'-amino-4a',5'-dihydro-4'H-spiro [cyclobutane-1,6'-pyrano [3,4-d][1,3]oxazin]-8a'(8'H)-yl) thiazol-4-yl)-5-cyano picolinamide;

N-(2-((4a'R,8a'R)-2'-amino-4a',5'-dihydro-4'H-spiro [cyclobutane-1,6'-pyrano [3,4-d][1,3]oxazin]-8a'(8'H)-yl) thiazol-4-yl)-5-cyano picolinamide;

N-(2-((4a'R,8a'R)-2'-amino-4a',5'-dihydro-4'H-spiro[cyclobutane-1,6'-pyrano[3,4-d][1,3]oxazin]-8a'(8'H)-yl) thiazol-4-yl)-5-(difluoromethoxy)pyrazine-2-carboxamide;

N-(2-((4a'R,8a'R)-2'-amino-4a',5'-dihydro-4'H-spiro [cyclobutane-1,6'-pyrano[3,4-d][1,3]oxazin]-8a'(8'H)-yl) thiazol-4-yl)-3-chloro-5-(difluoromethoxy) picolinamide; and N-(2-((4a'R,8a'R)-2'-amino-4a',5'-dihydro-4'H-spiro[cyclobutane-1,6'-pyrano[3,4-d][1,3]oxazin]-8a'(8'H)-yl) thiazol-4-yl)-5-cyano-3-methylpicolinamide;

or a tautomer thereof or a pharmaceutically acceptable salt of said compound or tautomer.

5. The pharmaceutical composition of claim 1 wherein the additional pharmaceutical agent is selected from the group consisting of an anti-obesity agent, an anti-diabetic agent, a lipid lowering agent, an anti-hypertensive agent, an acetylcholinesterase inhibitor, an antibody to amyloid-□, an amyloid-lowering or amyloid-inhibiting agent, an alpha-adrenergic receptor agonist, a beta-adrenergic blocking agent, an anticholinergic, an anticonvulsant, an antipsychotic, a calcium channel blocker, an O-methyltransferase inhibitor, a central nervous system stimulant, a corticosteroid, a dopamine receptor agonist or antagonist, a dopamine reuptake inhibitor, a gamma-aminobutyric receptor agonist, an immunosuppressant, an interferon, a muscarinic receptor agonist, a nicotinic receptor agonist, a norepinephrine reuptake inhibitor, a histamine 3 antagonist, a N-methyl-D-aspartate receptor antagonist, a monoamine oxidase inhibitor, a phosphodiesterase inhibitor, a serotonin 5-$HT_{1A}$ receptor antagonist, a serotonin 5-$HT_{2C}$ receptor agonist, a serotonin 5-$HT_4$ receptor agonist/antagonist, a serotonin 5-$HT_{3C}$ receptor antagonist, a serotonin 5-$HT_6$ receptor antagonist, a serotonin 5-HT reuptake inhibitor, a glycine transporter-1 inhibitor, a P450 inhibitor and an anti-tau agent.

6. The pharmaceutical composition of claim 1 wherein the additional pharmaceutical agent is an amyloid-lowering or amyloid-inhibiting agent which is selected from the group consisting of a BACE inhibitor, a gamma secretase modulator and a RAGE inhibitor.

* * * * *